(12) United States Patent
Pless et al.

(10) Patent No.: US 8,311,632 B2
(45) Date of Patent: Nov. 13, 2012

(54) DEVICES, METHODS, AND SYSTEMS FOR HARVESTING ENERGY IN THE BODY

(75) Inventors: Benjamin David Pless, Atherton, CA (US); Carl Lance Boling, San Jose, CA (US); Barbara Gibb, Foster City, CA (US); Adolf van der Heide, San Jose, CA (US); Brett M. Wingeier, San Francisco, CA (US)

(73) Assignee: Autonomic Technologies, Inc., Redwood City, CA (US)

( * ) Notice: Subject to any disclaimer, the term of this patent is extended or adjusted under 35 U.S.C. 154(b) by 720 days.

(21) Appl. No.: 12/392,938

(22) Filed: Feb. 25, 2009

(65) Prior Publication Data

US 2009/0216292 A1  Aug. 27, 2009

Related U.S. Application Data

(60) Provisional application No. 61/031,272, filed on Feb. 25, 2008, provisional application No. 61/125,855, filed on Apr. 26, 2008, provisional application No. 61/081,261, filed on Jul. 16, 2008, provisional application No. 61/093,988, filed on Sep. 3, 2008, provisional application No. 61/096,259, filed on Sep. 11, 2008, provisional application No. 61/098,688, filed on Sep. 19, 2008.

(51) Int. Cl.
*A61N 1/00* (2006.01)
(52) U.S. Cl. .......................................... 607/35; 607/61
(58) Field of Classification Search .............. 607/27–29, 607/34, 35, 59, 60, 61
See application file for complete search history.

(56) References Cited

U.S. PATENT DOCUMENTS

| 3,899,366 A | 8/1975 | Tajkowski |
| 3,906,960 A | 9/1975 | Lehr |
| 4,082,097 A * | 4/1978 | Mann et al. ............... 607/33 |
| 4,166,470 A | 9/1979 | Neumann |

(Continued)

FOREIGN PATENT DOCUMENTS

| WO | WO 2006/121818 A2 | 11/2006 |
| WO | WO 2007/102937 A2 | 9/2007 |

OTHER PUBLICATIONS

Ballard et al.; Leg intramuscular pressures during locomotion in humans; J. Appl. Physiol.; vol. 84; No. 6; pp. 1976-1981; 1998.

(Continued)

*Primary Examiner* — Scott Getzow
(74) *Attorney, Agent, or Firm* — Shay Glenn LLP

(57) ABSTRACT

In some embodiments, the power generator for converting mechanical energy to electrical energy is described may include a compressible element adapted and configured to be placed in an environment having a variable compressive force such as varying ambient pressures. The compressible element may be compressed by a force applied by the variable pressure to the compressible element. The power generator may further include a transducer that may be coupled to the compressible element and that may convert mechanical energy from the compression of the compressible element to electrical energy. In some embodiments, the power generator may be adapted to be an implantable power generator for converting mechanical energy from a patient to electrical energy, such that the compressible element adapted and configured to be placed between two adjacent tissue layers of the patient and to be compressed by a force applied from the two adjacent tissue layers to the compressible element.

56 Claims, 27 Drawing Sheets

U.S. PATENT DOCUMENTS

| | | | |
|---|---|---|---|
| 4,690,143 | A | 9/1987 | Schroeppel |
| 5,431,694 | A | 7/1995 | Snaper et al. |
| 5,702,303 | A | 12/1997 | Takemoto et al. |
| 5,810,015 | A | 9/1998 | Flaherty |
| 6,198,645 | B1 | 3/2001 | Kotowski et al. |
| 6,407,483 | B1 | 6/2002 | Nunuparov et al. |
| 6,595,912 | B2 | 7/2003 | Lau et al. |
| 6,936,994 | B1 | 8/2005 | Gimlan |
| 7,003,350 | B2 | 2/2006 | Denker et al. |
| 2003/0199955 | A1 | 10/2003 | Struble et al. |
| 2004/0133069 | A1 | 7/2004 | Shapland et al. |
| 2004/0172087 | A1 | 9/2004 | Forsell |
| 2004/0211043 | A1 | 10/2004 | Will |
| 2005/0027332 | A1 | 2/2005 | Avrahami et al. |
| 2006/0009831 | A1 | 1/2006 | Lau et al. |
| 2006/0136010 | A1 | 6/2006 | Spelman et al. |
| 2006/0235263 | A1 | 10/2006 | Jacobson et al. |
| 2006/0245140 | A1 | 11/2006 | Hunt et al. |
| 2007/0038238 | A1 | 2/2007 | Freeman et al. |
| 2007/0049789 | A1 | 3/2007 | Abrams |
| 2007/0066997 | A1 | 3/2007 | He et al. |
| 2007/0088402 | A1 | 4/2007 | Melvin |
| 2007/0156179 | A1 | 7/2007 | Kashurov |
| 2007/0167988 | A1 | 7/2007 | Cernasov |
| 2007/0293904 | A1* | 12/2007 | Gelbart et al. .......... 607/35 |
| 2008/0021505 | A1* | 1/2008 | Hastings et al. .......... 607/9 |
| 2008/0200963 | A1 | 8/2008 | Pless et al. |
| 2008/0277943 | A1 | 11/2008 | Donelan et al. |
| 2008/0278028 | A1 | 11/2008 | Donelan et al. |
| 2009/0171448 | A1 | 7/2009 | Eli |
| 2009/0326611 | A1* | 12/2009 | Gillbe .......... 607/61 |
| 2010/0228308 | A1* | 9/2010 | Cowan et al. .......... 607/14 |

OTHER PUBLICATIONS

Beeby et al.; Energy harvesting vibration sources for microsystems applications; Meas Sci Technol; vol. 17; pp. R175-R195; 2006.

Cook-Chennault et al.; Powering MES portable devices—a review of non-regenerative and regenerative power supply systems special emphasis on piezoelectric energy harvesting systems; Smart Mater. Struct.; 17 (2008) 043001; 33 pgs.

Görge et al.; Microgenerators for energy autarkic pacemakers and defibrillators: fact or fiction?; Herz26; No. 1; pp. 64-68; 2000.

Hagood et al.; Development of micro-hydraulic transducer technology; Presented at the 10th Int'l. Conference on Adaptive Structures and Technologies; pp. 71-81; Oct. 11-13, 1999.

Häusler et al.; Implantable physiolocical power supply with PVDF film; Ferroelectrics; vol. 60; pp. 277-282; 1984.

Kornbluh et al.; Electroelastomers: Applications of Dielectric Elastomer Transducers for Actuation, Generation and Smart Structures; Proc. SPIE Smart Structures and Materials: Industrial and Commercial Applications of Smart Structures Technologies; 4698; pp. 254-270; 2002.

Mateu et al; Review of energy harvesting techniques and applications for microelectronics; Proceedings of the SPIE Microtechnologies for the New Millenium; 15 pgs.; 2005.

Mitcheson et al.; Analysis of Optimized Micro-Generator Architectures for Self-Powered Ubiquitous Computers; Adjunct Proc. UBICOMP 2002, 4th Int. Conf. Ubiquitous Computing; Gothenburg, Sweden; p. 5-6; Oct. 2002.

Mitcheson et al.; Architectures for Vibration-Driven Micropower Generators; J Microelectromechanical Systems; 13(3); pp. 429-440; Jun. 2004.

Mitcheson et al.; MEMS electrostatic micropower generator for low frequency operation; Sensors and Actuators A; vol. 115; pp. 523-529; 2004.

Morrow, D.; Microsensor for intramuscular pressure measurement (2003); Mayo Clinic; http://mayoresearch.mayo.edu/mayo/research/biomechanics/muscle_mech2cfm; (accessed: Oct. 19, 2009).

Myers et al.; Biologically-energized cardiac pacemaker; IEEE Transactions on Bio-Medical Electronics (letters to the Editor); vol. BME-10; No. 2; p. 83; Apr. 1963.

Paradiso; Energy harvesting for mobile computing (presentation); Responsive Environments Group, MIT Media Lab; 54 pgs.; Jun. 2005.

Platt; Electric power generation within orthopaedic implants using piezoelectric ceramics; Masters Thesis; 92 pgs.; 2003.

Reilly et al.; Thin film piezoelectric energy scavenging systems for long term medical monitoring; Proceedings of the Int'l Workshop on Wearable and Implantable Body Sensor Networks (BSN'06); pp. 38-41; Apr. 3-5, 2006.

Sjøgaard et al.; Intramuscular pressure and EMG relate during static contractions but dissociate with movement and fatigue; J Appl Physiol; vol. 96; pp. 1522-1529; 2004.

Teng et al.; Compressive loading on bone surfaces from muscular contraction: an in vivo study in the miniature pig, *Sus scrofa*; Journal of Morphology; vol. 238; pp. 71-80; 1998.

Torres et al.; Electrostatic energy harvester and Li-Ion charger circuit for micro-scale applications; MWSCAS '06, 49th IEEE Int'l. Midwest Symposium on Circuits and Systems; pp. 65-69; Aug. 6-9, 2006.

Pless, Benjamin; U.S. Appl. No. 12/545,618 entitled "Device for Energy Harvesting Within a Vessel,", filed Aug. 21, 2009.

Chicago (AFP); Extra heart energy can power pacemaker: researchers; Yahoo! News; Nov. 10, 2008.

SIMM Technology; Technology page; http://www.implantgen.org/technology.htm; printed Nov. 25, 2008.

Meninger S. et al; Vibration-to-Electric Energy Conversion; vol. 9; No. 1; pp. 64-76, Feb. 2001.

\* cited by examiner

DEVICES, METHODS, AND SYSTEMS FOR HARVESTING ENERGY IN THE BODY

CROSS REFERENCE TO RELATED APPLICATIONS

This application claims the benefit of priority of U.S. Provisional Patent Application Ser. No. 61/031,272 filed Feb. 25, 2008 titled "IMPLANTABLE POWER GENERATOR"; U.S. Provisional Patent Application Ser. No. 61/125,855 filed Apr. 26, 2008 titled "LIQUID CAPACITIVE ELECTRICAL GENERATOR"; U.S. Provisional Patent Application Ser. No. 61/081,261 filed Jul. 16, 2008 titled "ENERGY HARVESTING WITH DIELECTRIC PHASE CHANGE"; U.S. Provisional Patent Application Ser. No. 61/093,988 filed Sep. 3, 2008 titled "TRANSMISSION OF HARVESTED ENERGY IN THE BODY"; U.S. Provisional Patent Application Ser. No. 61/096,259 filed Sep. 11, 2008 titled "MEDICAL DEVICES UTILIZING IMPLANTABLE POWER GENERATOR"; and U.S. Provisional Patent Application Ser. No. 61/098,688 filed Sep. 19, 2008 titled "ELECTROMAGNETIC IMPLANTABLE ENERGY HARVESTER"; each of which are incorporated herein by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

This invention relates generally to the power generation field, and more specifically to new and useful devices, methods, and systems for harvesting energy.

BACKGROUND OF THE INVENTION

Implantable medical devices, such as implantable pulse generators like spinal cord stimulators or pacemakers, require a power supply to generate a pulse or stimulation. Conventional spinal cord stimulators typically have either large batteries that are uncomfortable for the patient, or smaller batteries that require frequent recharging. Additionally, for example, conventional Cardiac Resynchronization Therapy (CRT) Implantable Cardioverter Defibrillators (ICDS) stimulate the heart frequently and as a result have a high current drain from the battery and typically only last a few years before they need to be replaced due to battery depletion.

Thus there is a need in the implantable medical devices field for an alternative source of power for these devices, allowing these devices to be smaller and/or not require recharging or frequent recharging. Such improvements might significantly increase the longevity of these implantable medical devices resulting in improved patient care and reduced cost.

The various illustrative embodiments described herein provide an alternative source of power for these devices or other suitable devices or machines. Described herein are new and useful devices, methods, and systems for harvesting energy.

SUMMARY OF THE INVENTION

An aspect of the invention includes an implantable power generator for converting mechanical energy from a patient to electrical energy. In some embodiments the power generator includes a compressible element adapted and configured to be placed between two adjacent tissue layers of the patient and to be compressed by a force applied from the two adjacent tissue layers to the compressible element, and a transducer, coupled to the compressible element, that converts mechanical energy from the compression of the compressible element to electrical energy. In some embodiments, the force applied from the two adjacent tissue layers to the compressible element, compresses the compressible element a distance greater than 10 µm.

In some embodiments, the compressible element includes a base adapted and configured to be coupled to the first tissue layer, and a moveable surface, substantially opposite to the base, adapted and configured to be coupled to the second tissue layer. In some embodiments, the force applied from the two adjacent tissue layers to the compressible element moves the movable surface with respect to the base. In some embodiments, the base is a substantially rigid surface and the moveable surface is a flexible surface and in some embodiments, the moveable surface includes a piston head. In some embodiments, the base includes a second movable surface, such that both the first and second moveable surfaces are flexible.

In some embodiments, the compressible element defines a chamber and includes a fluid within the chamber. In some embodiments, upon compression of the compressible element, the compressible element displaces the fluid from within the chamber of the compressible element, thereby generating a fluid pressure. In some embodiments, the power generator further includes a transmission, coupled to the compressible element and to the transducer, which transforms a motion from the compression of the compressible element into a rotational motion. In some embodiments, the transmission further includes a wheel that transforms a fluid pressure from the compression of the compressible element into a rotational motion. In some embodiments, the transmission includes a rack and a pinion that transforms the motion from the compression of the compressible element into a rotational motion. In some embodiments, the transmission includes a threaded spindle and a threaded cylinder, coupled to the threaded spindle, that transforms the motion from the compression of the compressible element into a rotational motion. In some embodiments, the transducer includes an electromagnetic generator coupled to the transmission and in some embodiments, the rotational motion from the transmission drives the electromagnetic generator, such that the electromagnetic generator converts the rotational motion to electrical energy.

In some embodiments, the transducer includes a capacitor having a first plate and a second plate, wherein the plates have a first voltage across them when they are positioned a first distance from one another, and have a second voltage across them when they positioned a second distance from one another. In some embodiments, the fluid pressure generated by the compressible element separates the first plate from the second plate, such that the plates move from the first distance to the second distance. In some embodiments, the first distance is less than the second distance, and the first voltage is less than the second voltage.

In some embodiments, the transducer includes a capacitor within the chamber, having a first plate and a second plate, the fluid is a phase changing dielectric fluid, and the plates have a first voltage across them when the dielectric fluid is in a first phase and have a second voltage across them when the dielectric fluid is in a second phase. In some embodiments, the compressible element includes a base adapted and configured to be coupled to the first tissue layer and a moveable surface, substantially opposite to the base, adapted and configured to be coupled to the second tissue layer. In some embodiments, the base and the movable surface define the volume of the chamber and the force applied from the two adjacent tissue layers to the compressible element moves the movable surface with respect to the base, such that the volume of the phase changing dielectric fluid is changed and the phase changing dielectric fluid transitions between the first phase with a first dielectric constant and the second phase with a second dielectric constant.

In some embodiments, the implantable power generator further includes a circuit that collects electrical energy from the capacitor as the voltage transitions from the first voltage to the second voltage, and in some embodiments, the circuit further functions to apply a voltage to the plates when the dielectric fluid is in the first phase.

In some embodiments, the first phase of the dielectric fluid is a gas phase and the second phase is a liquid phase. In some embodiment, the ratio of second dielectric constant to first dielectric constant is greater than 5, while in some embodiments, the ratio of second dielectric constant to first dielectric constant is greater than 20. In some embodiments, the phase changing dielectric fluid is water.

In some embodiments, the base is a substantially rigid surface and the moveable surface includes a piston head. In some embodiments, the movable surface defines a first chamber and a second chamber within the housing, and the capacitor is within the second chamber.

In some embodiments, the transducer includes a capacitor within the chamber, having a first plate and a second plate, wherein the fluid is a dielectric fluid and the plates have a first voltage across them when a first amount of the dielectric fluid is between the insulator and the second plate, and have a second voltage across them when a second amount of the dielectric fluid is between the insulator and the second plate. In some embodiments, the compressible element includes a moveable surface and the capacitor includes an insulator coupled to the first plate and disposed between the first plate and the second plate, wherein at least one plate is coupled to the movable surface, and wherein the force applied from the two adjacent tissue layers to the compressible element moves the movable surface from a first position toward a second position and displaces the dielectric fluid such that the first amount of the dielectric fluid is greater than the second amount of the dielectric fluid.

In some embodiments, the compressible element includes a flexible housing and a structural member, coupled to the housing and to the transducer, that transmits a force from the housing to the transducer such that, upon compression of the compressible element, the housing compresses and the structural member applies a tension force to the transducer. In some embodiments, the transducer includes an electroactive polymer, coupled to the structural member, which has a first capacitance in a first thickness and a second capacitance in a second thickness. In some embodiments, the structural member includes three substantially rigid members, disposed within the housing, wherein upon compression of the compressible element, the housing compresses and the structural member transitions from a triangular arrangement having a first perimeter to a substantially horizontal arrangement having a second perimeter.

In some embodiments, the transducer is coupled to the structural member such that upon compression of the compressible element, the structural member applies a tension force to the transducer, and such that the transducer transitions from a first perimeter to a second perimeter. In some embodiments, the transducer includes an electroactive polymer that has a first capacitance in the first perimeter and a second capacitance in the second perimeter. In some embodiments, the transducer includes a piezoelectric material, such that upon compression of the compressible element, the piezoelectric material flexes.

In some embodiments, the force applied from the two adjacent tissue layers to the compressible element is generated by the patient applying an external force to the compressible element. In some embodiments, the two adjacent tissue layers are adjacent layers of a muscle of a patient and in some embodiments, the force applied from the two adjacent tissue layers to the compressible element is generated by the muscle contracting. In some embodiments, the two adjacent tissue layers are adjacent layers of tissue within a muscle bundle, while in some embodiments, the two adjacent tissue layers are two adjacent muscle bundles. In some embodiments, the first tissue layer is a muscle layer, and the second tissue layer is a firm tissue layer. In some embodiments, the force applied from the two adjacent tissue layers to the compressible element is generated by the muscle contracting and applying a force to the compressible element against the firm tissue layer.

In some embodiments, the implantable power generator includes a storage device, coupled to the transducer that collects energy generated by the transducer, and in some embodiments, the storage device conditions the electrical energy for use by powered device. In some embodiments, the implantable power generator includes a housing that encloses at least one of the compressible element and the transducer, separating them from the adjacent tissue layers.

Another aspect of the invention includes an implantable power generator for converting mechanical energy from within a muscle of a patient to electrical energy. In some embodiments, the generator includes a compressible element adapted and configured to be placed between two adjacent muscle layers of the muscle and to be compressed by a pressure generated by the muscle contracting; and a transducer, coupled to the compressible element, that converts mechanical energy from the compression of the compressible element to electrical energy. In some embodiments, the compressible element includes a base adapted and configured to be coupled to the first muscle layer; and a moveable surface, substantially opposite to the base, adapted and configured to be coupled to the second muscle layer. In some embodiments, the pressure generated by the muscle contracting moves the movable surface with respect to the base.

In some embodiments, the compressible element, having a movable surface, defines a chamber and further includes a dielectric fluid within the chamber, and in some embodiments, the transducer includes a capacitor within the chamber of the housing, and in some embodiments, the capacitor includes a first and second plate, and an insulator coupled to the first plate and disposed between the first plate and the second plate, wherein at least one plate is coupled to a movable surface of the housing. In some embodiments, the plates have a first voltage across them when a first amount of the dielectric fluid is between the insulator and the second plate, and have a second voltage across them when a second amount of the dielectric fluid is between the insulator and the second plate, and the movable surface moves from a first position toward a second position and displaces the dielectric fluid such that the first amount of the dielectric fluid is greater than the second amount of the dielectric fluid. In some embodiments, the movable surface is moved from a first position toward a second position by the pressure generated by the muscle contracting, while in some embodiments, upon release of the muscle contraction, a negative pressure is returns the movable surface to the first position.

Another aspect of the invention includes an implantable power generator for converting mechanical energy from a muscle within a patient to electrical energy. In some embodiments, the generator includes a compressible element adapted and configured to be placed between a muscle layer and an adjacent firm tissue layer of the patient and to be compressed by a pressure generated by the muscle contracting adjacent to the firm tissue layer, and a transducer, coupled to the compressible element, that converts mechanical energy from the compression of the compressible element to electrical energy.

In some embodiments, the compressible element includes a base adapted and configured to be coupled to the firm tissue layer, and a moveable surface, substantially opposite to the base, adapted and configured to be coupled to the muscle layer. While in some embodiments, the pressure generated by the muscle contracting against the firm tissue layer moves the movable surface with respect to the base.

Another aspect of the invention is a power generator for converting mechanical energy to electrical energy. In some embodiments, the generator includes a housing that defines a chamber, a phase changing dielectric fluid contained within the chamber of the housing, a moveable surface coupled to the housing that defines the volume of the phase changing dielectric fluid. In some embodiments, as the moveable surface moves from a first position toward a second position, the volume of the phase changing dielectric fluid is changed, and the phase changing dielectric fluid transitions between a first phase with a first dielectric constant and a second phase with a second dielectric constant. In some embodiments, the power generator also includes a capacitor within the chamber of the housing, and in some embodiments, the capacitor includes a first plate and a second plate that define a fluid space between them that contains a portion of the phase changing dielectric fluid, and the plates have a first voltage across them when the dielectric fluid is in the first phase and have a second voltage across them when the dielectric fluid is in the second phase.

In some embodiments, the housing includes a spring element that biases the movable surface toward the first position. In some embodiments, the moveable surface includes a flexible surface, and in some embodiments it includes a bellows. In some embodiments, the housing includes a base, substantially opposite to the movable surface, wherein the moveable surface moves relative to the base. In some embodiments, the base is adapted and configured to be coupled to a first tissue layer of a patient, and the moveable surface is adapted and configured to be coupled to a second adjacent tissue layer of a patient, wherein a force applied from the two adjacent tissue layers to the housing moves the movable surface with respect to the base and reduces the volume of the chamber. In some embodiments, the first tissue layer is a firm tissue layer, the second tissue layer is a muscle layer, and the force applied to the housing is generated by the muscle contracting adjacent to the firm tissue layer. In some embodiments, the first and second tissue layers are muscle layers within a muscle and the force applied to the housing is generated by the muscle contracting. In some embodiments, the base is a substantially rigid surface and the moveable surface includes a piston head. In some embodiments, the movable surface defines first chamber and a second chamber within the housing and the capacitor is within the second chamber.

In some embodiments, the power generator includes a circuit that collects electrical energy from the capacitor as the voltage transitions from the first voltage to the second voltage, and in some embodiments, the circuit further functions to apply a voltage to the plates when the dielectric fluid is in the first phase.

In some embodiments, the first phase of the dielectric fluid is a gas phase and the second phase is a liquid phase. In some embodiments, the ratio of second dielectric constant to first dielectric constant is greater than 5, while in some embodiments, the ratio of second dielectric constant to first dielectric constant is greater than 20. In some embodiments, the first phase is a gas phase and the second phase is a solid phase. In some embodiments, the first phase is a liquid phase and the second phase is a solid phase. In some embodiments, the phase changing dielectric fluid is water.

In some embodiments, the plates include a surface treated to facilitate a phase change of the dielectric fluid. In some embodiments, the capacitor includes a non-conductive spacer between the plates, and in some embodiments, the non-conductive spacer is a porous material disposed between the two plates.

Another aspect of the invention includes a power generator for converting mechanical energy to electrical energy. In some embodiments, the generator includes a housing that defines a chamber and includes a movable surface, a dielectric fluid contained within the chamber of the housing, and a capacitor within the chamber of the housing. In some embodiments, the capacitor includes a first and second plate, and an insulator coupled to the first plate and disposed between the first plate and the second plate. In some embodiments, at least one plate is coupled to a movable surface of the housing, the plates have a first voltage across them when a first amount of the dielectric fluid is between the insulator and the second plate, and have a second voltage across them when a second amount of the dielectric fluid is between the insulator and the second plate. In some embodiments, the movable surface moves from a first position toward a second position and displaces the dielectric fluid such that the first amount of the dielectric fluid is greater than the second amount of the dielectric fluid.

In some embodiments, the movable surface moves from a first position toward a second position by a force applied to the housing. In some embodiments, the plates have a first voltage across them when they are positioned a first distance from one another, and have a second voltage across them when they positioned a second distance from one another. In some embodiments, the movable surface moves at least one plate with respect to the other plate such that the plates move from the first distance from one another to the second distance from one another. In some embodiments, the first distance is greater than the second distance, and the first voltage is greater than the second voltage.

In some embodiments, the power generator includes a circuit that collects electrical energy from the capacitor as the voltage transitions from the second voltage to the first voltage. In some embodiments, the circuit further functions to apply a voltage to the plates when the second amount of the dielectric fluid is between the insulator and the second plate.

In some embodiments, the housing includes a flexible membrane. In some embodiments, the housing includes a second movable surface. In some embodiments, the housing includes a spring element that returns the movable surface to the first position. In some embodiments, the spring element includes a compliant portion coupled to the housing, and a non-compliant portion, coupled to the compliant portion, wherein the non-compliant portion and the compliant portion define a fluid filled chamber. In some embodiments, as a force is applied to the housing and the movable surface displaces the dielectric fluid, the dielectric fluid moves a portion of the compliant portion into the fluid filled chamber, thereby compressing the fluid in the chamber. In some embodiments, when the force is no longer applied to the housing, the fluid in the chamber moves the portion of the compliant portion out of the fluid filled chamber, thereby replacing dielectric fluid between the insulator and the second plate. In some embodiments, the capacitor has a first capacitance when the first amount of the dielectric fluid is between the insulator and the second plate, and has a second capacitance when the second amount of the dielectric fluid is between the insulator and the second plate.

In some embodiments, the first capacitance is less than the second capacitance, and in some embodiments, the capacitor has the second capacitance when the second plate contacts the insulator. In some embodiments, the first plate defines an aperture through which the dielectric fluid flows. In some embodiments, the dielectric constant of the insulator is higher than the dielectric constant of the dielectric fluid.

In some embodiments, the housing includes a base, substantially opposite to the movable surface, wherein the moveable surface moves relative to the base. In some embodiments, the base is adapted and configured to be coupled to a first tissue layer of a patient, and the moveable surface is adapted and configured to be coupled to a second adjacent tissue layer of a patient, wherein a force applied from the two adjacent tissue layers to the housing moves the movable surface from the first position toward the second position with respect to the base. In some embodiments, the first tissue layer is a firm tissue layer, the second tissue layer is a muscle layer, and the force applied to the housing is generated by the muscle contracting adjacent to the firm tissue layer. In some embodiments, the first and second tissue layers are muscle layers within a muscle and the force applied to the housing is generated by the muscle contracting. In some embodiments, upon release of the muscle contraction, a force is applied to the housing that returns the movable surface to the first position.

Another aspect of the invention includes a method for generating power by converting mechanical energy from a patient to electrical energy. In some embodiments, the method includes the steps of positioning a compressible element of an implantable power generator in an anatomical site within the patient, the anatomical site defined by a first tissue layer and a second, opposite tissue layer, receiving a pressure applied by the two adjacent tissue layers with the compressible element thereby compressing the compressible element, and converting mechanical energy from the compression of the compressible element to electrical energy. In some embodiments, the positioning step includes positioning the compressible element between a firm tissue layer and a muscle layer. In some embodiments, the receiving step includes receiving a pressure generated by the muscle contracting adjacent to the firm tissue layer. In some embodiments, the positioning step includes positioning the compressible element between a temporalis bone and a temporalis muscle, while in some embodiments, the positioning step includes positioning the compressible element such that a surface of the compressible element is supported by the temporal fossa. In some embodiments, the positioning step includes positioning the compressible element through an incision in the patient, such that the structural integrity of the muscle that connects the coronoid process of the mandible to the superior temporalis line is maintained.

In some embodiments, the positioning step includes positioning the compressible element between muscle layers within a muscle. In some embodiments, the positioning step includes positioning the compressible element in a temporalis muscle. In some embodiments, the positioning step includes positioning the compressible element in a pectoral muscle, while in some embodiments, the positioning step includes positioning the compressible element in a gluteus maximus muscle. In some embodiments, the receiving step includes receiving a pressure generated by the muscle contracting. In some embodiments, the method further includes the step of storing the electrical energy, and in some embodiments, the method further includes the step of powering a medical device with the electrical energy. In some embodiments, the receiving step includes moving a movable surface with respect to a base surface of the compressible element, thereby compressing the compressible element.

Another aspect of the invention includes a system for powering a medical device. In some embodiments, the system includes an implantable power generator for converting mechanical energy from a patient to electrical energy. In some embodiments, the generator includes a compressible element adapted and configured to be placed between two adjacent tissue layers of the patient and to be compressed by a force applied from the two adjacent tissue layers to the compressible element, and a transducer, coupled to the compressible element, that converts mechanical energy from the compression of the compressible element to electrical energy. In some embodiments, the power generator further includes a storage device that collects electrical energy from the transducer and a medical device coupled to the storage device that receives electrical energy from the storage device.

In some embodiments, the two adjacent tissue layers comprise a firm tissue layer and a muscle layer and the force applied to the compressible element is generated by the muscle contracting adjacent to the firm tissue layer. In some embodiments, the two adjacent tissue layers are muscle layers within a muscle and the force applied to the compressible element is generated by the muscle contracting. In some embodiments, the system further includes a circuit coupled to the transducer that conditions the electrical energy. In some embodiments, the circuit includes a diode bridge, and in some embodiments the circuit includes a buck boost circuit.

In some embodiments, the storage device is a capacitor, while in some embodiments, the storage device is a battery. In some embodiments, the storage device provides energy to the medical device continuously.

In some embodiments, the system includes a transmitter that couples the storage device to the medical device and transmits electrical energy from the storage device to the medical device. In some embodiments, the transmitter transforms the electrical energy into a suitable form for transmission to the medical device, while in some embodiments, the transmitter transmits energy from the storage device to the medical device through a wire. In some embodiments, the transmitter includes an antenna and the transmitter transmits the energy in the form of electromagnetic radiation. In some embodiments, the transmitter includes an infrared light source and the transmitter transmits the energy in the form of infrared light. In some embodiments, the transmitter includes an ultrasound transducer and the transmitter transmits the energy in the form of ultrasound. In some embodiments, the transmitter includes tissue contact electrodes and the transmitter transmits the energy in the form of electricity conducted through the body.

In some embodiments, the system includes a second circuit coupled to the medical device that conditions the electrical energy. In some embodiments, the system includes a receiver that couples the storage device to the medical device and receives electrical energy from the storage device. In some embodiments, the receiver includes an antenna and the receiver receives the energy in the form of electromagnetic radiation. In some embodiments, the receiver includes an infrared light receiver and the receiver receives the energy in the form of infrared light. In some embodiments, the receiver includes an ultrasound receiver and the receiver receives the energy in the form of ultrasound. In some embodiments, the receiver includes tissue contact electrodes and the receiver receives the energy in the form of electricity conducted through the body.

In some embodiments, the system includes a second storage device, coupled to the medical device that that collects electrical energy from the first storage device. In some embodiments, the second storage device is a bypass capacitor.

In some embodiments, the medical device is a pulse generator. In some embodiments, the medical device is a neurostimulator. In some embodiments, the medical device is sized and configured to be implanted in the head of the patient, adjacent to the sphenopalatine ganglion (SPG). In some embodiments, the compressible element is sized and configured to be implanted in the head of the patient, under or within the temporalis muscle. In some embodiments, the medical device receives electrical energy from the storage device to electrically stimulate the SPG.

In some embodiments, the medical device is a pacemaker. In some embodiments, the medical device is sized and configured to be implanted in the torso of the patient, adjacent to the heart. In some embodiments, the compressible element is sized and configured to be implanted in the torso of the patient, under or within the pectoral muscle. In some embodiments, the medical device receives electrical energy from the storage device to electrically stimulate the heart.

Another aspect of the invention includes a system for powering a medical device. In some embodiments, the system includes an implantable power generator for converting mechanical energy from a patient to electrical energy. In some embodiments, the generator includes a compressible element adapted and configured to be placed between two adjacent tissue layers of the patient and to be compressed by a force applied from the two adjacent tissue layers to the compressible element, and a transducer, coupled to the compressible element, that converts mechanical energy from the compression of the compressible element to electrical energy. In some embodiments, the system further includes a storage device that collects electrical energy from the transducer, an auxiliary power supply, and a medical device coupled to at least one of the storage device and the auxiliary power supply that receives electrical energy from at least one of the storage device and the auxiliary power supply.

In some embodiments, the two adjacent tissue layers comprise a firm tissue layer and a muscle layer and the force applied to the compressible element is generated by the muscle contracting adjacent to the firm tissue layer. In some embodiments, the two adjacent tissue layers are muscle layers within a muscle and the force applied to the compressible element is generated by the muscle contracting.

In some embodiments, the system further includes a circuit coupled to the transducer that conditions the electrical energy. In some embodiments, the circuit includes a diode bridge. In some embodiments, the circuit includes a buck boost circuit. In some embodiments, the storage device is a capacitor. In some embodiments, the storage device is a battery. In some embodiments, the storage device provides energy to the medical device continuously.

In some embodiments, the auxiliary power supply is a capacitor. In some embodiments, the auxiliary power supply is a battery. In some embodiments, the auxiliary power supply provides energy to the medical device continuously In some embodiments, the auxiliary power supply is not implanted within the patient. In some embodiments, the auxiliary power supply provides energy to the medical device when the auxiliary power supply is adjacent to the medical device. In some embodiments, the auxiliary power supply provides energy to the medical device when medical device requests energy from the auxiliary power supply. In some embodiments, the auxiliary power supply provides energy to the medical device when medical device requests energy from the storage device, and the storage device does not have sufficient electrical energy to power the medical device.

In some embodiments, the system further includes a transmitter that couples the auxiliary power supply to the medical device and transmits electrical energy from the auxiliary power supply to the medical device. In some embodiments, the transmitter transforms the electrical energy into a suitable form for transmission to the medical device In some embodiments, the transmitter transmits energy from the storage device to the medical device through a wire. In some embodiments, the transmitter includes an antenna and the transmitter transmits the energy in the form of electromagnetic radiation. In some embodiments, the transmitter includes an infrared light source and the transmitter transmits the energy in the form of infrared light. In some embodiments, the transmitter includes an ultrasound transducer and the transmitter transmits the energy in the form of ultrasound. In some embodiments, the transmitter includes tissue contact electrodes and the transmitter transmits the energy in the form of electricity conducted through the body.

In some embodiments, the system further includes a second circuit coupled to the medical device that conditions the electrical energy. In some embodiments, the system further includes a receiver that couples the auxiliary power supply to the medical device and receives electrical energy from the auxiliary power supply. In some embodiments, the receiver includes an antenna and the receiver receives the energy in the form of electromagnetic radiation. In some embodiments, the receiver includes an infrared light receiver and the receiver receives the energy in the form of infrared light. In some embodiments, the receiver includes an ultrasound receiver and the receiver receives the energy in the form of ultrasound. In some embodiments, the receiver includes tissue contact electrodes and the receiver receives the energy in the form of electricity conducted through the body.

In some embodiments, the system further includes a second storage device, coupled to the medical device that that collects electrical energy from the auxiliary power supply. In some embodiments, the second storage device is a bypass capacitor.

In some embodiments, the medical device is a pulse generator. In some embodiments, the medical device is a neurostimulator. In some embodiments, the medical device is sized and configured to be implanted in the head of the patient, adjacent to the sphenopalatine ganglion (SPG). In some embodiments, the compressible element is sized and configured to be implanted in the head of the patient, under or within the temporalis muscle. In some embodiments, the medical device receives electrical energy from at least one of the storage device and the auxiliary power supply to electrically stimulate the SPG. In some embodiments, the medical device receives electrical energy from the auxiliary power supply when the auxiliary power supply is placed adjacent to the head of the patient.

In some embodiments, the medical device is a pacemaker. In some embodiments, the medical device is sized and configured to be implanted in the torso of the patient, adjacent to the heart. In some embodiments, the compressible element is sized and configured to be implanted in the torso of the patient, under or within the pectoral muscle. In some embodiments, the medical device receives electrical energy from at least one of the storage device and the auxiliary power supply to electrically stimulate the heart. In some embodiments, the medical device receives electrical energy from the auxiliary power supply when the auxiliary power supply is placed adjacent to the heart of the patient.

Another aspect of the invention includes a method for generating power. In some embodiments, the method includes the step of positioning a capacitor in a phase changing dielectric fluid contained within a chamber. In some embodiments, the capacitor includes a first plate and a second plate that define a space between them that contains a portion of the phase changing dielectric fluid. In some embodiments, the method further includes the steps of applying a first voltage to at least one of the plates of the capacitor, changing the phase of the phase changing dielectric fluid such that it transitions at least in part between a first phase with a first dielectric constant and a second phase with a second dielectric constant, and collecting a second voltage from at least one of the plates of the capacitor, wherein the plates of the capacitor have the second voltage across them when the dielectric fluid is in the second phase.

In some embodiments, the changing step further includes changing the pressure of the phase changing dielectric fluid such that the phase changing dielectric fluid transitions at least in part between a first phase and a second phase. In some embodiments, the changing step further includes applying a mechanical input to change the pressure of the phase changing dielectric fluid. In some embodiments, the changing step further includes changing the temperature of the phase changing dielectric fluid such that the phase changing dielectric fluid transitions at least in part between a first phase and a second phase. In some embodiments, the changing step further includes changing the volume of the phase changing dielectric fluid such that the phase changing dielectric fluid transitions at least in part between a first phase and a second phase. In some embodiments, the changing step further includes applying a mechanical input to change the volume of the phase changing dielectric fluid. In some embodiments, the changing step further includes applying an ultrasound signal to the phase changing dielectric fluid to change the phase of the phase changing dielectric fluid. In some embodiments, the changing step further includes applying radiofrequency signal to the phase changing dielectric fluid to change the phase of the phase changing dielectric fluid. In some embodiments, the changing step further includes applying a laser to the phase changing dielectric fluid to change the phase of the phase changing dielectric fluid.

In some embodiments, the changing step further includes changing the phase of the dielectric fluid such that it transitions at least in part between a gas phase and a liquid phase. In some embodiments, the changing step further includes changing the phase of the dielectric fluid such that it transitions at least in part between a gas phase and a solid phase. In some embodiments, the changing step further includes changing the phase of the dielectric fluid such that it transitions at least in part between a liquid phase and a solid phase.

DETAILED DESCRIPTION OF THE INVENTION

Figure 1A:
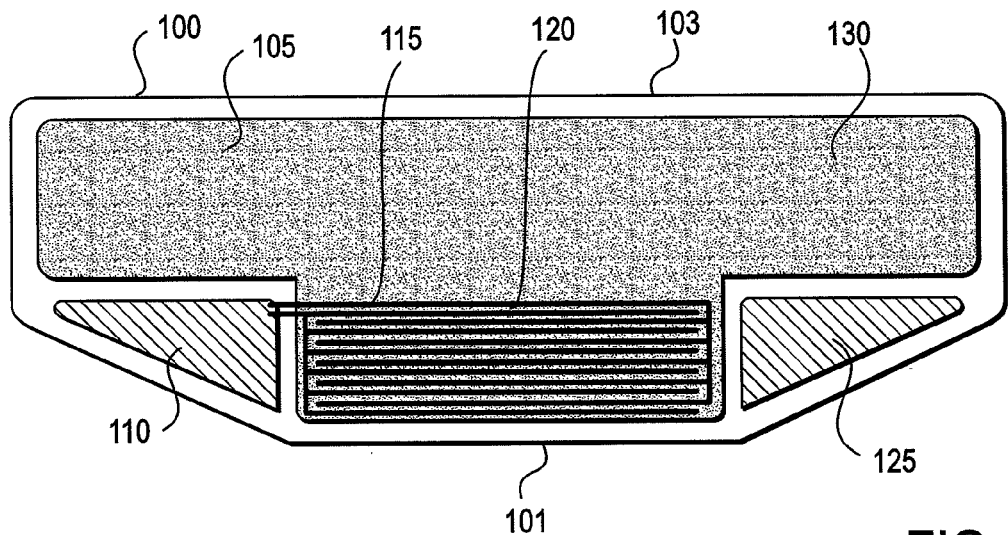
FIGS. 1A-1B are drawings of a first embodiment of the power generator that includes a capacitor and a phase changing dielectric fluid.

The following description of the various illustrative embodiments of the invention are not intended to limit the invention to these illustrative embodiments, but rather to enable any person skilled in the art to make and use this invention.

In some illustrative embodiments of the invention, a power generator for converting mechanical energy to electrical energy is described. The power generator may include a compressible element adapted and configured to be placed in an environment having a variable compressive force such as varying ambient pressures. The compressible element may be compressed by a force applied by the variable pressure to the compressible element. The power generator may further include a transducer that may be coupled to the compressible element and that may convert mechanical energy from the compression of the compressible element to electrical energy.

In some embodiments, the power generator may be implanted into a patient (such as a human or other mammal), worn by a patient, or otherwise coupled to a patient, and the electrical energy generated by the power generator may be used to power a medical device and, more specifically, to power an implantable medical device such as a neurostimulator or a cardiac pacemaker. In some embodiments, the power generator may be manually activated by the patient or caregiver by manually manipulating by pressing, squeezing, or otherwise applying a force to the compressible element to compress the compressible element and activate the power generator as needed. Alternatively, an external device that may manipulate by pressing, squeezing, or otherwise apply a force that compresses the compressible element and activate the power generator as needed, may be held up or coupled to the patient externally.

The force that creates a movement from which electrical energy can be converted is not limited to forces generated by humans and other mammals, however, and in some embodiments, the power generator may be adapted for environmental energy harvesting. In environmental energy harvesting the compressive forces imparted to the power generator is provided from a renewable and/or environmental source such as, for example, wind power, tidal power, solar power and the like. Additionally, the compressive forces may come from industrial and/or mechanical sources. In this aspect, the power generator may be incorporated into existing industrial systems to capture equipment and/or component compressive forces and generate electrical energy.

The various embodiments of the power generators as described may be alternatively used in any other suitable environments and for any suitable reasons.

Power Generators

The power generator including a compressible element and a transducer is preferably one of several embodiments. As described below, some illustrative embodiments of the invention include various embodiments having electrostatic transducers and various embodiments having electromechanical transducers. The generator may alternatively include any other suitable transducer(s).

In the various embodiments having electrostatic transducers, the transducer includes a capacitor and the compression of the compressible element initiates a change in capacitance of the capacitor. In these embodiments, electrical energy is generated in the form of the voltage and/or charge on plates of the capacitor, as the capacitance between these plates changes. For example, the capacitance of the capacitor may change due to a phase change of dielectric fluid (for example, the first and second embodiments, as shown in, FIGS. 1-2), due to a change in the distance between the plates (for example, the third and fourth embodiments, as shown in, FIGS. 3A-3B and 11-12, respectively), due to a change in the amount of dielectric fluid between the plates (for example, the third embodiment as shown in, FIGS. 3A and 3B), and/or due to any other mechanism.

In the various embodiments having electromechanical transducers, the compression of the compressible element activates the transducer such that it may convert the mechanical energy from the compression of the compressible element to electrical energy. For example, the transducer may include a material such as an electroactive polymer that may be stretched by the compression of the compressible element (for example, the fifth and sixth embodiments, as shown in, FIGS. 4A-6C), the transducer may include a material such as a piezoelectric material that may be flexed or bent by the compression of the compressible element, (for example, the seventh and eighth embodiments, as shown in, FIGS. 7A-10), and/or the transducer may include an electromagnetic generator actuated by the compression of the compressible element, (for example, the ninth through eleventh embodiments, as shown in, FIGS. 13A-15).

The power generator may alternatively include any other suitable compressible element and transducers and may alternatively have any other suitable configurations, arrangements, etc. of those components or any other additional components.

Power Generators—Exemplary Electrostatic Embodiments

Figure 1B:
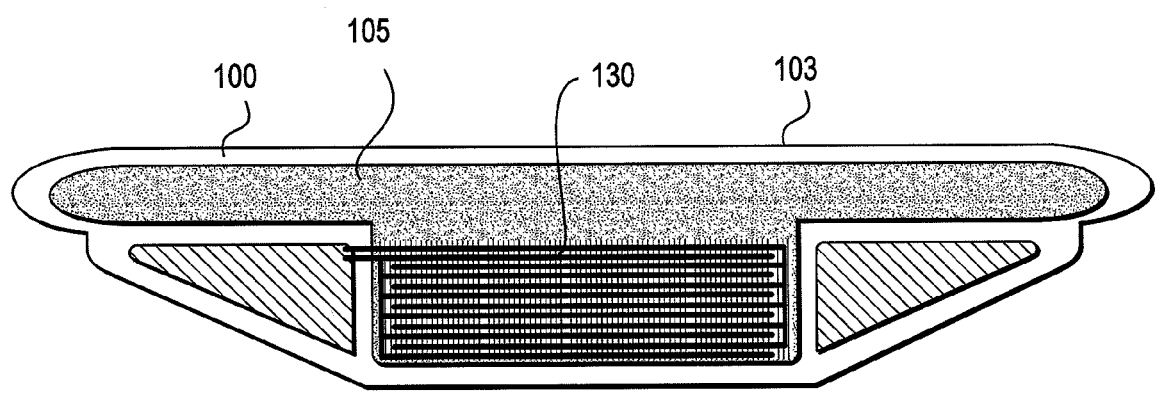

FIG. 1A shows a power generator of a first embodiment. The power generator as shown in FIG. 1A includes a housing 100 that defines a chamber 105. There is a capacitor 115 and a phase changing dielectric fluid 130 in the chamber. The capacitor has two plates having a space 120 between them that is in fluid communication with the fluid 130 in the rest of the chamber. The housing includes portion 103 that moves with respect to portion 101, such that, as shown in FIG. 1B, the housing is compressible. As the housing 100 is compressed, the volume of the fluid 130 is reduced, and the fluid changes phases. The capacitance of the capacitor changes as the phase changes, and electrical energy is generated in the form of the voltage and/or charge on plates of the capacitor, as the capacitance between these plates changes.

In the first embodiment, as shown in FIGS. 1A and 1B, the power generator for converting any suitable form of mechanical energy to electrical energy includes a housing 100 that defines a chamber 105, a phase changing dielectric fluid 130 contained within the chamber of the housing, a moveable surface 103 coupled to the housing that defines the volume of the phase changing dielectric fluid, and a capacitor 115 within the chamber of the housing. The capacitor includes a first plate and a second plate that do not touch each other and that define a fluid space 120 between them containing a portion of the phase changing dielectric fluid. The term fluid is used to refer inclusively to liquid and/or gas phases. As shown in FIG. 1B, as the volume of the phase changing dielectric fluid is changed by the movement of the movable surface, the phase changing dielectric fluid transitions between a first phase with a first dielectric constant, and a second phase with a second dielectric constant. In operation, it may be that only a portion of the dielectric fluid may transition between a first phase and a second phase. The plates of the capacitor have a first voltage across them when the dielectric fluid is in the first phase and have a second voltage across them when the dielectric fluid is in the second phase. In some variations, the housing includes a base 101 substantially opposite to the moveable surface. As shown in FIGS. 1A and 1B, the base and the moveable surface, and their position relative to one another, define the volume of the phase changing dielectric fluid. In some embodiments, the base and the movable surface of the housing form an enclosure that may enclose components of the power generator.

In this first embodiment, the phase changing dielectric fluid transitions between a first phase with a first dielectric constant, and a second phase with a second dielectric constant. In some variations, the dielectric fluid may cycle between a liquid phase and a gas phase as a result of mechanical input or other input such as thermal energy or other energy. In some embodiments, when the dielectric is in a liquid phase its dielectric constant is higher than when the dielectric is in a gas phase. It can be seen from the equation $$C = \varepsilon_r \varepsilon_0 \frac{A}{d} \qquad \text{(Equation 1)}$$

where A is the area of each plate, $\varepsilon_r$ is the dielectric constant (also known as relative static permittivity) of the material between the plates, and $\varepsilon_0$ is the permittivity of free space, or $8.854 \times 10^{12}$ F/m) that decreasing $\varepsilon_r$, the dielectric constant, will lower the capacitance C. By the well-known equation $$C = Q/V \qquad \text{(Equation 2)}$$

it can also be seen that the voltage, V, will increase as the capacitance C decreases, if a constant charge Q is held on the plates. Using this principle, in this embodiment, the mechanical energy used to decrease $\varepsilon_r$, the dielectric constant, can be converted to electrical energy stored on the capacitor, and this energy may be collected. In this embodiment, the dielectric constant is changed by changing the phase of the dielectric fluid (i.e., liquid versus gas). In some variations, the energy source to change the phase of the dielectric fluid may be cyclic thermal variation, meaning that the temperature is raised and lowered cyclically to induce the phase change cycle (liquid to gas and back to liquid, for example). It is also anticipated that other forms of energy such as (without limitation) ultrasound, laser, and radiofrequency may also be used to change the phase of the dielectric fluid. In addition to dielectrics having phase changes between liquid and gas, it is anticipated that phase changes between gas and solid as well as phase changes between liquid and solid may also be advantageously employed. In addition dielectric phase changes from one configuration of solid to another, or from one liquid configuration to another may also be used in the invention. The particular phase change to be employed will depend upon a number of factors such as the dielectric material being used and the operating environment of the power generator, for example.

Referring again to FIG. 1A, in the first embodiment, the power generator includes a housing 100 that defines a chamber 105. In some embodiments, the housing may further function to provide an additional protective layer to ensure biocompatibility of the device. In some variations, the housing includes an impermeable wall 100 that forms the shell of the power generator, and is impermeable to the dielectric fluid chosen. The impermeable wall may be made of an unlayered material such as titanium, or may be constructed of several layers (not shown). For example, a relatively soft, biocompatible material such as silicone rubber may be chosen as the outermost layer. In some embodiments, the housing may include a spring element (not shown) that biases the movable surface toward the first position (expanded position). For example, the spring element may comprise an internal layer of that housing that may be constructed from a material with characteristics that will provide a restoring force. One example of such a material is stainless steel that may hold its shape yet be deflected by the specific operating parameter of the site where the power generator will be located. For example, in more durable sites where higher forces and pressures will be generated, more rugged materials may be used. In contrast, where forces are relatively smaller or where the operating site of the generator is more fragile or sensitive, the material of the housing can be changed accordingly. The restoring force tends to maintain the housing in the expanded configuration, as shown in FIG. 1A, while maintaining the pressure of the dielectric fluid within the chamber at a pressure less than atmospheric pressure. Additional materials may be provided to ensure impermeability of the wall, to facilitate or impede condensation of the dielectric fluid on the inner surface of the wall, and/or to facilitate maintenance of the dielectric fluid relatively free from impurities which might allow ionic conduction of electric current.

In this embodiment, the power generator includes a phase changing dielectric fluid contained within the chamber of the housing. The dielectric constant of a material quantifies, relative to vacuum, its ability to store energy in the presence of an electric field. For a gaseous material, the constant is typically very close to 1. For example, the dielectric constant of water in the gas phase is 1.00785. In some embodiments, the material chosen has a dielectric constant significantly higher than 1 in the liquid state. For ease of construction in some variations, it is also desirable that the material chosen undergoes a phase change (i.e., boils) at pressures close to atmospheric (1 atm, or 101.3 kPa) when at the intended working temperature. A suitable liquid could be pure water that has a dielectric constant of about 80 in the liquid phase and about 1 in the gas phase. Table 1, below, shows a representative sample of such materials, chosen for use near environment or body temperature.

TABLE 1

Exemplary dielectric materials.

| Material | Temperature | Dielectric constant | Approximate vapor (boiling) pressure |
|---|---|---|---|
| Methanol | 25° C. | 32.6 | 33 kPa |
| Isopropyl alcohol | 20° C. | 18.3 | 13 kPa |
| Freon 11 | 25° C. | 3.1 | Near 130 kPa |
| Acetone | 25° C. | 20.7 | 53 kPa |
| Water | 27° C. | 80 | 7.3 kPa |

The selection of optimal dielectric fluid may be guided by the amount of pressure or force available from the mechanical source. For example, high-pressure inputs may be used to liquefy dielectrics with vapor pressures significantly higher than 1 atm. Furthermore, the choice of dielectric may also be guided by considerations of biocompatibility, in the case of an implantable device. The phase changing dielectric fluid is contained within the chamber of the housing. In some variations, it is desirable that the dielectric fluid is entirely in or largely in a gaseous phase, when the housing is in full expansion, as shown in FIG. 1A. The change of the physical state of matter from gaseous phase into liquid phase is known as condensation. Condensation commonly occurs when a gas is cooled to its dew point, but the dew point can also be reached through compression. Compression is achieved by increasing the pressure of a gas by reducing its volume. As shown in FIG. 1B, as the housing reduces the volume of the chamber, it reduces the volume of the gas, and therefore increases the pressure of the gas leading to condensation of the dielectric fluid. As shown in FIG. 1B, at least some portion of the dielectric fluid 130 within the chamber 105 has become liquid In the compressed configuration, all or nearly all the dielectric fluid may be in the liquid phase. It is further desirable that the dielectric fluid 130 preferentially condenses in the space 120 between capacitor plates. While the capacitor plates may be constructed as described below to facilitate this effect, we also note that an electric field existing between capacitor plates 115 will tend to stabilize molecules of the dielectric fluid, further increasing the preference of the fluid to condense in the space 120.

As shown in FIG. 1A, in this embodiment, the power generator includes a capacitor 115 within the chamber of the housing. The capacitor includes a first plate and a second plate that define a fluid space 120 between them (i.e. the plates may not be contacting one another directly). The plates are electrically conductive plates. As shown in FIG. 1A, in some variations, the plates are two sets, each set electrically joined, stacked in alternating fashion within the chamber 105 of the device. In some variations, the plates may be constructed from electrically conductive film deposited on a non-conductive substrate (such as a polymer). In some variations, the plates may be constructed from metallic foil with or without a substrate or from other techniques, known in conventional capacitor fabrication arts In some variations, the plates may be arranged in one of several configurations wherein the fluid in the space 120 between plates is in communication with the inner chamber 105. For example the plates may be rolled into a spiral. The surface of the plates may be treated to facilitate condensation of the dielectric material in the inter-plate space. For example, the plates may include a textured surface to encourage nucleation, or may include a hydrophilic substance. The surface of the plates may also be treated with an electrically insulating substance. An example of an electrically insulating substance is a material with a dielectric constant suited to the operation of the device. For example, a polymer or an oxide layer with a dielectric constant within the range of 2 to 20 may be suitable. One example is aluminum oxide. Other materials may be used having a higher dielectric constant in the range of hundreds or thousands. One example of a high dielectric constant material is barium titinate.

The inter-plate space may be maintained in fluid communication with the inner chamber in one of several variations. In a first variation, holes or other openings (not shown) may be provided in the plates. In some variations, holes maybe drilled (or otherwise created) through the stack of plates, thereby increasing the area of communication between the inner chamber and inter-plate space. In an alternative variation, the plates may be constructed of mesh or perforated foil, with little loss of capacitance.

In some variations, the two plates may be maintained in separation by non-conductive spacers. In variations with thin plates, it may be advantageous to extend these spacers throughout the inter-plate space in the form of a porous material (not shown) partially filling this space with, for example, a porosity ratio of 0.75. The porous material may be a porous plastic film or a paper as typically used in conventional capacitor fabrication techniques. This porous material may be treated to encourage condensation of the dielectric fluid (or may alternatively be a hydrophobic material), and its fibers may be oriented to facilitate flow of the dielectric fluid from regions of the space near to the inner chamber to more remote regions of the space.

In one specific illustrative variation of the first embodiment of the power generator, as shown in FIGS. 1A and 1B, analysis demonstrates that this specific variation is capable of generating power levels in the 100-μW range or more with dimensions appropriate for a power generator under cyclical pressure variations typical of biological sources. The following dimensions and figures are intended to describe one particular variation of the embodiment, and not to otherwise constrain or limit the scope of the invention.

In this specific variation, the capacitor includes circular plates located in the center of the power generator. Given the following dimensions:

| | |
|---|---|
| Diameter of the chamber | 2.5 cm |
| Diameter of the plates | 0.5 cm |
| Thickness of each plate | 5 μm |
| Inter-plate distance | 3 μm |
| Porosity of inter-plate separators | 0.75 |
| Dielectric constant of inter-plate separators | 3 |
| Thickness of wall (housing) | 0.5 mm |
| Number of plate/separator pairs | 20 |
| Allowable axial compression | 1.5 mm | the volume for the inter-plate space is $8.4 \times 10^{-4}$ cm$^3$ and the volume for the chamber is 0.89 cm$^3$. The uncompressed height of the power generator in this variation would be 2.66 mm, while the compressed height of the device would be 1.16 mm.

In this specific variation, the dielectric fluid is water (dielectric constant=80) and the capacitance of plates with the dielectric fluid in the gas phase can be calculated from Equation (1) as 1650 pF, taking into account porosity and dielectric constant of the inter-plate separators. Capacitance of the plates with the dielectric fluid in the liquid phase would be approximately 66800 pF, for a liquid to gas capacitance ratio of 40:5.

Assuming constant charge on the plates, the energy J produced from each compression-expansion cycle of this device may be calculated as:

$$J = C_{initial}V_{initial}^2/2 - C_{final}V_{final}^2/2 \quad \text{(Equation 3)}$$

where C is capacitance and V is voltage. Obtaining initial and final voltages from Equation 2, the resulting energy available is 530 μJ per cycle, or 530 μW with a 1 Hz compression-expansion cycle.

The power generator of the first embodiment, as shown in FIGS. 1A and 1B, may adapted to be an implantable power generator for converting mechanical energy from a patient to electrical energy that includes a compressible element (housing 100) adapted and configured to be placed between two adjacent tissue layers of the patient and to be compressed (as shown in FIG. 1B) by a force applied from the two adjacent tissue layers to the compressible element, and a transducer (capacitor 115), coupled to the compressible element, that converts mechanical energy from the compression of the compressible element to electrical energy. In some variations, as shown in FIGS. 1A and 1B, the compressible element includes a base 101 adapted and configured to be coupled to the first tissue layer, and a moveable surface 103, substantially opposite to the base, adapted and configured to be coupled to the second tissue layer. As shown in FIG. 1B, the force applied from the two adjacent tissue layers to the compressible element moves the movable surface with respect to the base, thereby compressing the compressible element.

Figure 2:
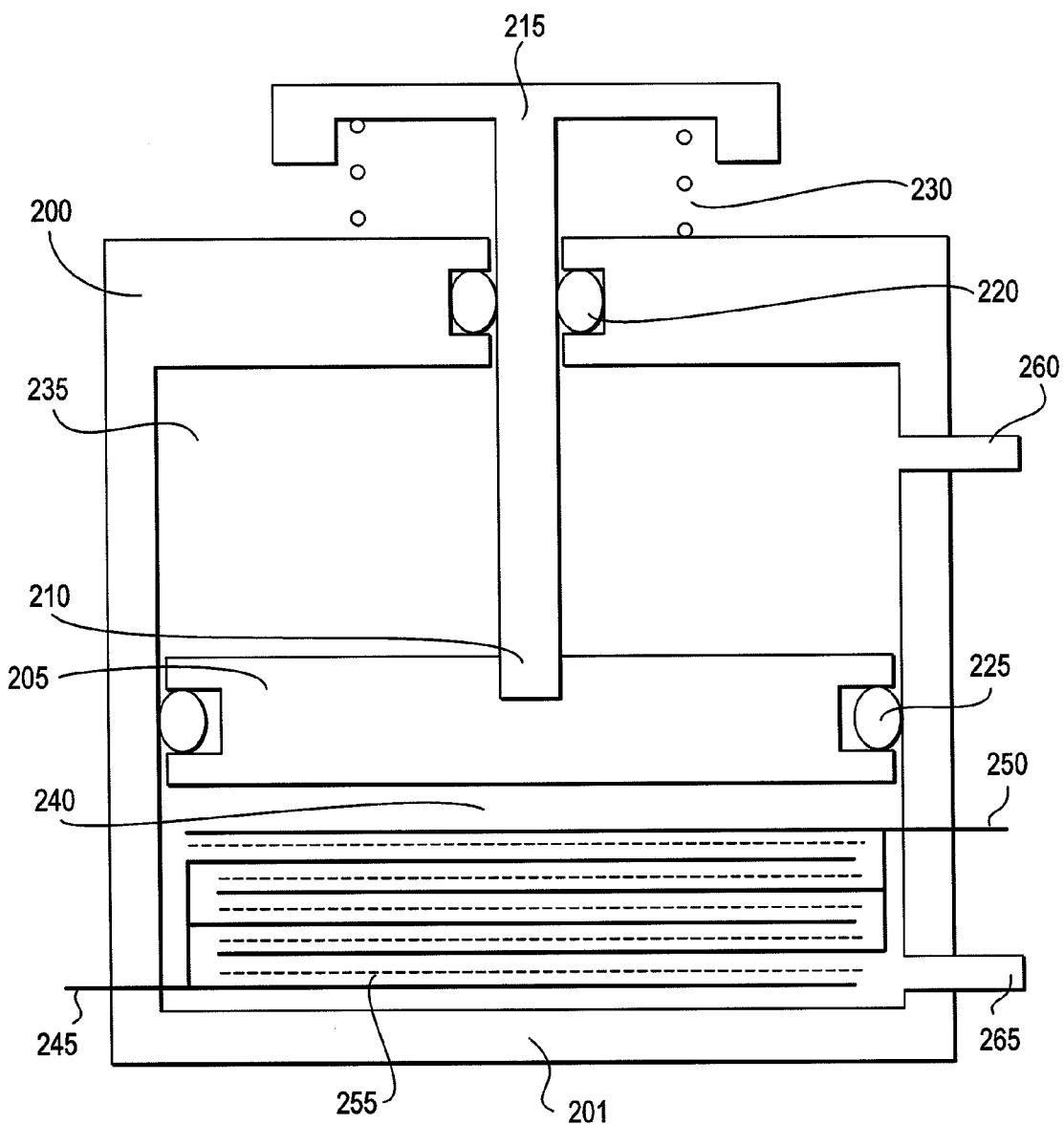
FIG. 2 is a drawing of a second embodiment of the power generator that includes a capacitor and a phase changing dielectric fluid.

FIG. 2 shows a power generator of a second embodiment. The power generator as shown in FIG. 2 includes a housing 200 that defines a chamber. The chamber is divided into two portions 235 and 240 by the piston head 205. There is a capacitor and a phase changing dielectric fluid in chamber portion 240. The capacitor has two plates 245 and 250 having a space between them that is in fluid communication with the fluid in the rest of the chamber portion 240. The piston head 205 is coupled to a piston 210 and to a button 215 that move the piston head within the chamber toward the base 201 of the housing 200. As the piston head 205 moves toward the base 201, the volume of the fluid within the chamber portion 240 is reduced, and the fluid changes phases. The capacitance of the capacitor changes as the phase changes, and electrical energy is generated in the form of the voltage and/or charge on plates of the capacitor, as the capacitance between these plates changes.

In a second embodiment, the power generator for converting any suitable form of mechanical energy to electrical energy includes a housing 200 that defines a chamber 235 and 240, a phase changing dielectric fluid contained within the chamber 240 of the housing, a moveable surface 205 coupled to the housing that defines the volume of the phase changing dielectric fluid, and a capacitor within the chamber of the housing. In some variations, the housing includes a base 201 substantially opposite to the moveable surface. The base and the moveable surface 205, and their position relative to one another, define the volume of the phase changing dielectric fluid.

In this second embodiment, as shown in FIG. 2, the capacitor includes interleaved electrodes with attached wires 245 and 250. The electrodes are separated by spacers 255 of high porosity creating a capacitor element. The electrodes are preferably perforated to facilitate the passage of a dielectric fluid in either the gas or liquid phase. The wires extend through the housing 200 of the device by means of fluid-tight feedthroughs to allow electrical connection. A piston made up of a piston head (the movable surface 205), a shaft 210 and a button 215 is used to receive the forces applied to movable surface and thereby compress or reduce the volume of the phase changing dielectric fluid. A sliding seal 225 on the piston head 205 separates chambers 235 and 240. Another sliding seal 220 separates chamber 235 from the outside environment. In some variations, the seals may be O-rings or other sliding seal configurations. In some variations, the chambers may be sealed with bellows or bladders within the chambers rather than sliding seals.

In some variations, chamber 240 may filled through fill tube 265 with a dielectric fluid such as pure water. With piston head 205 compressing the chamber 240 to its minimum volume, fill tube 265 is sealed by crimping, welding, an adhesive, or other technique. Chamber 235 may be completely or partially evacuated through fill tube 260 which can then be sealed. If the diameter of the shaft 210 is comparatively small, and chamber 235 is a reasonably hard vacuum, then the low pressure in the chamber 235 will be communicated to the chamber 240 resulting in vaporization of the dielectric fluid and travel of the piston head 205 to increase the volume of chamber 240 and decrease volume of the chamber 235. Pressure applied to the button 215 will recompress the chamber 240 causing the dielectric fluid to condense into a liquid. Note that by controlling the pressure in chamber 235 the resting state of the dielectric fluid in chamber 240 may be selected to be either liquid or gas at a fixed operating temperature (body temperature for an implantable device). An optional spring 230 connected between the button 215 and the wall 200 of the device provides an additional mechanism for establishing a mechanical operating point. In some embodiments, the working fluid in chamber 235, under the influence of pressure cycles, is at least partially a liquid and partially a gas.

The power generator of the second embodiment, as shown in FIG. 2, may be an implantable power generator for converting mechanical energy from a patient to electrical energy includes a compressible element (button 215 attached to a piston 210, which is connected to a piston head 205) adapted and configured to be placed between two adjacent tissue layers of the patient and to be compressed by a force applied from the two adjacent tissue layers to the compressible element. There is also a transducer (as shown in FIG. 2, formed from a capacitor having plates 245 and 250). The transducer is coupled to the compressible element and converts mechanical energy from the compression of the compressible element to electrical energy. In some variations, as shown in FIG. 2, the compressible element includes a base 201 adapted and configured to be coupled to the first tissue layer, and a moveable surface 205, substantially opposite to the base, adapted and configured to be coupled to the second tissue layer (via piston 210 and button 215). As shown in FIG. 2, the force applied from the two adjacent tissue layers to the compressible element moves the movable surface with respect to the base, thereby compressing the compressible element.

Figure 3A:
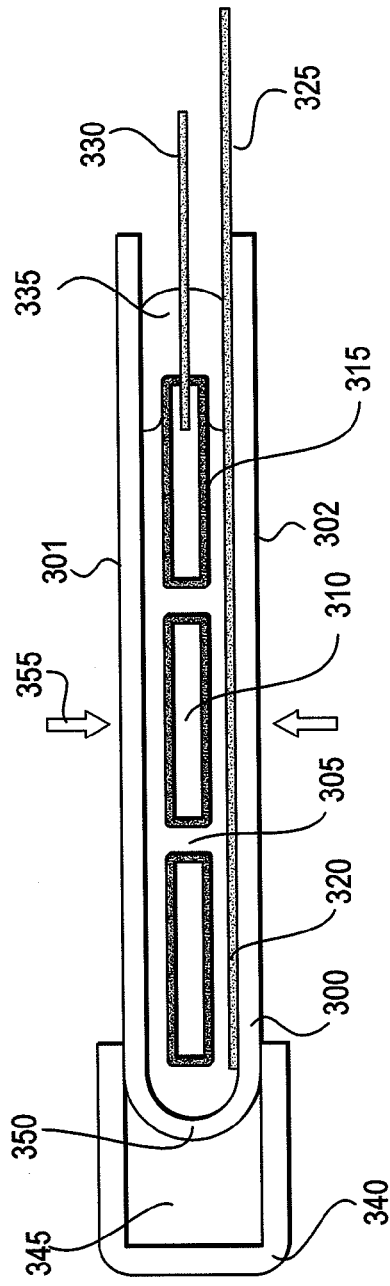
FIGS. 3A-3B are drawings of a third embodiment of the power generator that includes a capacitor and a housing that displaces a dielectric fluid.
Figure 3B:
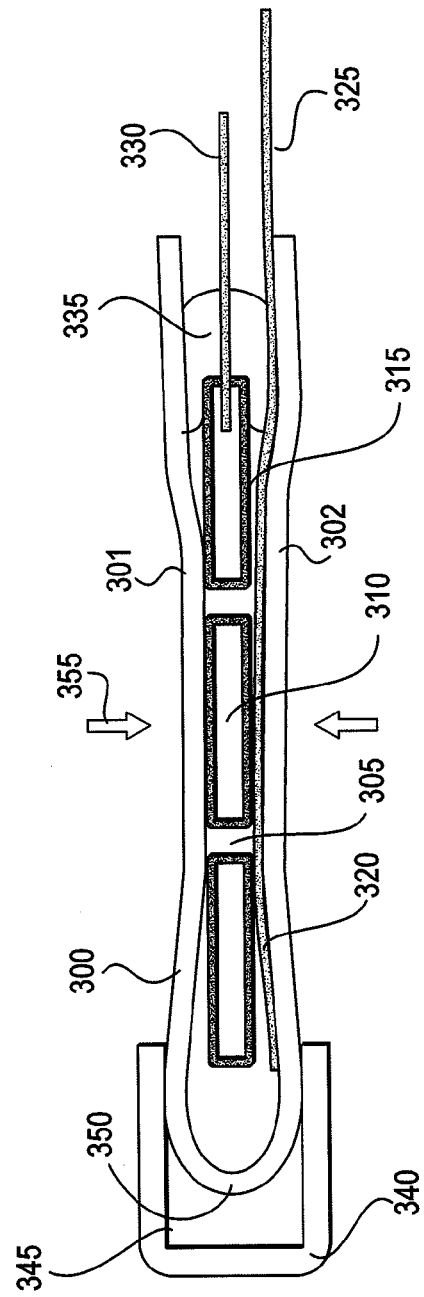

FIG. 3A shows a power generator of a third embodiment. The power generator as shown in FIG. 3A includes a housing 300. The housing encloses a capacitor and a dielectric fluid. The capacitor has a first plate 310 and a second plate 320 coupled to the inside wall of the housing 300. The plate 310 is coupled to an insulator 315 and may define one or more apertures 305, which allow passage of the fluid through the plate 310. The housing includes portion 301 that, as force 355 is applied, moves with respect to a portion 302, such that, as shown in FIG. 3B, the housing is compressible. As the housing 300 is compressed, and as plate 320 moves toward plate 310 and/or insulator 315, the fluid is displaced from between the plates of the capacitor. The capacitance of the capacitor changes as the amount of dielectric fluid between the plates changes, and electrical energy is generated in the form of the voltage and/or charge on plates of the capacitor, as the capacitance between these plates changes.

In the third embodiment, as shown in FIG. 3, the power generator for converting any suitable form of mechanical energy to electrical energy includes a housing 300 that defines a chamber and comprises a movable surface 302, a dielectric fluid contained within the chamber of the housing, and a capacitor within the chamber of the housing. In some variations, the capacitor includes a first and second plate (310 and 320), and an insulator 315 coupled to the first plate and disposed between the first plate and the second plate. At least one plate may be coupled to a movable surface of the housing, and the plates have a first voltage across them when a first amount of the dielectric fluid is between the insulator and the second plate, and the plates have a second voltage across them when a second amount of the dielectric fluid is between the insulator and the second plate. The movable surface may displace the dielectric fluid such that the second amount of the dielectric fluid is less than the first amount of the dielectric fluid.

In the third embodiment, as shown in cross section in FIG. 3, the power generator includes a housing 300, having at least one movable surface that defines a chamber. In some variations, the flexible housing includes a membrane 300 preferably fabricated of a thin polymer. The membrane 300 receives pressure a force 355 applied from two tissue layers. In some variations, the housing is adapted and configured to be placed between two adjacent muscle layers of the muscle and to be compressed by a pressure generated by the muscle contracting. In some variations, the flexible housing may be a single continuous housing, having at least one movable surface. In alternative variations, the housing may include an open portion that may be sealed with a plug 335, as shown in FIG. 3. The plug may be an adhesive or other suitable material. Two electrically conducting wires 330 and 325 may connect to the elements of the capacitor through the plug. Additionally, in some variations, elements of the capacitor may be held in position within the chamber of the housing by the plug 335. In some variations, the housing may further include a compliant separator 350 backed by a gas filled expansion space 345 that is further contained by a comparatively rigid wall 340.

As shown in FIG. 3, the power generator includes a capacitor. In some variations, the capacitor includes an electrically conducting film 320 coupled to the inside wall of the housing, a dielectric fluid within the chamber of the housing, and a metal foil 310, having an insulation layer 315, submerged in the dielectric fluid. In this embodiment the foil 310 is one plate of the capacitor and the conductive film 320 on the membrane 300 is the other plate, while the dielectric fluid and/or the insulator 315 are the dielectric of the capacitor. In some variations, the conductive film may be deposited on the housing or may be fabricated using other methods. In some variations, the dielectric fluid is a fluid having a low dielectric constant such as oil. In some variations, the metal foil may have apertures 305 through which the dielectric fluid may flow. The metal foil may be made of titanium, stainless steel or any other suitable conductor. In some variations, the metal foil includes a thin coating of an insulator 315 on its surface. The insulator 315 is preferably made from a material having a high dielectric constant such as barium titanate.

In operation, as a force 355 is applied to the housing, the movable surface(s) of the housing, with its conductive foil backing 320, is compressed and displaces the dielectric fluid as it is pressed up against the insulating coating 315 of the foil 310, as shown in FIG. 3B. In some variations, the housing includes two movable surfaces that may both compress and displace the dielectric fluid as they are pressed up against the insulating coating 315 of the foil 310. While compressed (the high pressure state), a comparatively high value capacitor is formed having the foil 310 and the conductive film 320 as its plates or electrodes, and the high dielectric constant insulator 315 as the dielectric. During the high pressure state, as shown in FIG. 3B, a force is transmitted to the separator 350 by the displaced dielectric fluid causing it to bulge into the compliance space 345 compressing the gas within. When the force 355 subsides (the low pressure state), the spring force of the compressed gas in the compliance space 345 and the distended separator 350 puts a force on the dielectric fluid that restores the housing to the expanded configuration and pushes the membrane 300 and the foil layer 320 away from metal foil 310 and the insulating layer 315. During the low pressure state, as shown in FIG. 3A, a comparatively low value capacitor is formed not only because the plates of the capacitor (320 and 310) are further apart, but also because the low dielectric fluid is now between the plates (320 and 310) in addition to the insulator 315, dropping the capacitance dramatically. During the high pressure state, as shown in FIG. 3B, the capacitance is high and a low voltage (the "seed" voltage) may be imposed on the capacitor. During the low pressure state the capacitance drops and the voltage on the capacitor increases allowing energy to be collected by a circuit (as described below) or other suitable energy collecting component.

The power generator of the third embodiment, as shown in FIG. 3, may be an implantable power generator for converting mechanical energy from a patient to electrical energy includes a compressible element (housing 300) adapted and configured to be placed between two adjacent tissue layers of the patient and to be compressed by a force 355 applied from the two adjacent tissue layers to the compressible element. A transducer, coupled to the compressible element, converts mechanical energy from the compression of the compressible element to electrical energy. In some variations, this embodiment may be primarily intended for implantation between two muscle layers, such as within or between muscle bundle(s). In some variations, as shown in FIG. 3, the compressible element includes a base 301 adapted and configured to be coupled to the first tissue layer, and a moveable surface 302, substantially opposite to the base, adapted and configured to be coupled to the second tissue layer. As shown in FIG. 3, the force 355 applied from the two adjacent tissue layers to the compressible element moves the movable surface with respect to the base, thereby compressing the compressible element. In some embodiments, the base and the movable surface of the housing form an enclosure that may enclose components of the power generator.

Figure 11:
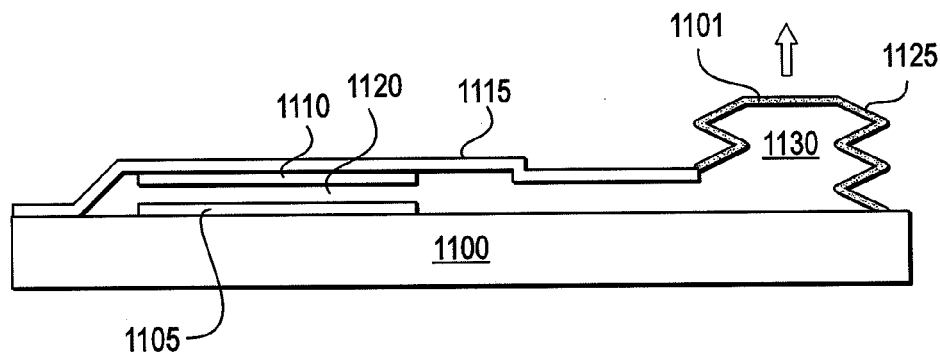
FIGS. 11-12 are drawings of a fourth embodiment of the power generator that includes a compressible element that displaces a fluid and a capacitor.
Figure 12:
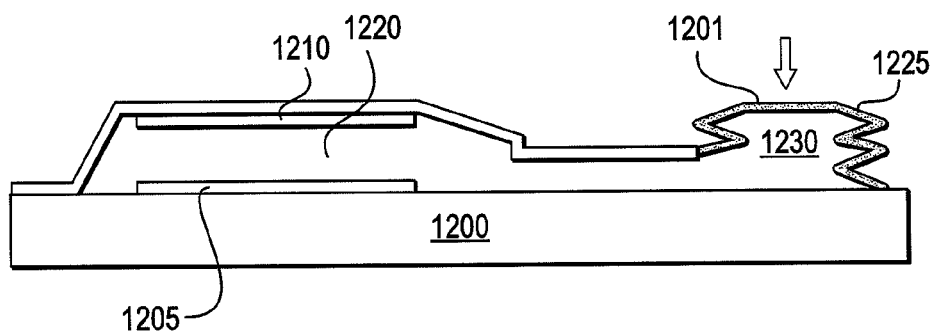

FIG. 11 shows a power generator of a fourth embodiment. The power generator as shown in FIG. 11 includes a housing 1115 and a base 1100 that enclose a fluid 1120. The power generator also includes a compressible element 1125, having a movable surface 1101, which encloses a fluid 1130 and a capacitor having plates 1110 and 1105. Fluid 1120 and 1130 may be in fluid communication. As shown in FIG. 12, as the compressible element 1225 is compressed and movable surface 1201 moves with respect to the base 1200, the compressible element displaces a fluid 1230 and causes a fluid pressure, such that fluid 1220 separates the plates 1210 and 1205 of the capacitor. The capacitance of the capacitor changes as the distance between the plates changes, and electrical energy is generated in the form of the voltage and/or charge on plates of the capacitor, as the capacitance between these plates changes.

In a fourth embodiment, as shown in cross section in FIGS. 11-12, the compressible element 1125 includes a base 1100 adapted and configured to be coupled to the first tissue layer, and a moveable surface 1101, substantially opposite to the base, adapted and configured to be coupled to the second tissue layer. As shown in FIG. 12, the force applied from the two adjacent tissue layers to the compressible element moves the movable surface 1201 towards the base 1200, thereby compressing the compressible element. In a fourth embodiment, as shown in cross section in FIGS. 11-12, the transducer includes a capacitor having a first plate 1105, a second plate 1110, and a dielectric 1120. In some variations, the dielectric is at least partially fluid.

The compressible element in this embodiment may be a bellows, a piston or other similar mechanical device to displace fluid. The compression of the compressible element displaces a fluid 1130 within the compressible element and causes a fluid pressure to separate the plates of the capacitor. If the capacitor is pre-charged (i.e. initially has a voltage on it) then separating the plates will result in a higher voltage, and an electrical energy that can be collected. In some variations, an electrical circuit may be used to remove the energy from the capacitor to operate a circuit, charge a battery, or for some other useful purpose.

As shown in FIGS. 11 and 12, the fourth embodiment of the power generator includes a base 1100, which in some variations is an electrically insulating substrate. The compressible element 1125 and/or a plate 1105 of the capacitor may be directly mounted onto the base 1100. In some embodiments, the compressible element may include the plates of the capacitor, such that the force applied functions to directly compress and move the plates of the capacitor closer together. Alternatively, as shown in FIG. 11, the power generator may further include a flexible housing 1115 coupled to the compressible element and to the base. In some variations, the second plate 1110 may be coupled to the flexible housing 1115. The flexible housing may define a chamber enclosing fluid 1120, and the compressible element encloses a fluid 1130. In some variations, the fluid 1130 in the compressible element is in fluid communication with fluid 1120 between the plates of the capacitor.

As shown in FIG. 11, when the compressible element 1125 is expanded, the distance between the capacitor plates 1105 and 1110 is reduced. Since the capacitance is inversely proportional to the distance between the plates, the capacitance is highest when the compressible element is expanded. As shown in FIG. 12, when the compressible element is compressed, the fluid 1230 in the compressible element 1225 communicates pressure to the fluid 1220 between the capacitor electrodes 1205 and 1210 thereby increasing the separation between the electrodes, which causes the capacitance of the capacitor to decrease.

When a voltage is present on the capacitor plates (i.e. when the plates are pre-charged), before the compressible element is compressed, the voltage will increase when the compressible element is compressed. Assuming constant charge on the plates, the energy J produced from each compression-expansion cycle of this device may be calculated as:

$$J = C_{initial} V_{initial}^2 / 2 - C_{final} V_{final}^2 / 2 \quad \text{(Equation 4)}$$

where $C_{initial}$ is the capacitance when the plates are close together and $V_{initial}$ is the voltage put on the capacitor. where $C_{final}$ is the capacitance when the plates are further away, and $V_{final}$ is the resulting voltage when the capacitor plates are further away from each other. If the distance between the capacitor plates doubles, the capacitance will be halved and the voltage will be doubled. Since the energy stored is proportional to the square of the voltage, doubling the distance between the capacitor plates will double the stored energy even though the capacitance is halved. The extra energy comes from the mechanical work done to separate the electrical charges on the capacitor plates; in other words mechanical energy is converted to electrical energy that can be collected by a circuit (as described below) or other suitable energy collecting component.

The fluid 1120, 1220 between the capacitor plates (1105 and 1110 or 1205 and 1210) acts as the dielectric for the capacitor. Preferably the fluid 1120, 1130 is an oil or glycerin. The dielectric fluid may include additives such as micro or nano-scale particles to assure that the plates of the capacitor cannot touch. Furthermore the particles may be of a material like barium titanate to increase the dielectric constant so the device can have a higher capacitance and therefore store and convert greater amounts of energy. In addition, one or both electrodes may be patterned or coated with a dielectric using, for example, Microelectromechanical systems (MEMS) or Integrated Circuit (IC) manufacturing techniques for coating of etching materials. In the alternative, a conventional capacitor film dielectric can be placed between the electrodes. It is anticipated that stacked designs or cylindrical configurations may advantageously be used.

Power Generators—Exemplary Electromechanical Embodiments

Figure 4A:
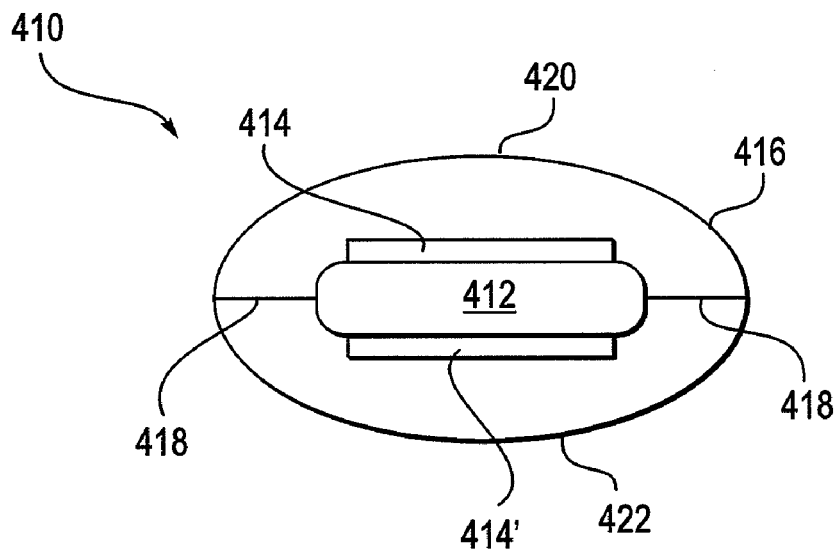
FIGS. 4A-4B are drawings of a fifth embodiment of the power generator that includes a housing, a structural member, and a transducer.

FIG. 4A shows a power generator 410 of a fifth embodiment. The power generator 410 as shown in FIG. 4A includes a housing 416, a transducer 412, and a structural member 418 that couples the housing to the transducer. As the housing 416 is compressed and housing portion 420 moves with respect to housing portion 422, as shown in FIG. 4B, the structural member 418 stretches the transducer 412 and activates the transducer such that it may convert the mechanical energy from the compression of the housing to electrical energy.

Figure 5A:
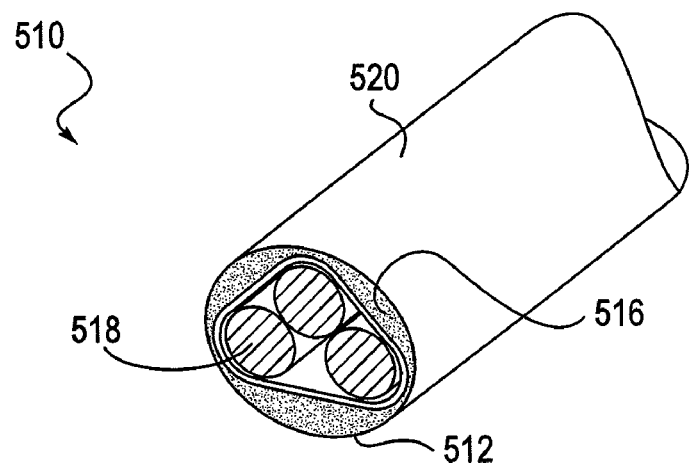
FIGS. 5A-6C are drawings of a sixth embodiment of the power generator that includes a housing, a structural member, and a transducer.

FIG. 5A shows a power generator 510 of a sixth embodiment. The power generator 510 as shown in FIG. 5A includes a housing 516, a structural member 518, and a transducer 512 that is wrapped around the structural member. As the housing 516 is compressed and housing portion 520 moves with respect to housing portion 522, as shown in FIG. 5B, the structural member 418 moves from a first (substantially triangular, as shown) configuration to a second (substantially horizontal, as shown) configuration, such that it stretches the transducer 412 and activates the transducer such that it may convert the mechanical energy from the compression of the housing to electrical energy.

Figure 7B:
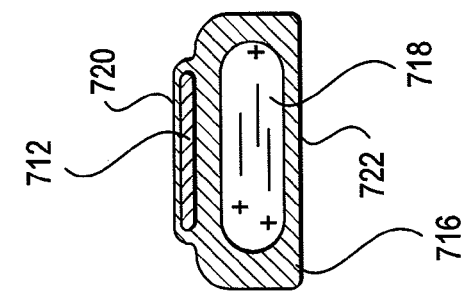
FIGS. 7A-7B are drawings of a seventh embodiment of the power generator that includes a housing, a structural member, and a transducer.
Figure 7A:
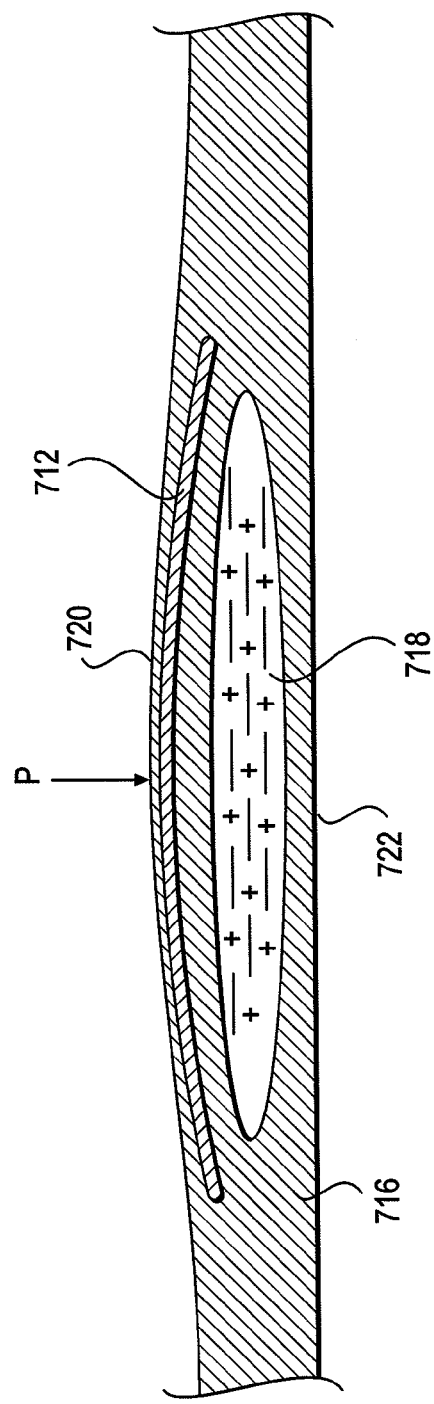

FIG. 7A shows a power generator of a seventh embodiment. The power generator as shown in FIG. 7A includes a housing 716, a flexible structural member 718, and a transducer 712 that positioned adjacent to the structural member. As the housing 716 is compressed and housing portion 720 moves with respect to housing portion 722, the structural member 718 compresses such that the transducer 712 is bent and/or flexed such that it is activated and may convert the mechanical energy from the compression of the housing to electrical energy.

Figure 4B:
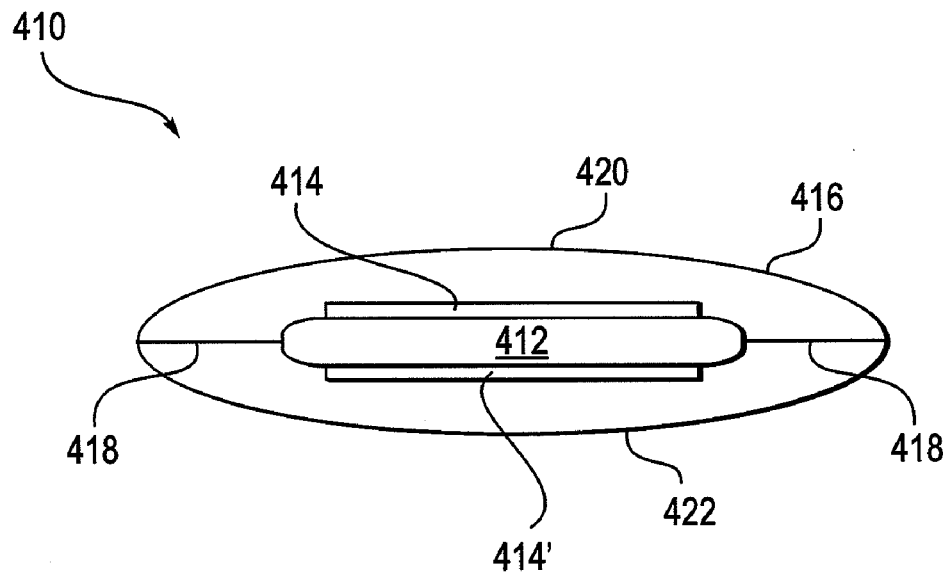
Figure 5B:
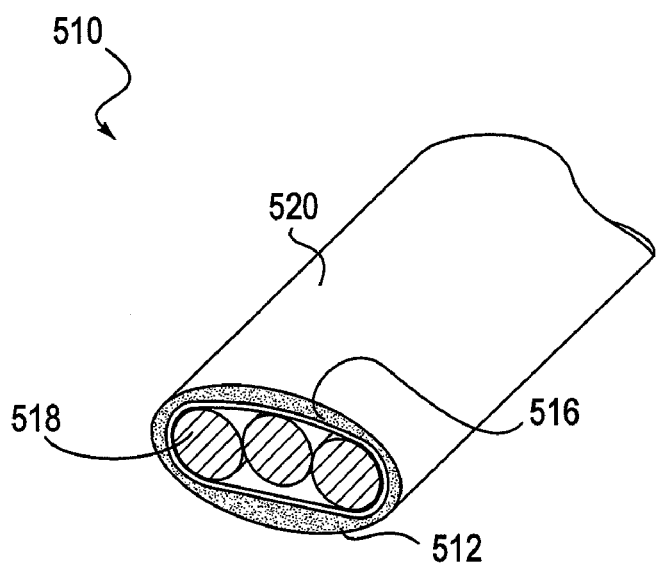

In a fifth, sixth, and seventh embodiment, as shown in FIGS. 4A and 4B, FIGS. 5A-6C, and FIGS. 7A AND 7B respectively, the compressible element of the implantable power generator includes a housing that is compressible (as shown in FIG. 4B or 5B) by a force applied from the two adjacent tissue layers to the compressible element such that the housing moves between an equilibrium position and an activated (compressed) position and transmits a mechanical force to a transducer. The housing may further include a structural member, as in the fifth and sixth embodiments, for example, as shown in FIGS. 4A and 4B, FIGS. 5A-6C respectively, which is coupled to the housing and/or the transducer and functions to transmit a mechanical force to the transducer.

As shown in FIGS. 4A and 4B, FIGS. 5A-6C, and FIGS. 7A AND 7B, the compressible element may include a base (422, 522, or 722) adapted and configured to be coupled to the first tissue layer, and a moveable surface (420, 520, or 720), substantially opposite to the base, adapted and configured to be coupled to the second tissue layer. As shown in FIG. 4B, the force applied from the two adjacent tissue layers to the compressible element moves the movable surface with respect to the base, thereby compressing the compressible element. The housing may further function to protect the implantable power generator from the stresses of the implant environment. The mechanical and/or electronic components may be encased in a flexible, biocompatible polymer sheath preferably made of polyimide, polyurethane or silicone rubber or a combination thereof. The housing may be assembled and glued or insert molded.

In the fifth and sixth embodiments, as shown in FIGS. 4A and 4B and FIGS. 5A-6C respectively, the transducer (412 or 512) may be an electro active polymer that generates an electric potential in response to mechanical stress, force and/or shape change. The transducer may alternatively be one or more of any of several suitable transducers such piezo-active polymers (such as Polyvinylidene Fluoride (PVDF)), coils and magnet style transducers, other piezoelectrical materials, electromagnetic elements, nano-generators, other transduction elements or suitable miniaturized or Microelectromechanical (MEMS) based systems, devices, or structures. In the fifth and sixth embodiment, the transducer is preferably coupled to the housing (416 or 516) such that when the housing is compressed, as shown in FIGS. 4B and 5B, the housing moves to an activated (compressed) position and the transducer is stretched. The transducer has a capacitance ($C_i$) in the stretched state and an electrical potential ($V_i$) that is imposed on the electrodes 14 and 14' in the stretched state. The initial stored energy ($J_i$) is equal to $$\frac{1}{2} \times C_i \times V_i^2.$$

The capacitance ($C_i$) of the transducer is proportional to the area and thickness of the transducer. When the compression on the housing is released, as shown in FIGS. 4A and 5A, the housing returns to an equilibrium position and the transducer becomes thicker, reducing the capacitance. The electrical potential increases however, and the energy stored by stretching the transducer generates electrical energy. In some variations, the electrical energy is stored on a capacitor or in a battery for subsequent use, and the cycle repeats as the housing 16 is again compressed and then released.

Figure 6A:
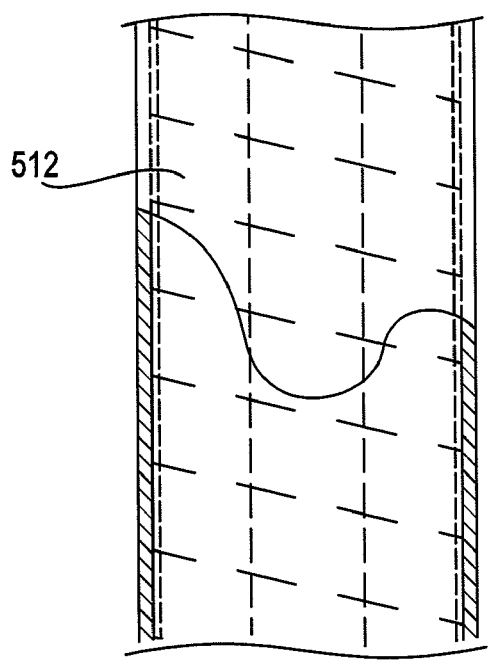
Figure 6B:
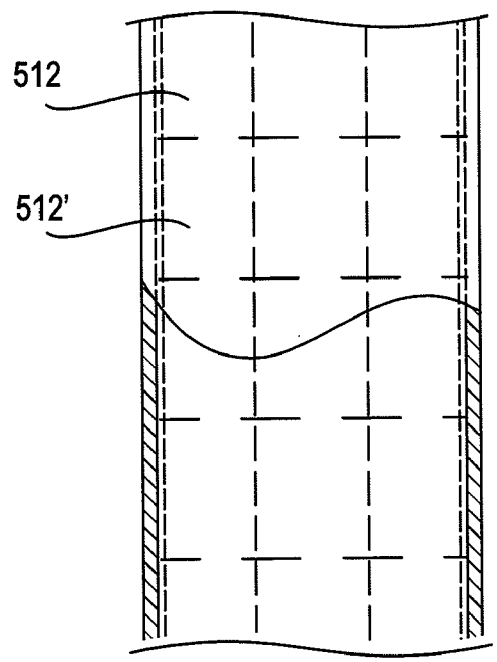
Figure 6C:
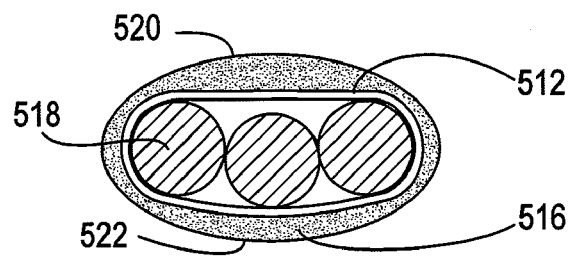

In the fifth and sixth embodiments, as shown in FIGS. 4A and 5B, the transducer is preferably coupled to the housing such that when the housing is compressed, the housing moves to an activated position and the transducer is stretched. As shown in FIG. 4A, the structural member 418 in the fifth embodiment is preferably a connective member that is coupled to the housing and to the transducer such when the implantable power generator is compressed, as shown in FIG. 4B, the structural member 418 is pulled by the housing 416 and stretches the transducer 412. In the sixth embodiment, as shown in FIGS. 5A and 5B, the transducer 512 is preferably coupled to the housing 516 such that when the housing is compressed, as shown in FIG. 5B, the housing moves to an activated position and the transducer is stretched and is in tension. The structural member 518 in this variation includes preferably at least three substantially rigid members that are disposed within the housing and are coupled to the transducer. As shown in FIGS. 6A and 6B, the transducer 512 is preferably located within the housing 516 and wrapped around the structural members 518. In a first version, as shown in FIG. 6A, the transducer 512 is a single band wrapped continuously around the structural members in a helical fashion. In a second version, as shown in FIG. 6B, multiple bands 512, 512' are wrapped perpendicularly around the structural member; the multiple bands however, may alternatively be wrapped at any other suitable angle to the structural members 18.

In the sixth embodiment, as shown in FIGS. 5A and 5B, when the compressible element is compressed the structural members move from a first arrangement, having a first perimeter, to a second arrangement, having a second, larger perimeter. The transducer is preferably wrapped around at least a portion of the structural members such that as the structural members move from the first arrangement to the second arrangement, the transducer is stretched around the larger perimeter. In some embodiments, the first arrangement may be a triangular arrangement (as shown in FIG. 5A) and the second arrangement may be a substantially horizontal arrangement (as shown in FIG. 5B). In the triangular arrangement, the arrangement of the structural members has a first perimeter. In the horizontal arrangement, the arrangement of the structural members has a second, larger perimeter. The transducer is preferably wrapped around at least a portion of the structural members such that as the structural members move from the triangular arrangement to the horizontal arrangement, the transducer is stretched around the larger perimeter. The housing is these embodiments is preferably a compliant, flexible material such as silicone, but may alternatively be any suitable material. The structural member is preferably a connective member that will not stretch in tension such that it can pull and stretch the transducer 12 as the housing in compressed and flattened.

In the seventh embodiment, as shown in FIGS. 7A AND 7B, the transducer 712 is preferably one or more piezoelectric fibers, which generate an electric potential in response to mechanical stress or force. The transducer may also be other suitable generators such piezo-active polymers (such as Polyvinylidene Fluoride (PVDF)), coils and magnet style transducers, other piezoelectrical materials, electromagnetic elements, nano-generators, other transduction elements or suitable miniaturized or Microelectromechanical (MEMS) based systems, devices, or structures. In the seventh embodiment, as shown in FIGS. 7A AND 7B, the transducer is preferably coupled to the housing 716 such that when the housing is compressed, the housing moves to an activated position and the transducer receives a mechanical stress or force and is flexed or bent. The housing in this embodiment is preferably a material such as silicone, but may alternatively be any suitable material. The structural member 718 is preferably a material that is softer or more flexible than the material of the housing such that when a force or pressure P is applied substantially perpendicular to the housing, as shown in FIGS. 7A AND 7B, the structural member will compress more than the housing and the portion of the transducer above or adjacent to the structural member will bend and/or flex. The housing in this variation may further include additional pockets of structural members, such that the transducer will bend at multiple points. In a second version of the third variation, rather than including a structural member, the housing may have a pocket that is full of a fluid (such as a air or water), or the housing may be shaped in a semi-circular shape such that the center portion (i.e. the highest portion of the semi-circle) may bend and flex into the air pocket or into the open space below the high portion of the semi-circle in response to a force or pressure P that is applied substantially perpendicular to the housing thereby bending or flexing the transducer.

In some variations of the fifth, sixth, and/or seventh embodiments, the transducer further includes an electrode that collects the electrical energy generated by the transducer. In the fifth embodiment, as shown in FIGS. 4A and 4B, the implantable power generator 410 includes an electrode 414 on a first side of the transducer and an electrode 414' on a second side of the transducer. In one configuration, the first side of transducer may be opposite the second side of the transducer. The electrodes may be flexible, but may alternatively have any suitable material properties.

Figure 8:
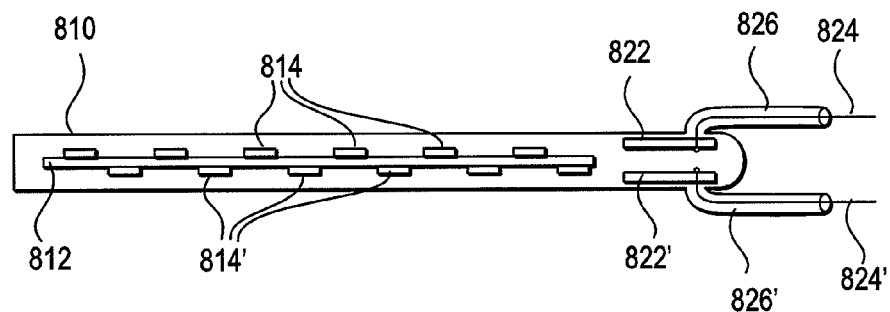
FIGS. 8-10 are drawings of an eighth embodiment of the power generator that includes a transducer and a housing.
Figure 9:
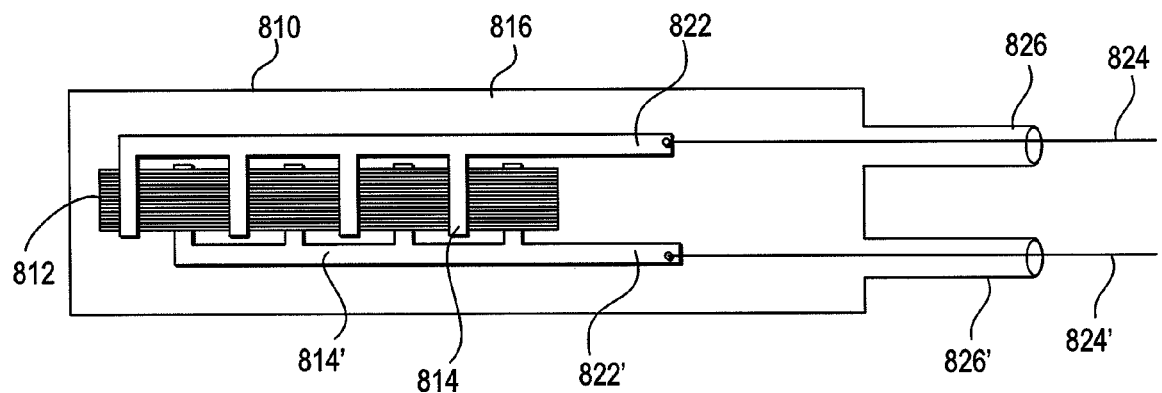
Figure 10:
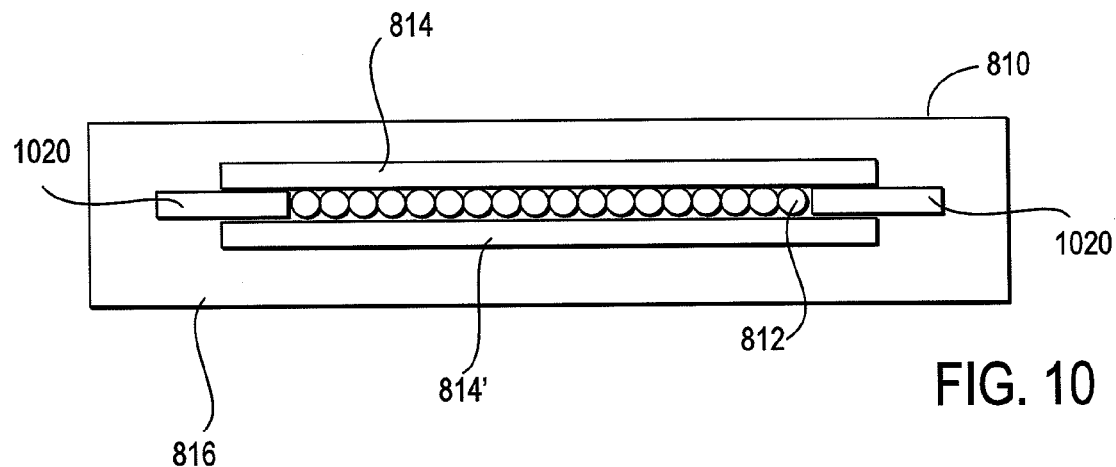

In an eighth embodiment, as shown in FIGS. 8-10, the transducer 812 may be implanted such that the mechanical energy collected is generated directly by the movement of muscle relative to bone and/or relative to the implantable power generator 810 such that the implantable power generator and the transducer flexes or bends rather than, or in addition to being compressed. In one specific embodiment, the transducer preferably runs almost the entire length of the implantable power generator. Alternatively, the transducer may have any suitable geometry and size to correspond to all or a portion of the dimensions of the implantable power generator.

In the eighth embodiment, as shown in FIGS. 8-10, the transducer is preferably one or more piezoelectric fibers, which generate an electric potential in response to mechanical stress or force. The transducer of the eighth embodiment may also be other suitable generators such piezo-active polymers (such as Polyvinylidene Fluoride (PVDF)), coils and magnet style transducers, other piezoelectrical materials, electromagnetic elements, nano-generators, other transduction elements or suitable miniaturized or Microelectromechanical (MEMS) based systems, devices, or structures.

As shown in FIG. 9, the piezoelectric fibers of the transducer 812 preferably lay side-by-side with one electrode 814 shown on top of the transducer, and the other electrode 814' shown beneath the transducer. Although comparatively few extensions of the electrodes over the transducer are shown for clarity, any suitable number and/or configuration of the extensions of the electrodes over the transducer may be utilized. In this embodiment, the motion or compression of a muscle causes the transducer to flex or bend (similarly to the seventh embodiment as shown in FIGS. 7A and 7B) and a voltage appears across the transducer that is collected by the electrodes. The implantable power generator 810 preferably includes two electrodes: top electrode 814 and bottom electrode 814', which make contact with opposite sides of the transducer. As shown in FIG. 9, the piezoelectric fibers of the transducer are preferably sandwiched between the electrodes. In some variations, as shown in FIG. 10, the implantable power generator may include an insulating separator 1020 that prevents the electrodes from shorting one another. The insulating separator is preferably made of a polymer such as polyimide, but may alternatively be made of any suitable insulating material.

Figure 13A:
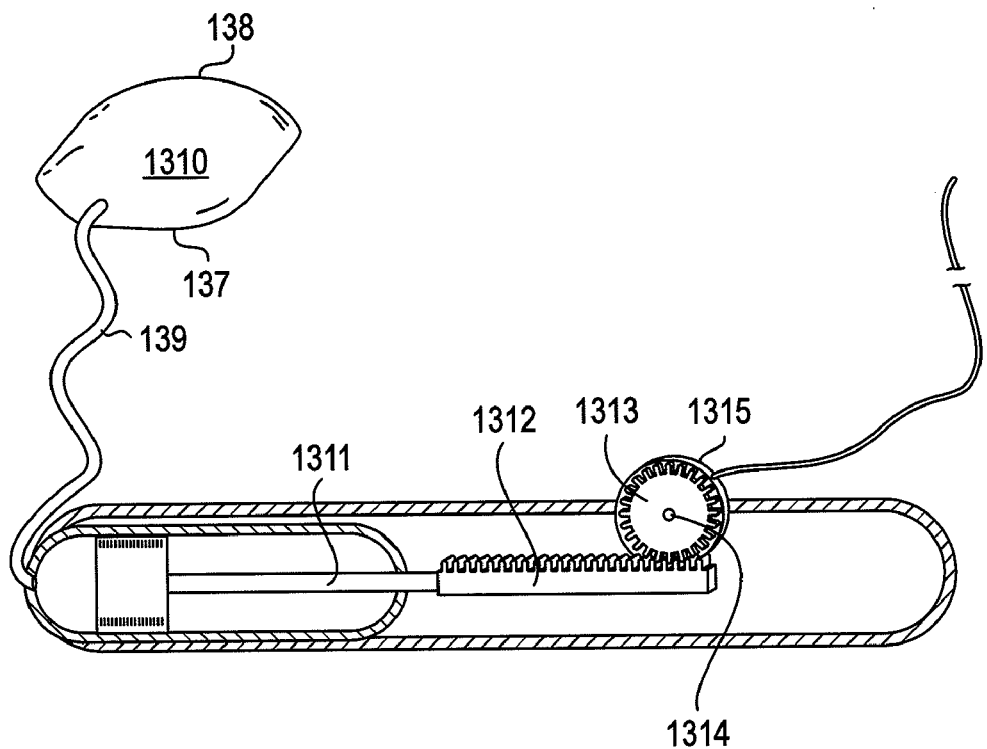
FIGS. 13A-15 are drawings of a ninth, tenth, and eleventh embodiment of the power generator that includes a compressible element that displaces a fluid and an electromagnetic generator.

FIG. 13A shows a power generator of a ninth embodiment. The power generator as shown in FIG. 13A includes a compressible element 1310 having a portion 138 that moves with respect to portion 137. The power generator also includes a transmission that includes a piston 1311, a rack 1312, and a pinion 1313. The pinion 1313 is coupled to an electromagnetic generator 1315 through axel 1314. As the compressible element 1310 is compressed, as shown in FIG. 13B, it displaces a fluid through link 139 such that a fluid pressure moves the piston 1311 and rack 1312, which rotates the pinion 1313 that actuates the electromagnetic generator 1315 such that it may generate electrical energy.

Figure 13B:
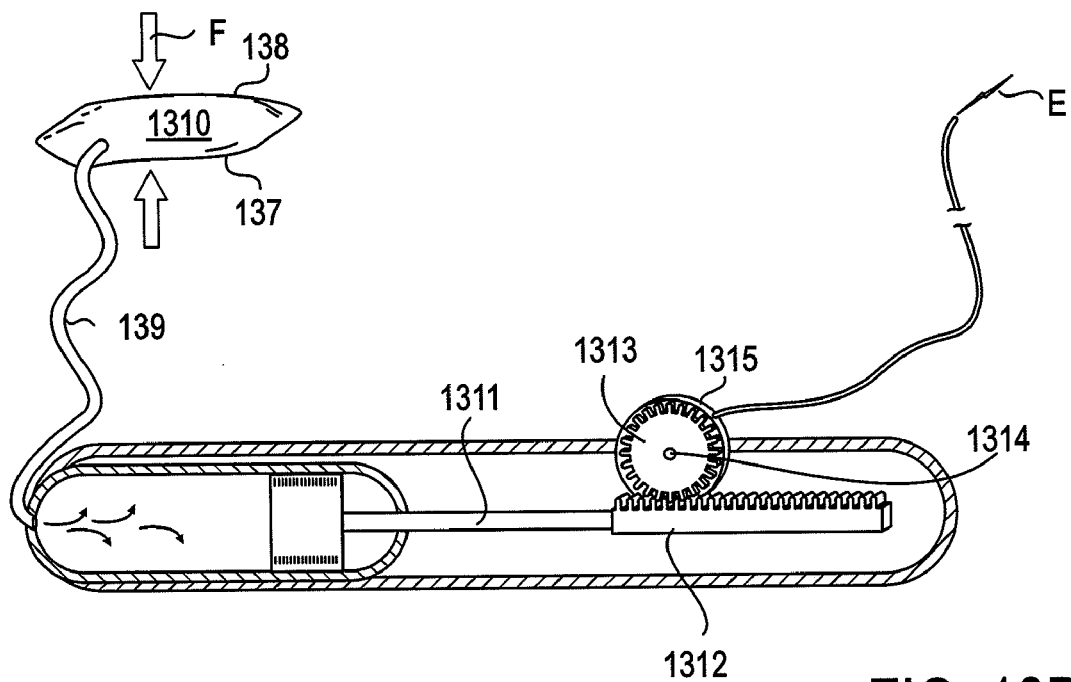

In a ninth, tenth, and eleventh embodiment, as shown in cross section in FIGS. 13A and 13B, 14 and 15 respectively, the compressible element 1310, as shown in FIG. 13A, may include a base 137 adapted and configured to be coupled to the first tissue layer, and a moveable surface 138, substantially opposite to the base, adapted and configured to be coupled to the second tissue layer. As shown in FIG. 13B, the force F applied from the two adjacent tissue layers to the compressible element moves the movable surface with respect to the base, thereby compressing the compressible element 1310.

The compressible element 1310 in this embodiment may be a bellows, a piston or other similar mechanical device. The compression of the compressible element 1310 displaces a fluid within the compressible element 1310 and causes a fluid pressure to activate the transducer. The transducer includes an electromagnetic generator 1315. In these embodiments, the power generator further includes a transmission component (rack 1312), that couples the compressible element to the transducer and that transforms the linear motion caused by the compressive force on the compressible element into an alternative motion or displacement, such as rotational displacement. A cyclic pressure (from the adjacent tissue layers, for example) on the compressible element 1310 compresses and inflates the compressible element (bellows, for example). The cyclic linear motion (v) and force (Ft) are transformed into a rotational motion ($\omega$) and torque (T) by the transmission component. The rotational motion drives the electromagnetic generator of the transducer, which in turn produces electrical power. The generated power may be stored in an accumulator, for example a capacitor or a rechargeable battery. The accumulator may be drawn upon from time to time to power a device such as a medical device.

The specific embodiment of the transmission component may take many forms. In the ninth embodiment, as shown in FIGS. 13A and 13B, the power generator includes a transmission component that transforms the linear motion caused by the compressive force into a rotational displacement with a rack and pinion configuration. As shown in FIGS. 13A and 13B, the fluid displaced from the compressible element (the vertical displacement caused by the transverse force F as shown in FIG. 13B) travels through a link 139 to a piston 1311, which is coupled to a rack 1312. The fluid displaced from the compressible element displaces the piston such that the rack moves linearly. The rack 12 runs into a pinion 1313 attached to a central axle 1314, which connects an electromagnetic generator 1315 to the pinion. Finally, the rotational velocity generated by the transmission component drives the electromagnetic generator, which transforms the rotational mechanical (torque and rotational displacement) energy into electrical energy E (potential difference and current). In an alternative variation, the compressible element may not include the fluid filled bellows, and rather, force F could directly couple to the piston and move the rack linearly.

Figure 14:
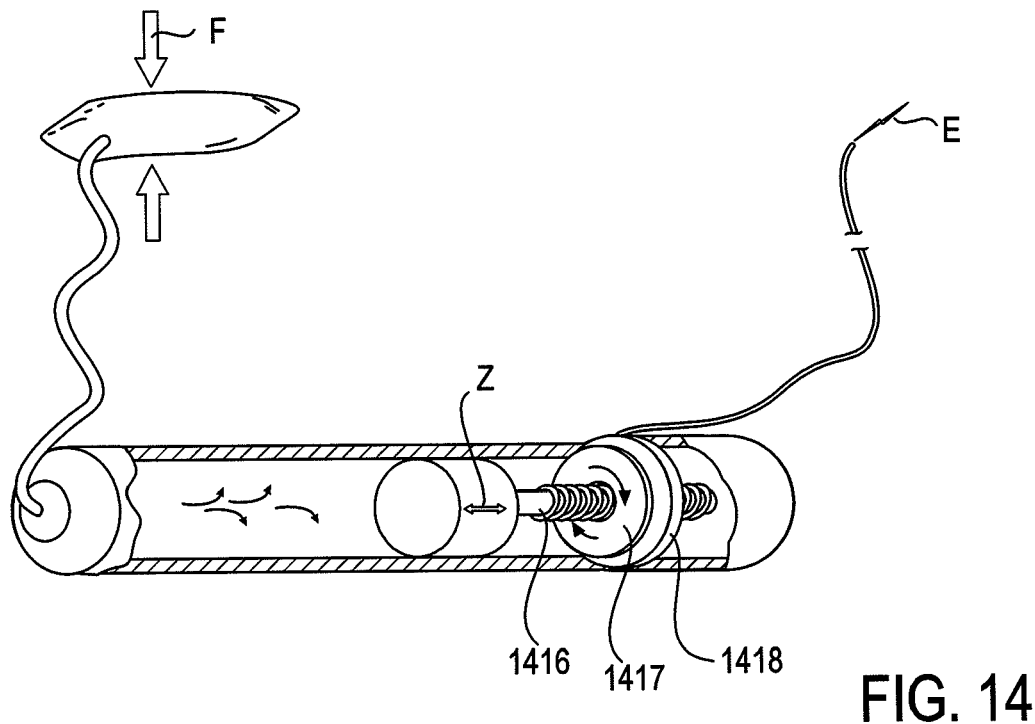

In the tenth embodiment, as shown in FIG. 14, the power generator includes a transmission component that transforms the linear motion caused by the compressive force into a rotational displacement with a threaded spindle configuration. As shown in FIG. 14, the fluid displaced from the compressible element (the vertical displacement caused by the transverse force F) travels through a link to a piston, which is coupled to a threaded spindle 1416 that runs into a threaded cylinder 1417. The rotational degree of freedom of the spindle is constrained and is allowed to move in z-direction only (as shown by arrow Z in FIG. 14). The threaded cylinder is allowed to turn and is not allowed to move in z-direction. The cylinder is attached to the main axle of the electromagnetic generator 1418. In an alternative variation, the compressible element may not include the fluid filled bellows, and rather, force F could directly couple to the piston and move the threaded spindle.

Figure 15:
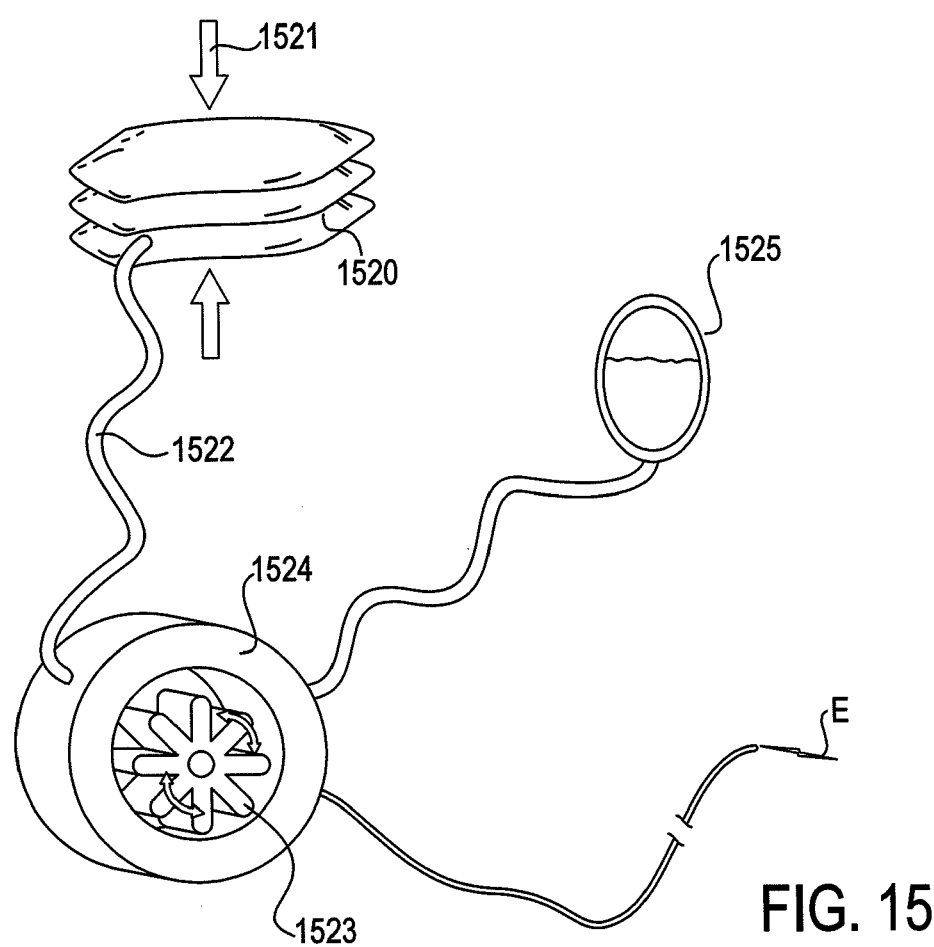

In the eleventh embodiment, as shown in FIG. 15, the power generator includes a transmission component that transforms the linear motion caused by the compressive force 1521 into a rotational displacement with a hydraulic system. As shown in FIG. 15, the fluid 1522 displaced from the compressible element 1520 travels through a link to a hydraulic system. The moving fluid actuates a wheel 1523 which in turn drives the electromagnetic generator 1524. The fluid is then returned to the compressible element, by the increased pressure in the pressure chamber 1525 and the generator is activated in the reverse direction.

Additional Elements

In some embodiments, the power generator for converting mechanical energy to electrical energy further includes insulated wires that function to conduct the electrical energy generated to an implanted electronic device or any other suitable device (implanted or not implanted) requiring power. The wires that carry the electrical energy generated by the transducer (such as the embodiment of the transducer having a variable capacitor) preferably connect with an electrical circuit (as described below). Additionally, as shown in FIGS. 8 and 9 for example, the electrodes 814 and 814' may terminate in tabs 822 and 822' respectively, which may be coupled to wires 824 and 824' respectively, which carry the generated electrical energy to a circuit (as shown by example in FIG. 16) that functions to condition the voltage generated by the transducer 812 to be used in an implanted medical device or any other suitable device that requires power. The wires 824 and 824' are preferably coiled conductors in an insulator 826, 826' made of silicone rubber or polyurethane suitable for long-term implantation.

In some embodiments, the implantable power generator for converting mechanical energy from a patient to electrical energy further includes a circuit that converts the electrical energy generated by the transducer of the power generator into energy usable to power a device.

Figure 16:
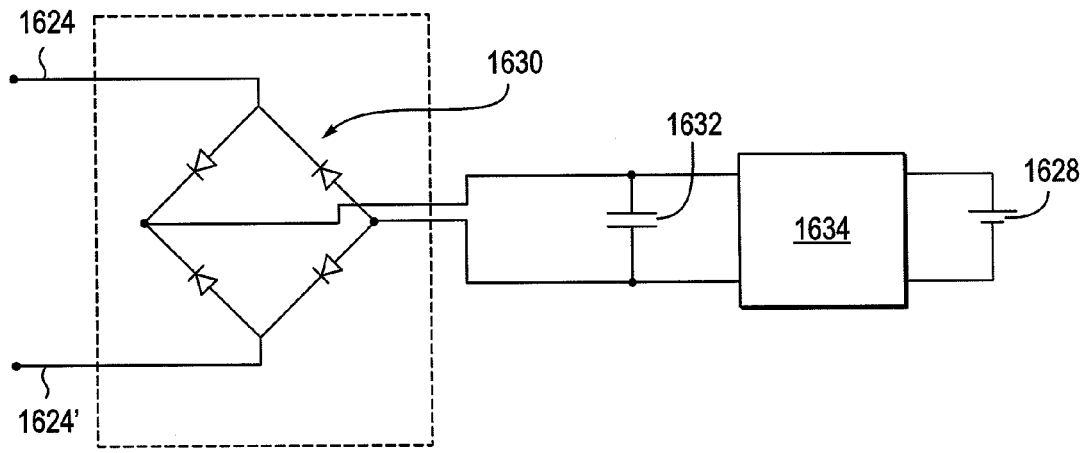
FIGS. 16-17 are schematic drawings of two variations of circuits of the power generator.

As shown in FIG. 16, in some embodiments, the implantable power generator includes a circuit, coupled to wires 1624 and 1624', that converts the electrical energy collected into a substantially DC voltage. For example, due to the cyclic nature of a muscle contraction, such as the muscle contractions from a masticatory process, the electric current may be roughly sinusoidal in nature. This may be particularly true in a power generator having an electromechanical or piezoelectrical transducer as illustrated in FIGS. 4-10 and 13-15. The electrical output of the transducer may therefore be applied to a full-wave rectifier which in turn may be used to charge a capacitor or rechargeable battery, or other storage device, to store the electrical energy. The circuit may use the generated voltage to charge a battery 1628. The battery may be used to power a pacemaker, defibrillator, neurostimulator, pump, or other implanted or non-implanted device. The inputs to the circuit, as shown, are wires 1624 and 1624' (which may be continuous with wires 824 and 824' respectively of FIG. 8, for example) that carry the generated electricity. The voltage waveform (as measured between the wires) may be an oscillating signal that varies with the muscle contraction of the patient. In the illustrative embodiment, the oscillatory voltage may be converted to a quasi-DC (direct current) voltage through the action of four diodes configured as a bridge 1630 and an input capacitor 1632 to store the DC voltage. The resultant DC voltage can range from below the battery voltage to above the battery voltage and generally needs to be conditioned by a voltage conditioning circuit 1634 before it can be used to charge the battery. A "buck-boost" circuit employing an inductor or a comparable switched capacitor scheme (see for example U.S. Pat. No. 6,198,645, which is incorporated in its entirety by this reference) in order to efficiently convert the variable voltage on the input capacitor to a voltage suitable for charging a battery. In some embodiments, the battery may be a rechargeable, but any other electrical energy storage devices may be used, such as a capacitor. In some embodiments, for example, the generated energy may stored in an accumulator (for example a capacitor or a rechargeable battery), as shown in FIG. 16, which may drawn upon from time to time to power a device such as a medical device.

Figure 17:
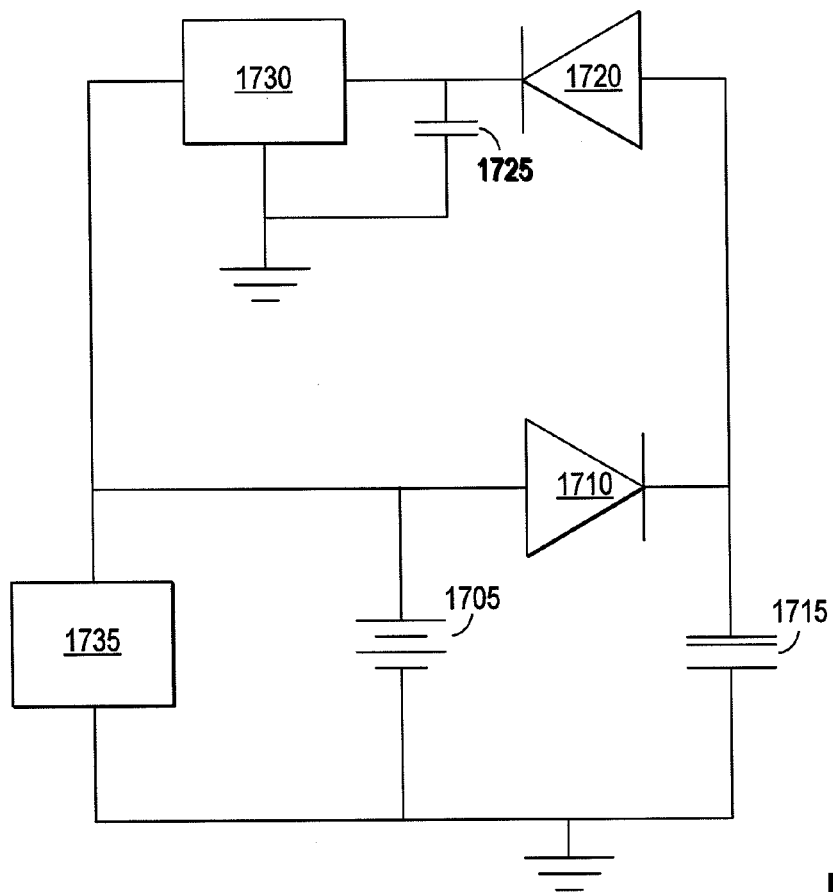

In a second variation, as shown in FIG. 17, a circuit can be used to store the electrical energy converted from mechanical energy by an electrostatic transducer (for example, as used in FIGS. 1-3 and 11-12). In this variation, a battery 1705 is connected through a diode 1710 to charge a variable capacitor 1715 (of the fourth embodiment, as shown in FIG. 11, for example) when its plates are close together. Another diode 1720 goes from the variable capacitor 1715 (which may be the electrostatic transducer—its capacitance changes as a result of pressure from contracting muscles) to a storage capacitor 1725 that accepts charge from the variable capacitor 1715 when its plates are further apart. A charging circuit 1730 allows the storage capacitor 1725 to charge the battery 1705 so that the battery 1705 can energize a circuit 1735 to perform useful operations. While a wide range of values are possible (and without limitation), a typical voltage range for the battery 1705 is 3 to 9 volts. The storage capacitor 1725 is typically in the range of 2 to 50 microfarads and typically operates at 1.5 to 4 times the battery voltage. The charging circuit 1730 typically utilizes a capacitive voltage or buck down-converter for energy efficiency. The variable capacitor 1715 typically operates in the range of 0.1 to 2.0 microfarads.

In some embodiments for example, the circuit may be located in position 110, as shown in FIG. 1A, may be coupled to the transducer, and may collect electrical energy from the capacitor of the transducer, for example, as the voltage transitions from a first voltage to a second voltage. In this embodiment, the plates of the capacitor may be electrically coupled to the circuit that collects electrical energy in the form of the voltage and/or charge on plates as the capacitance between these plates changes. As described above, in various embodiments of the power generator, the capacitance may change between the plates due to a phase change of dielectric fluid (for example FIGS. 1-2), due to the distance between the plates changing (for example FIGS. 3A, 3B, 11, and 1-2), due to the amount of dielectric fluid between the plates changing (for example FIGS. 3A and 3B), and/or due to any other mechanism.

The circuit of these embodiments may also function to pre-charge the plates of the capacitor so that the change in capacitance, results in a change in voltage. In operation, a low voltage (for example 2 to 5 volts) may be applied to the plates of the capacitor while the capacitance is comparatively high (for example, when the dielectric is in a liquid phase) and the circuit may then remove the charge (i.e. collect the generated electrical energy) from the capacitor while the capacitance is comparatively low (for example, when the dielectric is at least partially in a gas phase) and the voltage has increased. In some variations, the circuit may reside outside of the housing and/or outside of the patient all together.

In some embodiments, the power generator for converting mechanical energy to electrical energy further includes a storage device. In some embodiments, the storage device may be located in position 125, as shown in FIG. 1A. The storage device may be provided to store electrical energy generated by the transducer, and/or to further condition the electrical energy for use by an implantable medical device or other suitable device. The storage device may contain a storage element such as a rechargeable battery or capacitor, and associated electronic circuitry to manage charging and discharge of the storage element.

In some embodiments, the compressible element and the transducer (and any other additional electronics) may be housed within the same housing and/or implanted within the same implant location. Alternatively, the compressible element and the transducer (and any other additional electronics) may be housed in separate housings and/or implanted within different implant locations. The compressible element and transducer may therefore be coupled with a wire, wirelessly, hydraulically, or by any other suitable connection means. Further, in some embodiments, the compressible element may be coated with a hydrogel or thin polymer to elute a steroid or anti-proliferation agent (siromilus for example) to allow the compressible element to remain free of tissue ingrowth. The compressible element and the transducer, coupled to the compressible element, that converts mechanical energy from the compression of the compressible element to electrical energy may each be adapted and configured in one of several embodiments.

Implant Locations for an Implantable Power Generator

In some embodiments, an implantable power generator for converting mechanical energy from a patient to electrical energy includes a compressible element adapted and configured to be placed between two adjacent tissue layers of the patient. The compressible element may be compressed by a force applied from the two adjacent tissue layers to the compressible element. The implantable power generator includes a transducer, coupled to the compressible element, which converts mechanical energy from the compression of the compressible element to electrical energy. The implantable power generator may be designed to harvest mechanical energy from a patient, and more specifically to harvest mechanical energy from compressive forces resulting from muscle contraction and to convert this mechanical energy into electrical energy.

In some embodiments, the compressible element includes a base adapted and configured to be coupled to the first tissue layer, and a moveable surface, substantially opposite to the base, adapted and configured to be coupled to the second tissue layer. The force applied from the two adjacent tissue layers to the compressible element moves the movable surface with respect to the base, thereby compressing the compressible element.

In some embodiments, the compressible element is adapted and configured to be placed between two adjacent muscle layers of a muscle and to be compressed by a pressure generated by the muscle contracting. Intramuscular pressure tends to increase with muscle contraction and fall with muscle relaxation or extension, and is most pronounced in deep muscles and those situated against unyielding structures such as bone. Typical measurements under load include 15 kPa in the human supraspinatus muscle under load, and approximately 33 kPa in the human soleus muscle. A power generator such as that described here could be placed on, in, near, or within any of these or other muscle locations and/or between these muscles and an adjacent structure.

In addition, negative intra-muscular pressures during passive muscular extension, with amplitude on the order of one third of that of positive pressure during contraction, have been observed in rabbit tibialis anterior muscle. In some embodiments, the compressible element may recover from the compression during muscle relaxation or passive extension by utilizing these negative intra-muscular pressures. Alternatively, the compressible element may recover from the compression during muscle relaxation or passive extension by utilizing an elastic, resilient, or spring force or a similar intrinsic mechanism in the design to affect this recovery.

In some embodiments, the compressible element is adapted and configured to be placed between a muscle layer and an adjacent firm tissue layer of the patient and to be compressed by a pressure generated by the muscle contracting adjacent to the firm tissue layer. A firm tissue layer may include a bone or other suitable unyielding structures, such as bone, fascia, ligament, cartilage, or other non-contractile tissue. As used herein, any yielding is a relative term compared to the deflection properties of a specific power generator. Suitable unyielding tissues will vary depending upon location and power generator characteristics. Sub-muscular pressure tends to increase with muscle contraction and fall with muscle relaxation or extension. Sub-muscular pressures as high as 122 kPa have been measured in the temporal fossa of pigs during mastication.

The implantable power generator may be placed in a location most suitable for harvesting energy from pressure in the body and, in some embodiments, in a location most suitable to transmit usable energy to an implanted medical device that may be in the same implant location or in a separate location in the body. Transmission of energy from the implantable power generator to the medical device may be either wireless or over wires.

As shown in the following table, without limitation, three primary divisions of the body from which an implantable power generator may be used include the head, the torso and the limbs. From each of these locations an implantable power generator can be used to generate energy for and/or transmit energy to an implanted device to do useful work as shown in the example "applications" of the table.

In some variations, the type of medical device that may benefit from an implantable power generator, as described, may be related to the implant location in which the implantable power generator is implanted. For example, a neurostimulator used to stimulate a nerve within the head or neck of the patient and used in applications such as treating pain, depression, epilepsy, headache, and/or movement disorders, may benefit from an embodiment of the power generator where the power generator is implanted in the head of a patient, such as under, adjacent to, or within the temporalis muscle. A neurostimulator used to stimulate a nerve within the torso/back of the patient and used in applications such as treating pain or asthma may benefit from an embodiment of the power generator where the power generator is implanted in the torso of a patient, such as under or within a pectoral or gluteus maximus muscle. For further example, a pacemaker used to stimulate the heart of the patient and used in applications such as angina or heart failure may benefit from an embodiment of the power generator where the power generator is implanted in the torso of a patient, such as under or within a pectoral or gluteus maximus muscles. A neurostimulator used to stimulate a nerve within the torso, back, and/or limbs of the patient and used in applications such as treating foot drop may benefit from an embodiment of the power generator where the power generator is implanted in the limb(s) of a patient, such as under or within a bicep or quadriceps muscle.

TABLE 2

Exemplary implant locations and applications.

| Example power generator implant location | Example medical device implant location | Example target organ | Example application |
| --- | --- | --- | --- |
| Head: under or in the temporalis, masseter or other muscle in the head | under the scalp, cranially mounted, in the face, neck, intravascular, occipital | brain cortex, brain nuclei, brain stem, other brain structures, facial nerves, SPG, trigeminal nerves, occipital nerve, autonomic nerves in | pain, depression, epilepsy, headache, movement disorders, Alzheimer's, dementia, minimally conscious state, addiction, OCD, hearing disabilities, vision prosthesis, tinnitus, balance, obesity and metabolic disorders, addiction, learning, attention deficit |

TABLE 2-continued

Exemplary implant locations and applications.

| Example power generator implant location | Example medical device implant location | Example target organ | Example application |
|---|---|---|---|
| | | the head, carotid, tongue, hypoglossal nerve | disorders, hypertension, sleep apnea, acute stroke, stroke recovery, vasospasm, medication delivery, stem cell delivery |
| Torso: under or in the pectoral muscle, the abdominal or intracostal muscles, the gluteus maximus, the latissimus dorsi, or other torso muscle | pectoral, back, buttocks, abdominal, in or on the heart, intravascular, stomach, intestines, subcutaneous | vagus nerve, sympathetic nerve chain, spinal column, carotid, aorta, pulmonary artery renal artery, renal vein, hepatic artery, hepatic vein, stomach, intestine esophagus, trachea, bronchus, heart, bladder, pelvic nerves, splanchnic nerve, phrenic nerve, diaphragm, blood serum | pain, angina, depression, epilepsy, obesity and metabolic disorders, hypertension, apnea, asthma, COPD, other breathing disorders, reflux disorders, gastropareisis, heart failure, cardiac tachyarrhythmias, bradycardia, incontinence, sexual dysfunction, functional electrical stimulation, blood flow assist, glucose monitoring, glucose pump, medication delivery, |
| Limbs: Under or in a limb muscle (biceps, quadriceps, gastrocnemius, or other limb muscle) | Under or in a limb muscle. For example biceps, quadriceps, gastrocnemius, or other limb muscle. | peripheral nerve, motor nerve, sensory nerve | Foot drop, functional electrical stimulation, pain, prosthesis interface |

In some embodiments, the compressible element is adapted and configured to be placed between a muscle layer and an adjacent firm tissue layer of the patient and to be compressed by a pressure generated by the muscle contracting adjacent to the firm tissue layer and applying compressive loads against the firm tissue layer. A firm tissue layer may include a bone or other suitable unyielding structures. Submuscular pressure tends to increase with muscle contraction and fall with muscle relaxation or extension. The muscle may be muscle of the head (such as a temporalis muscle) a thorax muscle (such as the pectoralis major muscle), abdominal muscle (such as the rectus abdominis muscle), or lower torso muscle (such as the gluteus maximus muscle), the firm tissue layer may be firm structures of the head, thorax, abdomen or lower torso (such as bone, the anterior thoracic wall, ribs, anterior abdominal wall, gluteus medius, deep muscles of the lower extremity, hip bone), and the muscular contractions may occur during chewing, talking, walking, sitting, standing, exercising, grasping and any other body movements. The muscle, firm structure, muscle bundle, and muscular contractions may, however, be any suitable muscle, firm structure, and muscular contractions including manual activation achieved by pressing on the compressible element of the implanted generator.

In some embodiments, the muscle is a facial muscle (such as the masseter or temporalis muscle), the bony surfaces are preferably bony structures of the face (such as the temporal fossa, the mandibular angle, and/or the zygomatic arch), and the contractions occur during mastication, speech, and any other similar facial movements. The muscle, bony structure, and muscular contractions may, however, be any suitable muscle, bony structure, and muscular contractions including manual activation achieved by pressing on the compressible element of the implanted generator.

Figure 18A:
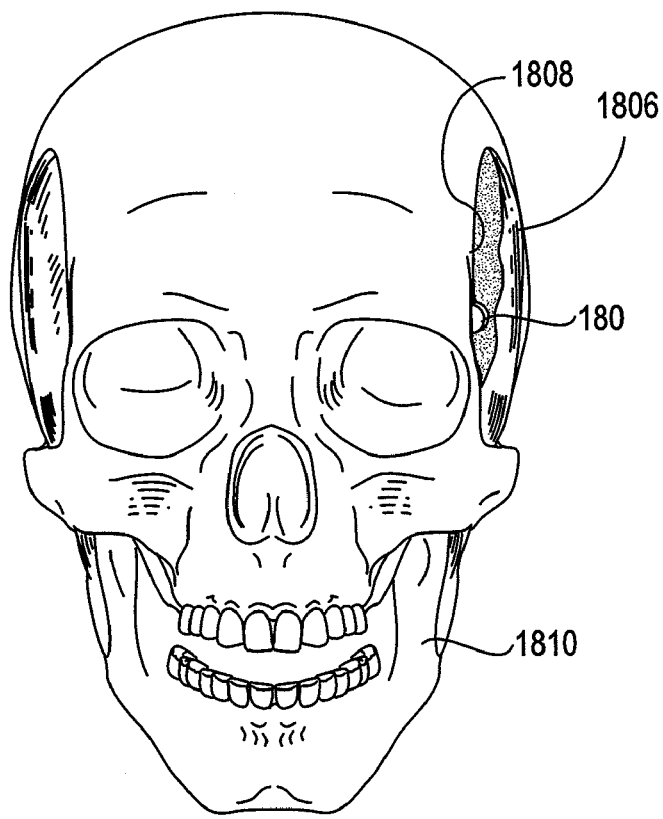
FIGS. 18A-18B are drawings of an implantable power generator implanted between a temporalis muscle layer and a firm tissue layer.
Figure 18B:
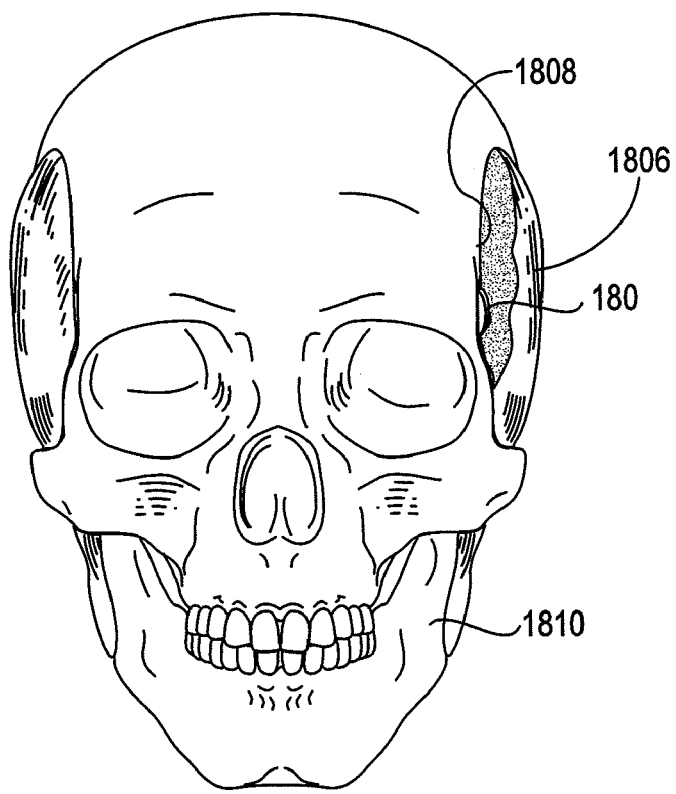

As shown in FIGS. 18A and 18B, in some embodiments, the implantable power generator 180 is implanted between a muscle layer and a bony layer. The compressible element may be implanted under the temporalis muscle 1806 that inserts into the temporal bone 1808 at one end and connects to the coronoid process of the mandible 1810 at the other. In this variation, as an example, the compressible element may have a diameter of 5 mm to 5 cm, such that it may be implanted under the temporalis muscle 1806 between the connection points at the temporal bone 1808 and the coronoid process of the mandible 1810. In some embodiments for implantation under the temporalis muscle, the compressible element may include a base adapted and configured to be coupled to the temporal bone (i.e. having a compatible shape and convexity to lie substantially flush against the bone), and a moveable surface, substantially opposite to the base, adapted and configured to be coupled to the temporalis muscle (i.e. having a compatible shape to deform under the compressive loads of the temporalis muscle against the bone). In some embodiments, the movable surface preferably moves a distance within the range of 0.5 mm to 4.0 mm under the compressive loads of the temporalis muscle against the bone. As shown in FIG. 18A, the temporalis muscle is comparatively relaxed and the compressible element is in an equilibrium (not compressed) position (shown as a nearly round in cross-section in FIG. 18A). FIGS. 18A and 18B show one illustrative implant location of the compressible element. It should be noted that the compressible element, in this embodiment, may alternatively be positioned in other suitable locations. When the temporalis muscle 1806 contracts, as shown in FIG. 18B, the mandible 1810 advances towards the temporal bone 1808. Under these circumstances, the temporalis muscle provides a compressive force (in some cases a compressive force of 10 to 20 pounds per square inch, for example) against the temporal bone and the compressible element is compressed into an activated (compressed) position (shown as an elongated, oval cross-section in FIG. 18B). The action of the temporalis muscle during speech and chewing provides a repetitive compression cycle that is received by the compressible element and converted by the transducer of the implantable power generator to generate electrical energy.

Figure 19:
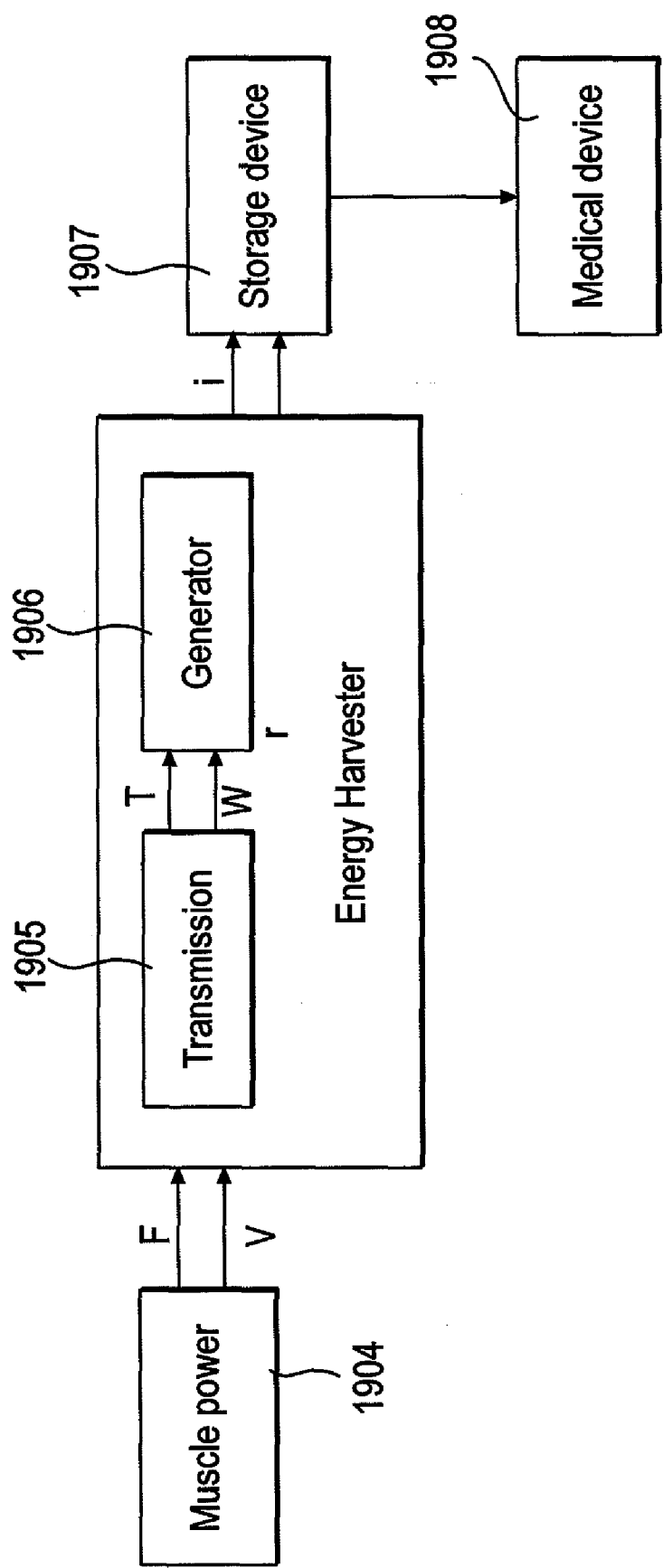
FIG. 19 is a schematic drawing of an embodiment of an implantable power generator.

As shown schematically in FIG. 19, an embodiment of the power generator includes a compressible element (not shown) and a transducer. In this embodiment, the transducer includes a generator 1906 (such as an electromagnetic generator). The power generator of this embodiment further includes a transmission 1906 that couples the compressible element to the transducer. As shown schematically in FIG. 19, a muscle power 1904 creates a linear motion (v) and a transverse force (F). During mastication for example, the axial force in the fiber direction of the temporalis muscle bundle causes a transverse force (F) in the direction perpendicular to the curved temporalis bone. The transverse force (F) and the contact area between the muscle bundle and the bone creates a normal pressure against the bone. The magnitude of the pressure is directly proportional to the axial force. In the case of the masticatory process the axial force will vary with the chewing action and cycle between a minimum level larger than or equal to zero and a maximum level. The associated pressure therefore, also exhibits a cyclic pattern.

In one embodiment of the implantable power generator, the compressible element is placed in between the muscle bundle and the fossa. The cyclic pressure (from muscle power 1904) provides a cyclic linear motion (v) and force (F), which are transformed, in this embodiment (similar to an embodiment as shown in FIGS. 13A-15, for example) into a rotational motion (ω) and torque (T) by means of a transmission 1905. The transmission is coupled to the compressible element. The muscle power, in some embodiments, may be applied to the compressible element to compress and inflate the compressible element. The rotational motion (the output from the transmission) drives a generator component 1906 of the transducer which in turn produces electrical power. The generated power is stored in a storage device 1907 (for example a capacitor or a rechargeable battery) which is drawn upon from time to time to power a medical device 1908.

Figure 20A:
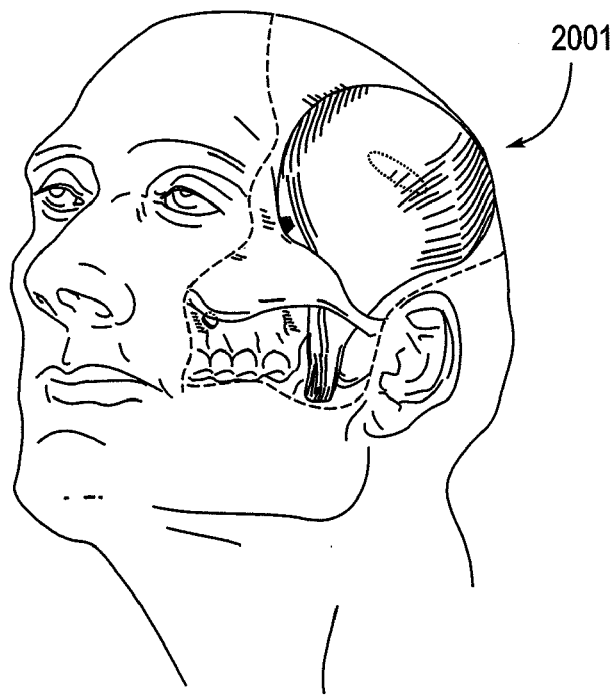
FIGS. 20A-20B are drawings of an implantable power generator implanted between a temporalis muscle layer and a firm tissue layer.
Figure 20B:
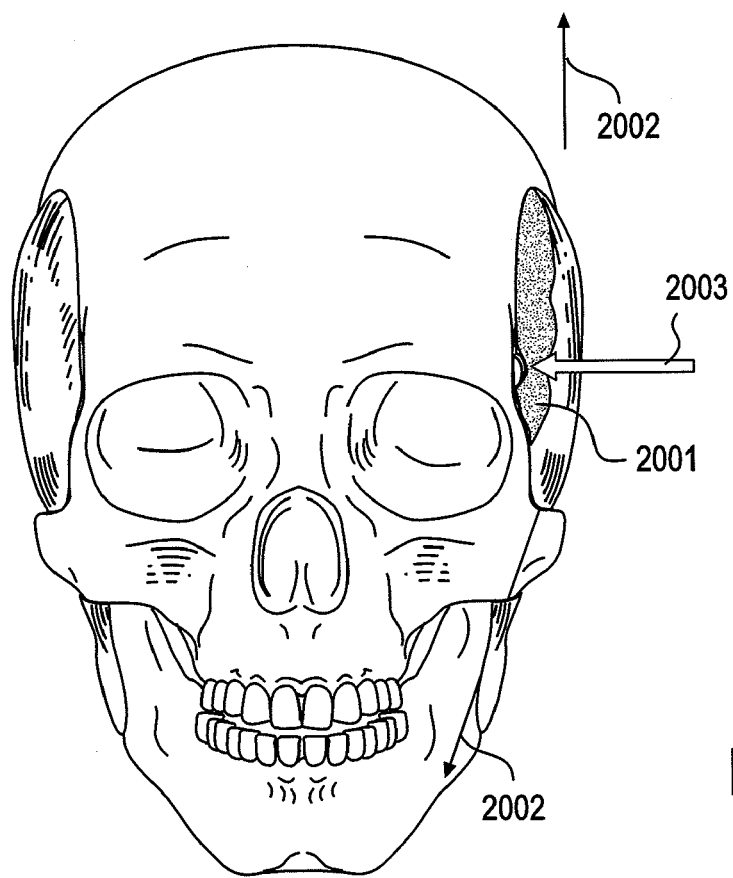

As shown in FIG. 20A, an implantable power generator 2001 may be inserted under the temporalis muscle close to the temporal fossa, such that one side of the device is supported by the hard surface of the fossa. The incision direction and location necessary for the deployment of the implantable power generator have been chosen such as to not compromise the structural integrity of the muscle that connects the coronoid process of the mandible to the superior temporalis line. As shown in FIG. 20B, the anatomy of the human skull at the location of the temporalis muscle is such that the axial force 2002 exerted by the muscle gives rise to a transverse component 2003, perpendicular to the temporal fossa. This transverse force 2003, acts on the compressible element as a compressive force. In addition, when the temporalis muscle is under tension, the cross section of the muscle increases, thereby increasing the pressure against the fossa.

Figure 21A:
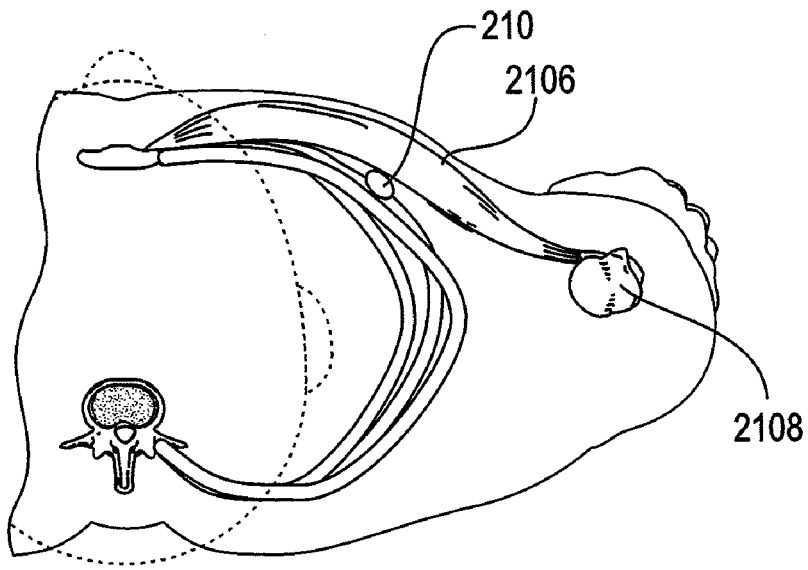
FIGS. 21A-21B are drawings of an implantable power generator implanted between a pectoralis major muscle layer and a firm tissue layer.
Figure 21B:
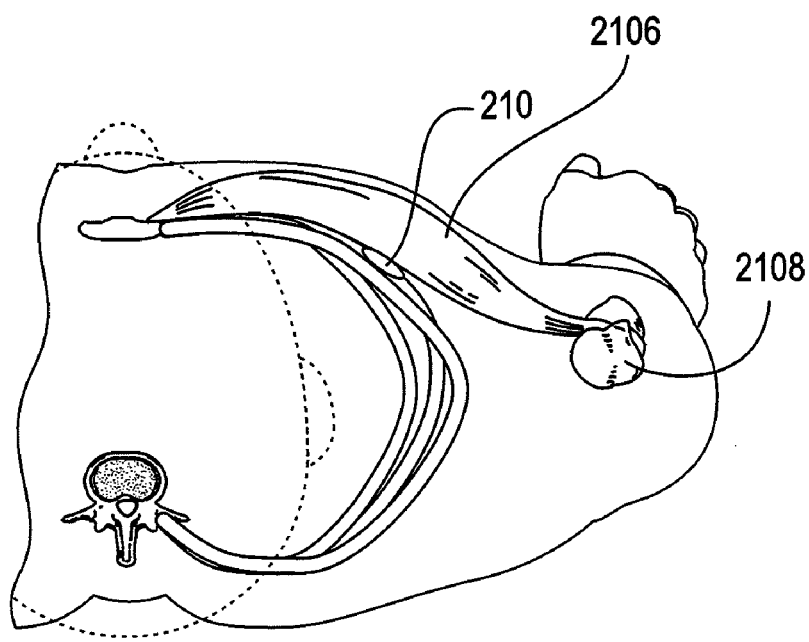

As shown in FIGS. 21A and 21B, the compressible element of implantable power generator 210 may be implanted between a muscle and a firm body structure. The implantable power generator is preferably implanted under the pectoralis major muscle 2106 that inserts into the humerus bone 2108 at one end stretching across the anterior thoracic wall 2116 and connects to the sternum 2114 and the clavicle bone and cartilages of upper ribs (not shown) at the other. In this variation, as an example, the compressible element may have a diameter of 5 mm to 8 cm, such that it may be implanted under the pectoralis major muscle 2106 between the connection points at the humerus bone 2108 and the sternum 2114. In some embodiments for implantation under the pectoralis major muscle, the compressible element may include a base adapted and configured to be coupled to the anterior thoracic wall 2116 (i.e. having a compatible shape and concavity to lie substantially flush against the wall and/or ribs), and a moveable surface, substantially opposite to the base, adapted and configured to be coupled to the pectoralis major muscle (i.e. having a compatible shape to deform under the compressive loads of the pectoralis major muscle against the bone, ligament, etc.). In some embodiments, the movable surface preferably moves a distance within the range of 0.5 mm to 8 mm under the compressive loads of the pectoralis major muscle against the anterior thoracic wall. The pectoralis major muscle 2106 is comparatively relaxed and the compressible element is in an equilibrium position (shown as a nearly round in cross-section in FIG. 21A). When the pectoralis major muscle contracts, as shown in FIG. 21B, the humerus 2108 advances towards the sternum 2114. Under these circumstances, the pectoralis major muscle provides a compressive force against the anterior thoracic wall 2116 and the implantable power generator and moves the compressible element into an activated (compressed) position (shown as an elongated, oval cross-section in FIG. 21B). The action of the pectoralis major muscle during walking and other movements provides a repetitive compression cycle that is converted by the transducer of the implantable power generator to generate electrical energy.

Figure 22:
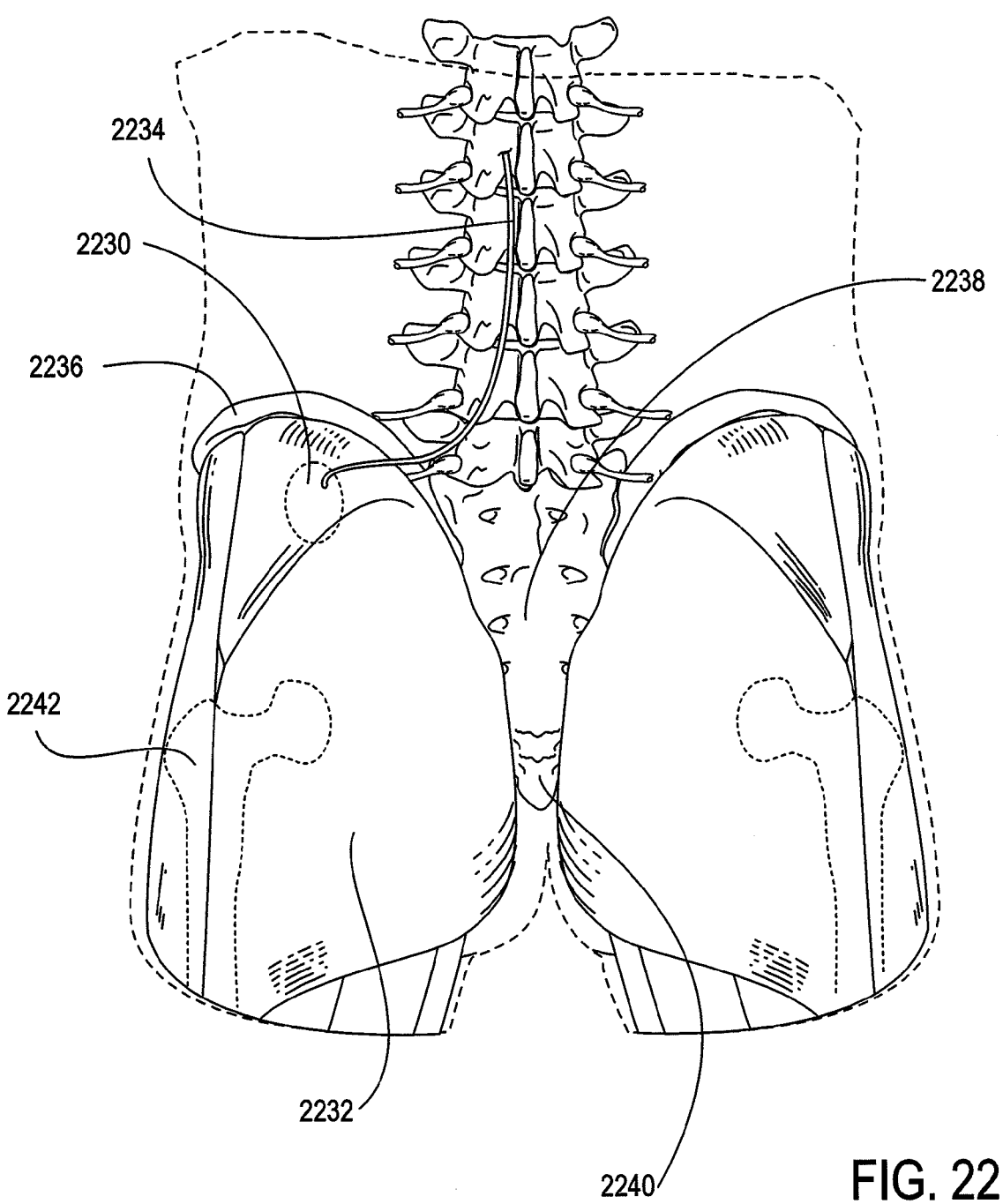
FIG. 22 is a drawing of an implantable power generator implanted between a gluteus maximus muscle layer and a firm tissue layer.

In some embodiments, as shown in FIG. 22, the implantable power generator may be implanted under (or within, as described below) an abdominal muscle or lower torso muscle such as the gluteus maximus muscle 2232. The gluteus maximus muscle arises from the bones and ligaments of the pelvis 2236, sacrum 2238, and coccyx 2240 and inserts into the bone and ligament of the femur 2242. When the gluteus maximus muscle contracts, the pelvis advances towards the femur. Under these circumstances, compressive forces within the gluteus maximus muscle are transmitted to the implantable power generator and move the compressible element into an activated (compressed) position.

In some embodiments, the compressible element is adapted and configured to be placed between two adjacent muscle layers of the muscle and to be compressed by a pressure generated by the muscle contracting. Intramuscular pressure tends to increase with muscle contraction and fall with muscle relaxation or extension, and is most pronounced in deep muscles and those situated against unyielding structures such as bone.

Figure 23A:
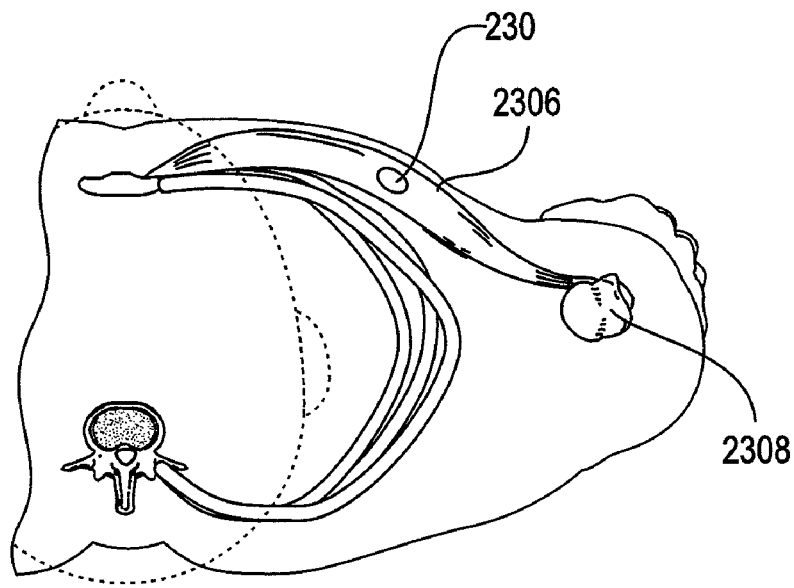
FIGS. 23A-23B are drawings of an implantable power generator implanted within a pectoralis major muscle.
Figure 23B:
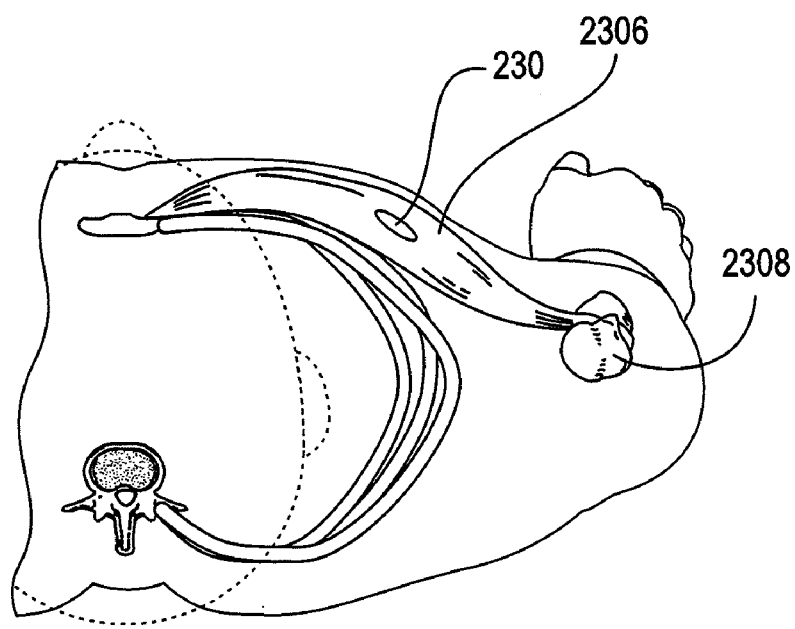

In another preferred embodiment the implantable power generator is within at least one muscle bundle where the implantable power generator may be exposed to cyclical flexing, bending and/or compressive forces. As shown in FIGS. 23A and 23B the implantable power generator is implanted within the pectoralis major muscle 2306. In this variation, as an example, the compressible element may have a diameter of 5 mm to 8 cm, such that it may be implanted within the pectoralis major muscle 2106 between the connection points at the humerus bone 2108 and the sternum 2114. In some embodiments for implantation within the pectoralis major muscle, the compressible element may include a base (or first movable surface) adapted and configured to be coupled to a first layer of the pectoralis major muscle (i.e. having a compatible shape to deform under the compressive loads from the contraction of the pectoralis major muscle), and a second moveable surface, substantially opposite to the base (or first movable surface), adapted and configured to be coupled to the second layer of the pectoralis major muscle (i.e. having a compatible shape to deform under the compressive loads from the contraction of the pectoralis major muscle). In some embodiments, at least one of the movable surfaces and/or in combination preferably move a distance within the range of 0.5 mm to 8.0 mm under the compressive loads from the contraction of the pectoralis major muscle. The pectoralis major muscle 2306 is comparatively relaxed and the compressible element shown in FIG. 23A is in an equilibrium (not compressed) position (shown as a nearly round in cross-section in FIG. 23A). When the pectoralis major muscle contracts, as shown in FIG. 23B, the humerus 2308 advances towards the sternum 2314 and the clavicle bone and cartilages of upper ribs (not shown). Under these circumstances, compressive forces within the pectoralis major muscle are transmitted to the implantable power generator and the compressible element moves into an activated (compressed) position (shown as an elongated, oval cross-section in FIG. 23B).

The mechanical energy harvested may alternatively be generated directly by the movement of muscle relative to bone and/or relative to the implantable power generator such that the implantable power generator flexes or bends rather than, or in addition to, being compressed. The mechanical energy harvested may further alternatively be generated by an external force applied to the muscle, bone, and/or implantable power generator. For example, a patient may apply pressure to their temple or any other suitable location over the implanted generator to manually compress the compressible element.

Methods for Generating Power

In some embodiments, a method for generating power by converting mechanical energy from a patient to electrical energy includes the steps of positioning a compressible element of an implantable power generator in an anatomical site, defined by a first tissue layer and a second, opposite tissue layer, within the patient; receiving a pressure applied by the two adjacent tissue layers with the compressible element thereby compressing the compressible element; and converting mechanical energy from the compression of the compressible element to electrical energy. The method may be designed to harvest mechanical energy from a patient, and more specifically to harvest mechanical energy from muscle contraction and to convert this mechanical energy into electrical energy. In some embodiments, the electrical energy generated may be used to power a medical device and, more specifically, to power an implantable medical device such as a neurostimulator or a cardiac pacemaker. The method implantable power generator may be alternatively used in any suitable environment and for any suitable reason.

In some embodiments, the positioning step further includes positioning the compressible element between a firm tissue layer and a muscle layer, and the receiving step further includes receiving a pressure generated by the muscle contracting adjacent to the firm tissue layer. In some embodiments, the positioning step further includes positioning the compressible element between muscle layers within a muscle and the receiving step further includes receiving a pressure generated by the muscle contracting. In some embodiments, the positioning step further includes creating an incision into a muscle bundle, between two muscle bundles, or between a muscle and a bone to access a virtual space in which the implantable power generator may be implanted.

In some embodiments, the method further includes the step of storing the electrical energy. In some embodiments, the method further includes the step of powering a medical device with the electrical energy, while in some embodiments, the method further includes the step of requesting electrical energy from the storage device to power the medical device.

In some embodiments, the method further includes the step of measuring, tracking, evaluating, and/or monitoring muscle movements of a patient to determine an appropriate implant location. The implant location may be chosen based on characteristics of the patient, such as patient size, patient weight, muscle strength, muscle configuration, etc. or may be chosen based on power generator characteristics such as size, sensitivity to pressure and/or force, etc. For example, a temporalis muscle and a pectoralis major muscle might be monitored to determine the contraction strength of each muscle and/or the ideal placement under, adjacent to, and/or within that muscle. The implant site may then be chosen based on this information and/or the requirements of the power generator and/or the medical device to which it is supplying power.

Systems for Generating Power

Figure 24:
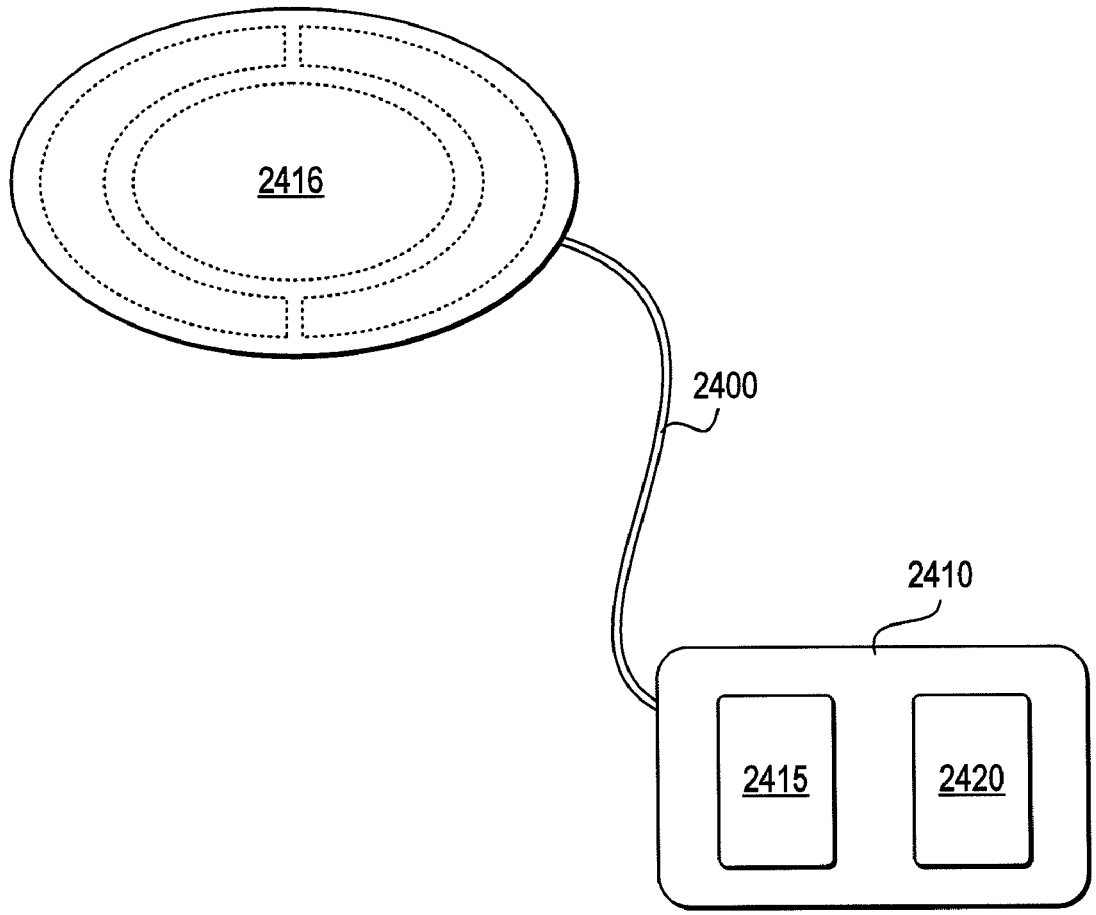
FIG. 24 is a drawing of an embodiment of a system for powering a medical device.

In some embodiments, as shown in FIG. 24, a system for powering a medical device includes an implantable power generator 2416 for converting mechanical energy from a patient to electrical energy, a storage device that collects electrical energy from the transducer, a medical device 2410 coupled to the storage device that receives electrical energy from the storage device. In some embodiments, the implantable power generator includes a compressible element adapted and configured to be placed between two adjacent tissue layers of the patient and to be compressed by a force applied from the two adjacent tissue layers to the compressible element, and a transducer, coupled to the compressible element, that converts mechanical energy from the compression of the compressible element to electrical energy. The system may be designed to harvest mechanical energy from a patient, and more specifically to harvest mechanical energy from muscle contraction and to convert this mechanical energy into electrical energy. In some embodiments, the electrical energy generated may be used to power a medical device and, more specifically, to power an implantable medical device such as a neurostimulator or a cardiac pacemaker. The system may be alternatively used in any suitable environment and for any suitable reason.

For example, as shown in FIG. 24, the implantable power generator 2416 may be implanted in a suitable region and may be connected by a flexible cable 2400 (or wirelessly connected) to an implantable system 2410, powering for example, a stimulating module 2420 and microprocessor 2415. The cable 2400 carries at least electrical power from the implantable power generator to the system 2410, but may also carry control or diagnostic signals from and to the generator.

The electrical energy generated by the implantable power generator may power a device such as a neurostimulator, pacemaker, defibrillator, pump, battery, or other implanted or external device. In some embodiments, the device may be a neurostimulator that may be implanted in a patient's face, head, or neck. For example, the neurostimulator may be a therapeutic device that stimulates a target nerve. The target nerve may be the trigeminal nerve, the maxillary nerve, the vidian nerve, the pterygopalatine ganglion (also known as the sphenopalatine ganglion), or any other suitable nerve. In some embodiments, the neurostimulator stimulates the target nerve or nerves to treat pain, headaches, migraine, and/or autonomic nerve imbalance disorders, but the neurostimulator may stimulate the nerve to treat any other suitable symptom, disease, or disorder or may stimulate the nerve for any other suitable reason.

Figure 25A:
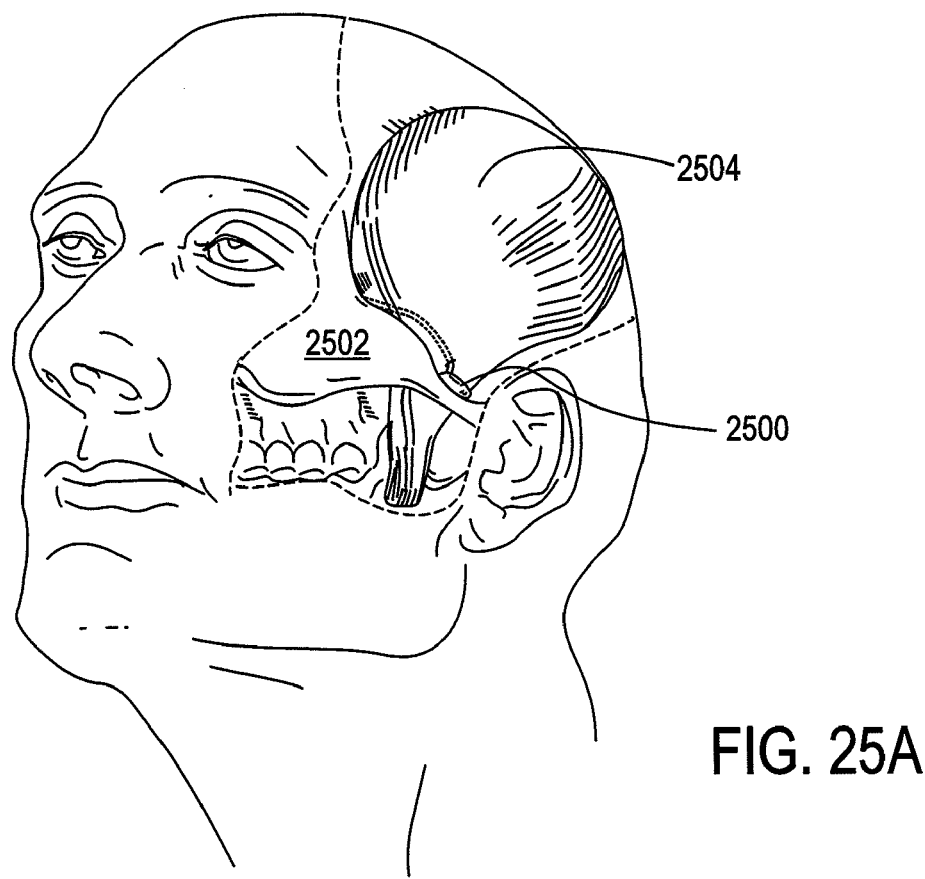
FIGS. 25A-25B are drawings of an embodiment of a system for powering a medical device implanted in a head of a patient.
Figure 25B:
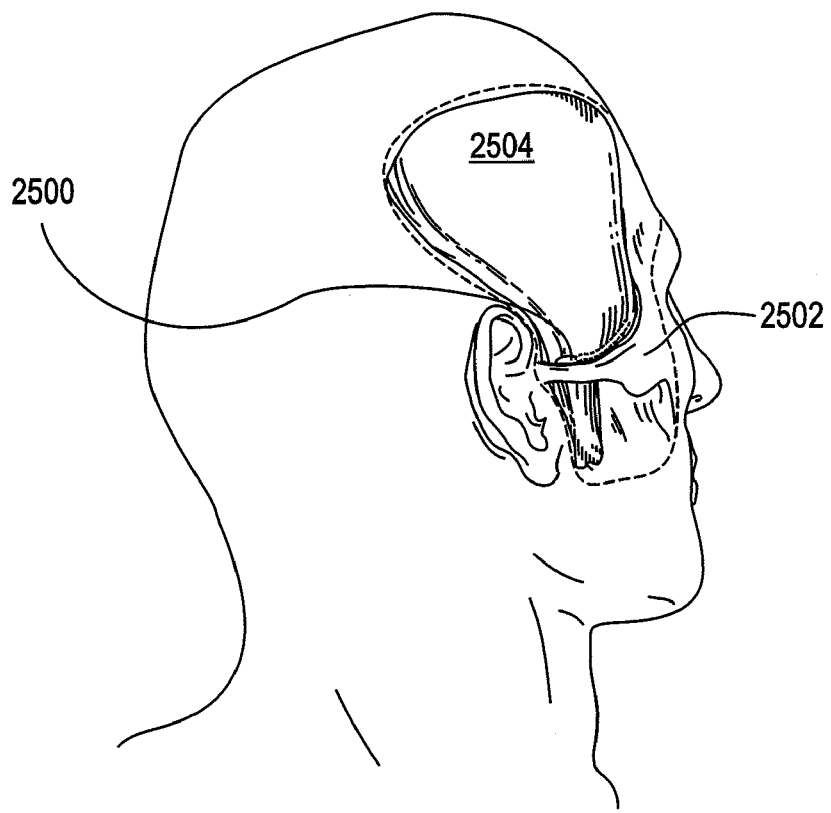

The implantable power generator may be incorporated into the neurostimulator, but may alternatively be coupled to the neurostimulator in any suitable fashion. As shown in FIGS. 25A and 25B, the neurostimulator 2500 may be implanted to originate at the top of the zygomatic arch 2502 and descend under the temporalis muscle 2504 towards its final target the pterygopalatine ganglion (not visible).

In some embodiments, the electrical energy generated by the implantable power generator powers a pulse generator such as a pacemaker, cardioverter, defibrillator, cardiac resynchronization therapy (CRT) device, or any other cardiac rhythm management (CRM) device, as well as combination devices that provide more than one of these therapy modalities to a subject, such as a CRT-ICD device, or a pain management device such as a spinal cord stimulator (SCS) device. Alternately, the powered device may be a neurostimulator, pump, battery, monitor such as a glucose monitoring device for diabetes, or other implanted or external device. CRT-ICD devices are intended to serve patients having a history of moderate to severe heart failure or for patients with a history of previous ventricular arrhythmia episodes. SCS devices are intended to serve patients with a history of pain in the lower extremities, upper extremities, or chest wall which arise from post laminectomy syndromes, failed back syndromes, chronic lesional pain syndrome, or other disorders leading to pain.

Figure 26:
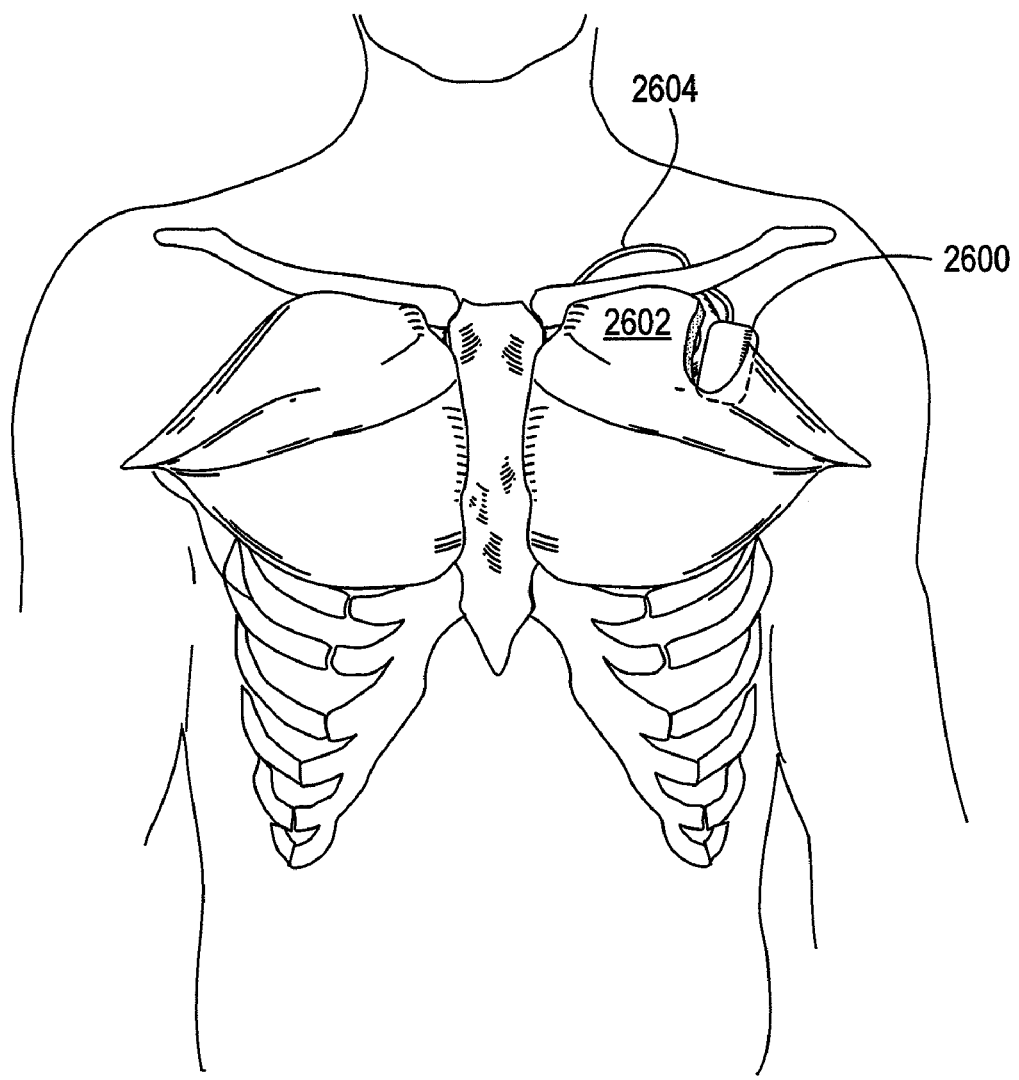
FIG. 26 is a drawing of an embodiment of a system for powering a medical device implanted in a torso of a patient.

As shown in FIG. 26, in some embodiments, the implantable power generator may be incorporated into the same housing of the pulse generator 2600. When the pulse generator 2600 is a CRT/ICD the pulse generator may be implanted under or within a thorax muscle such as the pectoralis major muscle 2602. In some embodiments, at least one lead wire 2604 connects to the pulse generator 2600 and carries electrical signals comprising at least one of sensed electrical activity or electrical stimulation near a body area such as the heart (not shown). Alternatively, the pulse generator 2600 may be wirelessly coupled to the implantable power generator.

In some embodiments, as shown in FIG. 22, when the pulse generator 2230 is a SCS the pulse generator may be implanted under or within an abdominal muscle or lower torso muscle such as the gluteus maximus muscle 2232. The gluteus maximus muscle 2232 arises from the bones and ligaments of the pelvis 2236, sacrum 2238, and coccyx 2240 and inserts into the bone and ligament of the femur 2242. A lead wire 2234 connects to the pulse generator 2230 and carries electrical signals comprising at least one of sensed electrical activity or electrical stimulation near a body area such as the spinal cord. In alternative embodiments of the present invention, the implantable power generator and pulse generator are in different housings, the implantable power generator and pulse generator connected by means of insulated wires, or the implantable power generator may transmit power wirelessly to the pulse generator. Power may be transmitted wirelessly in the form of electromagnetic radiation (including without limitation, radio waves, microwaves, and infrared, ultraviolet and visible light) or ultrasound or conducted electricity.

Figure 27:
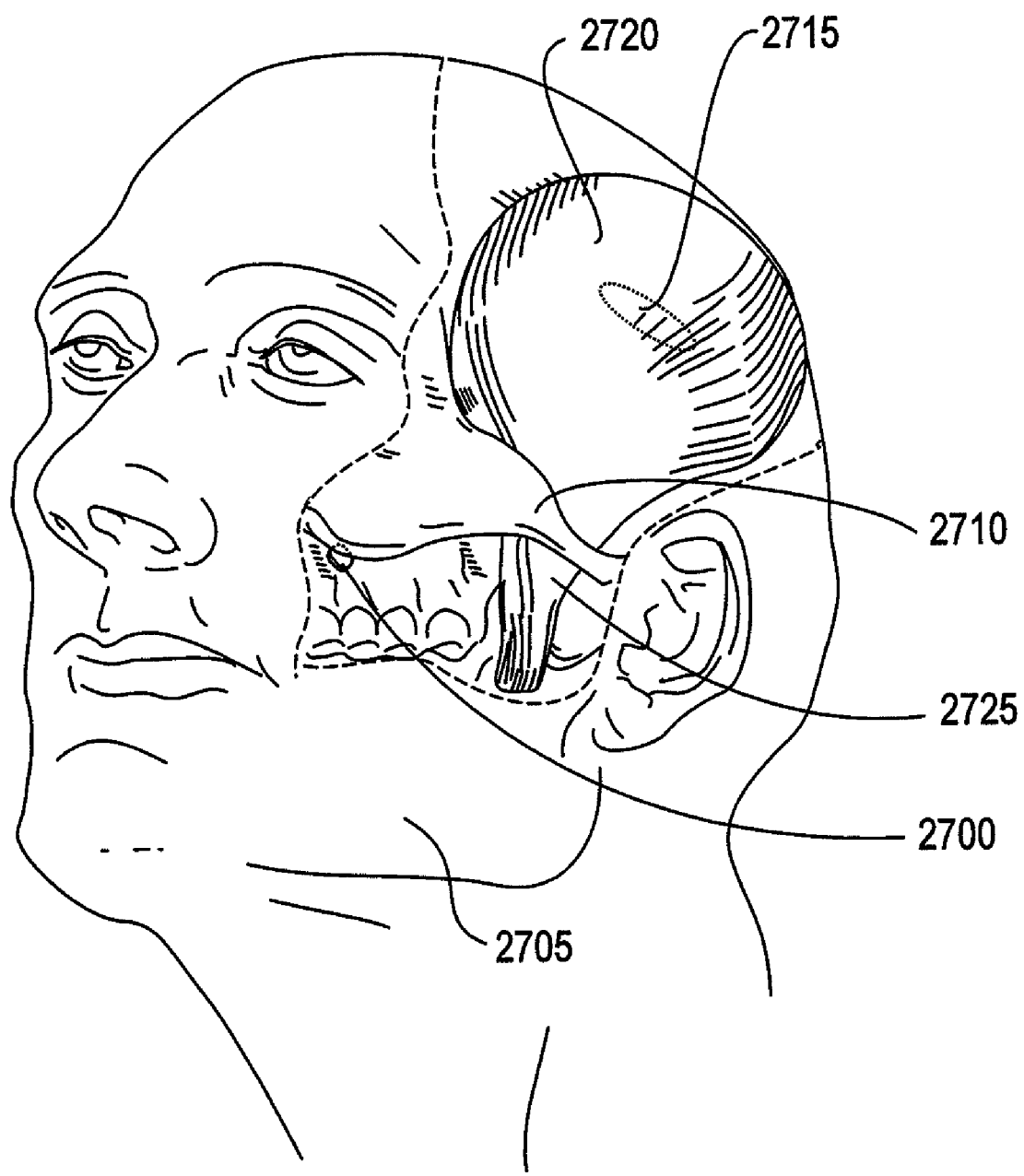
FIG. 27 is a drawing of an embodiment of a system for powering a medical device implanted in a torso of a patient.

In some embodiments, as shown in FIG. 27, the medical device may be a neurostimulator 2700, implanted deep in the face near the sphenopalatine ganglion (SPG). It may be behind the zygomatic arch 2710 or other suitable locations, such as coupled to the mandible 2705. The neurostimulator may be sized and configured such that it can be installed through mucosa under the cheek or the palatine foramen in the roof of the mouth, or though other minimally invasive approaches such as injected though the mandibular notch by a large bore needle. The implantable power generator 2715 may be implanted under, adjacent to, or within the temporalis muscle 2720. Alternatively, the implant location may be under, adjacent to, or within the masseter muscle 2725, for example. In its position under the temporalis muscle, the implantable power generator converts cyclical pressure produced by the temporalis muscle into electricity that it then transmits through the face of the patient to the implanted neurostimulator, thereby providing the neurostimulator with power to stimulate the SPG, or other nerves, for therapeutic purposes. Because the neurostimulator is being powered by the implantable power generator, it can be smaller than otherwise possible if it needed to include a battery.

In this embodiment, the neurostimulator is near a target stimulation site, within, under, or adjacent to the SPG. However, it is to be appreciated that the compressive forces of the temporalis or masseter muscle harvested by the implantable power generator could power a neurostimulator in a variety of locations in the head or neck or other locations to treat a variety of disorders as shown in Table 2. A power generator in such an implant location could be used to provide power to therapy systems, including, for example without limitation cochlear implants to treat hearing disorders; neurostimulators in or on the skull to treat a variety of brain disorders including depression, movement disorders, and epilepsy; neurostimulators near the carotid to treat hypertension; neurostimulators near the hypoglossal nerve to treat sleep apnea; neurostimulators near the occipital, supraorbital or other nerve to treat headache and other pain; and/or retinal implants to treat vision disorders. Furthermore, drug delivery systems may also benefit by being powered by an implantable power generator.

Figure 28:
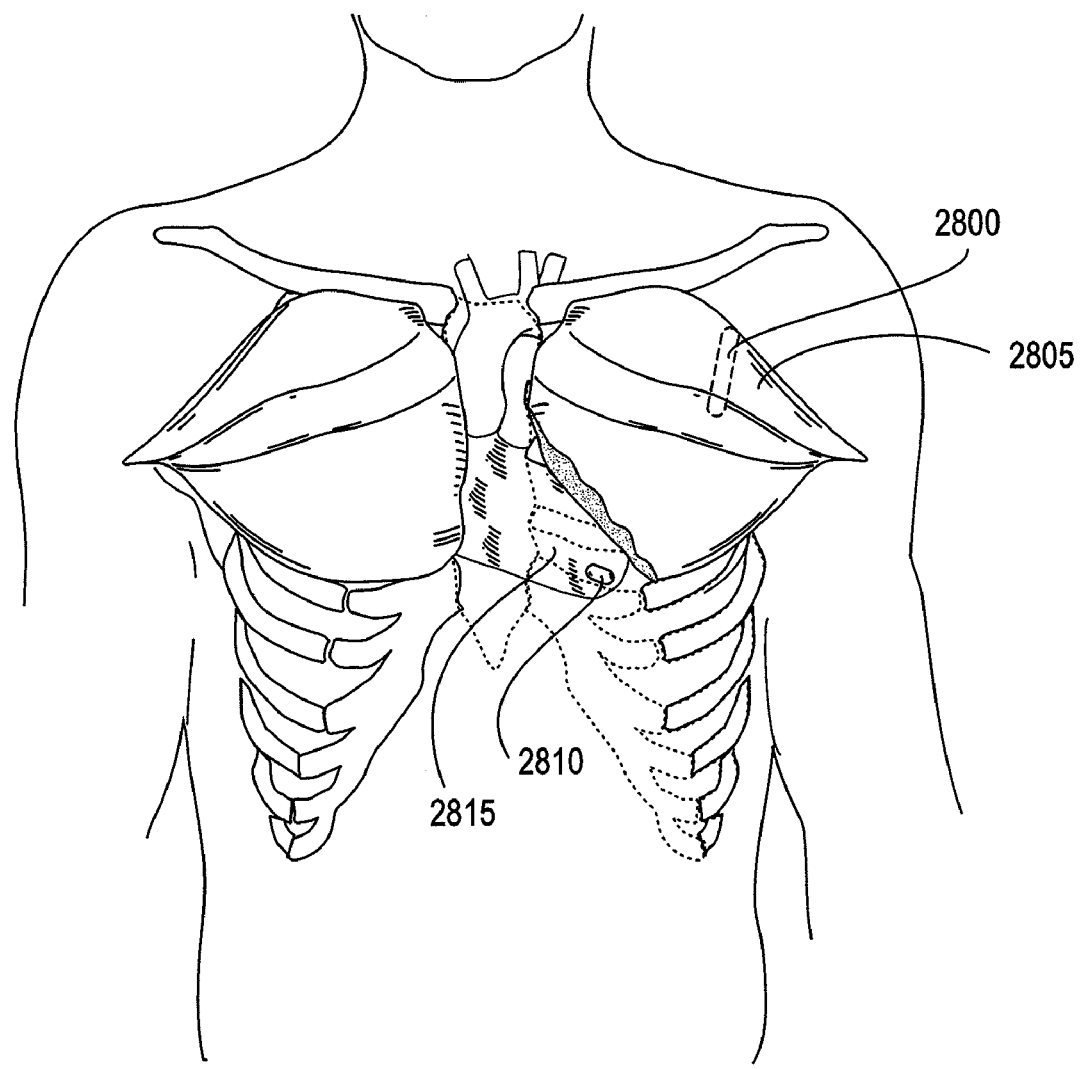
FIG. 28 is a drawing of an embodiment of a system for powering a medical device implanted in a torso of a patient.

In some embodiments, as shown in FIG. 28, an implantable power generator 2800 may be implanted in or under the pectoral muscle 2805 to harvest energy from the cyclical pressure produced by the pectoral muscle 2805. The torso includes other suitable locations for an implantable power generator including without limitation the latissimus dorsi, the gluteus maximus and abdominal muscles. In this example a leadless heart pacemaker 2810 is installed on the surface of the heart 2815. Since the leadless heart pacemaker does not need a large battery it can be made very small and installed on the surface of the heart in some embodiments. Many other medical devices in the torso can be made smaller and benefit from not having a battery by having energy transmitted to them. For example and without limitation cardiac pacemakers (with or without leads, positioned either on, in, or adjacent to the heart), cardiac defibrillators, neurostimulators (conventional with leads, or leadless including intravascular designs), drug pumps, and diagnostic devices including blood glucose monitors.

The implantable power generators (2715 and 2800) of FIG. 27 and FIG. 28, respectively, may further function to transmit collected energy to a target medical device (2700 and 2810). The energy may be transmitted by a variety of modes including conducted electricity, radiation such as radio waves (for example, around 1 MHz), microwave, visible light, infrared light (for example, around 1 micron wavelength), etc., and ultrasound (for example, around 1 MHz in frequency) or a combination of modes. Energy may be supplemented either indirectly by applying cyclical pressure to the implantable power generator (manually or by other methods), or directly by applying a compatible mode of transmitted energy directly to the medical device. A wide range of medical devices can benefit from this technology including cardiac stimulators, neurostimulators, diagnostic devices, drug pumps and cardiac assist devices. Some devices that otherwise would not be practical due to size constraints or other difficulties in implementation can be enabled by this technology.

Figure 29:
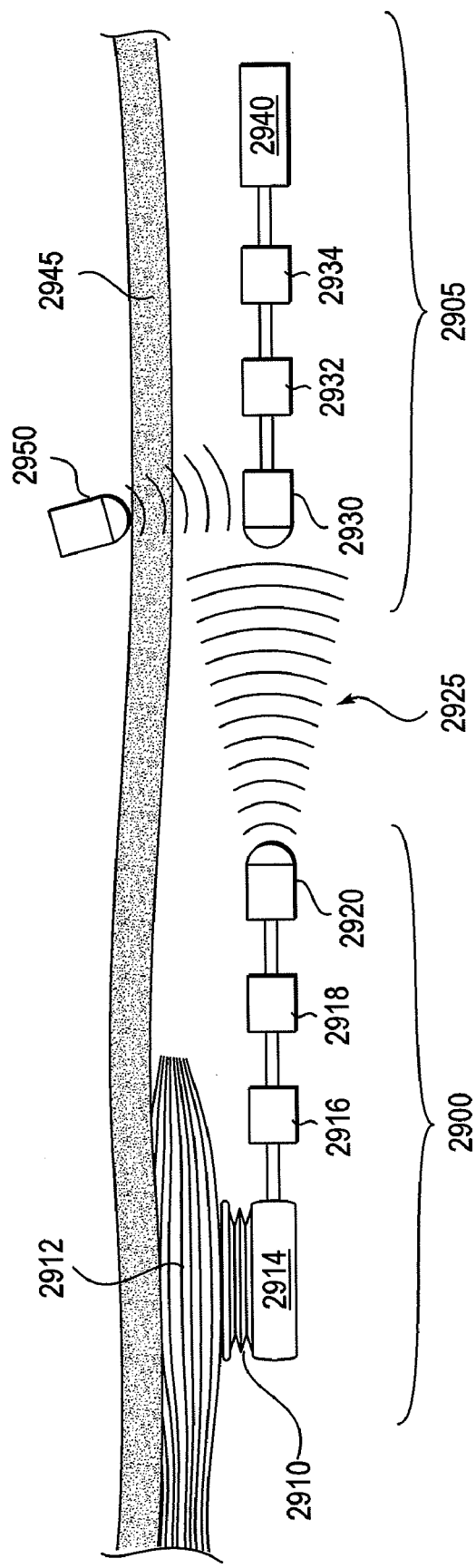
FIG. 29 is a drawing of an embodiment of a system for powering a medical device.

As shown in FIG. 29, a basic architecture for an implantable power generator 2900 that transmits energy to an implanted medical device 2905 and that uses the transmitted energy for power may include a compressible element 1910 (a bellows for example) to couple the pressure cycles from an overlying muscle 2912 to the transducer 2914. The electrical energy from a transducer 2914 may be variable in polarity and amplitude and is conditioned by a suitable conversion circuit 2916 such as a buck-boost circuit, or simply a diode bridge. The converted electrical energy is stored in a storage element 2918 such as a capacitor or a rechargeable battery, or a combination of both. The storage element is comparatively large (approximately 10 milliamp hours for example) and provides continuous energy availability despite irregular availability of pressure from the overlying muscle. The electrical energy from the storage element is transformed into a suitable form for transmission to the medical implant 2905 by a transmitter 2920. In some embodiments, the mode of energy transmission is electromagnetic, and the transmitter includes a coil or antenna or other suitable structure. In some embodiments, the mode of energy transmission is infrared light and the transmitter includes an IR-LED or infrared laser diode. In some embodiments, the mode of energy transmission is ultrasound and the transmitter includes an ultrasound transducer (typically a piezoelectric ceramic or electromagnetic mechanism). In some embodiments, the mode is electricity conducted through the body and the transmitter includes tissue contact electrodes. The energy from the transmitter is coupled into the body 2925 where it travels until it reaches the implanted medical device 2905. The medical device has a receiver 2930 that couples the transmitted energy from the body to a conditioning circuit 2932. In some embodiments, the mode of energy transmission is electromagnetic and the receiver includes a coil or antenna or other suitable structure. In some embodiments, the mode of energy transmission is infrared light and the receiver includes an IR-LED photodiode, solar cell or similar suitable device. In some embodiments, the mode of energy transmission is ultrasound and the receiver includes an ultrasound receiver (typically a piezoelectric ceramic transducer). In some embodiments, the mode of energy transmission is conducted electricity and the receiver includes tissue contact electrodes.

The conditioning circuit 2932 transforms the electrical signal from the receiver 2930 into a form suitable for storage in a storage device 2934. The conditioning circuit 2932 may be a capacitive voltage multiplier or simply a diode bridge. The storage device in the medical device is comparatively small and may be a bypass capacitor, a small super capacitor, or a very small thin film rechargeable battery having for example less than a milliamp-hour capacity. The storage device then powers the circuitry of the implanted medical device 2940. As shown in FIG. 29, the implantable power generator 2900 transmits energy to the medical device through the tissue 2925. It is also anticipated that the transmission may be over a wire (using the tissue 2925 as a return path) or over wires.

In some embodiments, as shown in FIG. 29, a system for powering a medical device includes an implantable power generator 2900 for converting mechanical energy from a patient to electrical energy, a storage device (2918 or 2934) that collects electrical energy from the transducer 2914 of the power generator, an auxiliary power supply 2950, and a medical device 2940 coupled to at least one of the storage device and the auxiliary power supply that receives electrical energy from at least one of the storage device and the auxiliary power supply. In some embodiments, the power generator includes a compressible element 2910 adapted and configured to be placed between two adjacent tissue layers of the patient (one tissue layer shown as muscle 2912) and to be compressed by a force applied from the two adjacent tissue layers to the compressible element, and a transducer 2914, coupled to the compressible element, that converts mechanical energy from the compression of the compressible element to electrical energy. The system may be designed to harvest mechanical energy from a patient, and more specifically to harvest mechanical energy from muscle contraction and to convert this mechanical energy into electrical energy. In some embodiments, the electrical energy generated may be used to power a medical device and, more specifically, to power an implantable medical device such as a neurostimulator or a cardiac pacemaker. The system may be alternatively used in any suitable environment and for any suitable reason.

As shown in FIG. 29, a basic architecture for an implantable power generator 2900 that transmits energy to an implanted medical device 2905 and that uses the transmitted energy for power may include a compressible element 1910 (a bellows for example) to couple the pressure cycles from an overlying muscle 2912 to the transducer 2914. The electrical energy from a transducer 2914 may be variable in polarity and amplitude and is conditioned by a suitable conversion circuit 2916 such as a buck-boost circuit, or simply a diode bridge. The converted electrical energy is stored in a storage element 2918 and/or 2934 such as a capacitor or a rechargeable battery, or a combination of both. The storage element is comparatively large (approximately 10 milliamp hours for example) and provides continuous energy availability despite irregular availability of pressure from the overlying muscle. The electrical energy from the storage element is transformed into a suitable form for transmission to the medical implant 2905 by a transmitter 2920. In some embodiments, in the event that power stored by the storage device and/or available from the overlying muscle 2912 is insufficient, additional power may be directly transmitted into the receiver 2930 from an auxiliary power supply 2950. In some embodiments, the auxiliary power supply is a battery, a capacitor, or other suitable power supply. In some embodiments, the auxiliary power supply is external to the patient's skin 2945, but may alternatively be implanted in the patient. In some embodiments, the auxiliary power supply may be coupled to the medical device percutaneously. In some embodiments, the auxiliary power supply may provide energy to the medical device continuously. Alternatively, power may be supplied as needed, such as upon request from the medical device. In some embodiments, the medical device may receive energy from the auxiliary power supply, when the power supply is positioned adjacent to the medical device and/or implantable power generator. For example, if the medical device and the implantable power supply are implanted in a patient's head, the auxiliary power supply may provide energy to the medical device when it is held up to a patient's head, such as against the cheek or temple of the patient.

In some embodiments, the auxiliary power supply includes a transmitter that couples the auxiliary power supply to the medical device and transmits electrical energy from the auxiliary power supply to the medical device. In some embodiments, if the mode of energy transmission is electromagnetic, and the transmitter includes a coil or antenna or other suitable structure. In some embodiments, the mode of energy transmission is infrared light and the transmitter includes an IR-LED or infrared laser diode. In some embodiments, the mode of energy transmission is ultrasound and the transmitter includes an ultrasound transducer (typically a piezoelectric ceramic or electromagnetic mechanism). In some embodiments, the mode is electricity conducted through the body and the transmitter includes tissue contact electrodes. The energy from the transmitter is coupled into the body 2925 where it travels until it reaches the implanted medical device 2905. The medical device has a receiver 2930 that couples the transmitted energy from the body to a conditioning circuit 2932.

In some embodiments, it may be advantageous for the implanted medical device to communicate with the implantable power generator. Such communications may use the same transmission mode as for transmitting energy or may be a different mode. The communications allows the medical device to control the amount of energy flowing from the implantable power generator to the medical device as the demand for energy changes, in other words, the medical device may "request" power from the implantable power generator when needed. Minimizing the amount of energy transmitted results in the system operating at a higher level of efficiency.

Experimental Results

One specific embodiment of a power generator was implanted in an animal model. In this experimental embodiment, the system included an implantable device and an external device in communication with the implantable device. The external device included a RF signal demodulator and a recording device. The components of the implanted device included a pressure sensor and a compressible element, connected by a lead wire. The pressure sensor included a printed circuit board having a Wheatstone bridge and various components to enable a radio frequency communication between the implanted device and the external device across a minimum distance of approximately 15 mm. The compressible element in the experimental embodiment was a fluid filled pillow structure that enveloped a pressure transducer and transferred the transverse pressure of the temporalis to the transducer. The compressible element and transducer configuration was similar to the ninth-eleventh embodiments as shown in FIGS. 13A-15.

The method of implanting the experimental device into an animal model (Animal: hound, Gender: female) included the steps of first creating a posterior-anterior incision medially at the shoulder (~3 cm) of the animal and creating a posterior-anterior incision (medially over the head (~6 cm) of the animal. A tunnel having a diameter of approximately 1.5 cm was then created from the shoulder to the head incision. The pressure sensor of the implanted device was then placed in the shoulder incision, left to the medial line. The pressure transducer of the implanted device was then pulled through the tunnel towards the head, leaving the pressure sensor in place near the shoulder incision. Ample lubrication was applied to the pressure transducer portion of the device prior to tugging it through the tunnel. An incision was then made in a muscle of the head of the animal, just in front of the ear. A forceps was used to create a channel under the temporalis muscle to the skull surface, exiting on the posterior side of the temporalis muscle. The pressure transducer portion of the device was then tunneled through this channel, again while applying lubrication. The implanted portions of the device were sutured to surrounding tissue to prevent excessive travel of movement of the implanted components. The posterior incisions near the temporalis muscle were sutured and the medial incision was closed. The anterior incision was sutured after the device was secured.

Postoperatively, the device responded to an external application of pressure on the temporalis muscle of the animal. The device also responded to a manual manipulation of the lower jaw (i.e. manually opening and closing the lower jaw). A manual opening of the jaw of the animal resulted in a force of 35 [N]. The device further responded to, and measured pressures generated by the temporalis muscle while the animal chewed on a chew toy.

Figure 30:
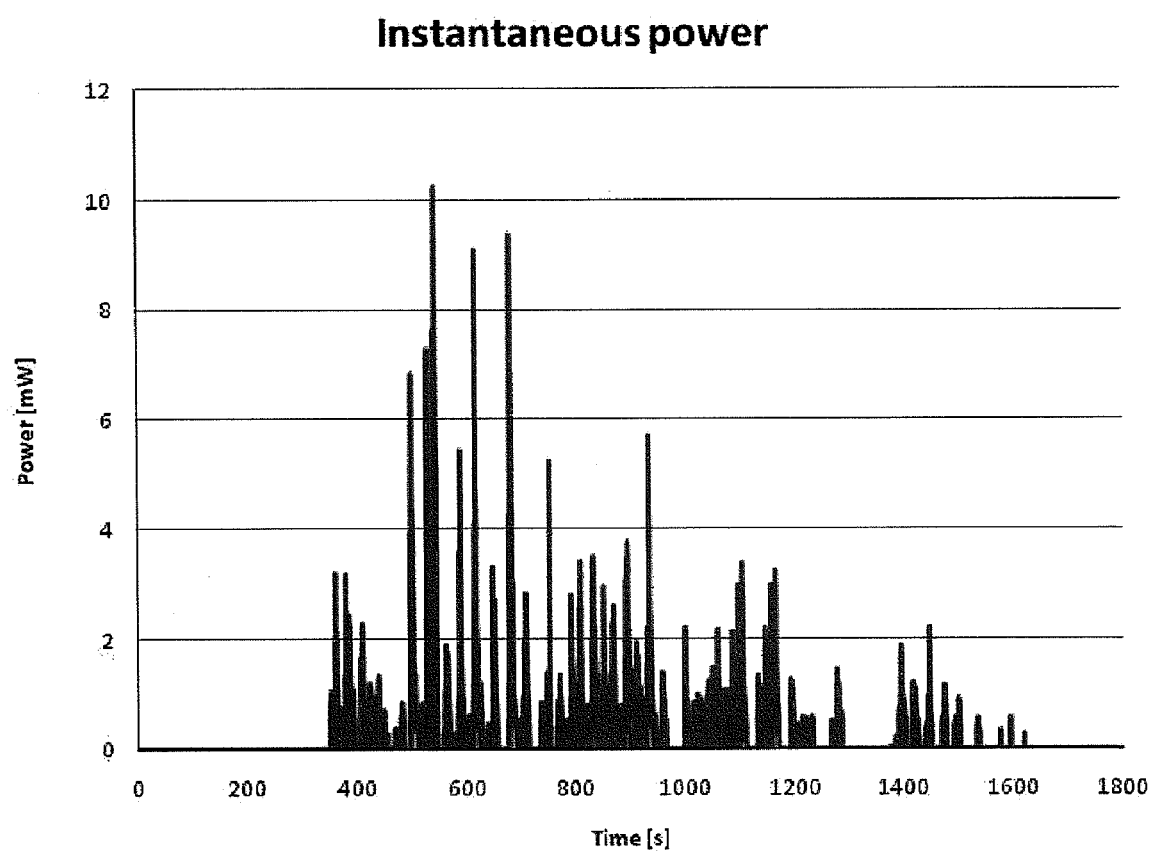
FIG. 30 is a graph of instantaneous power generated during a feeding period of a mammal.
Figure 31:
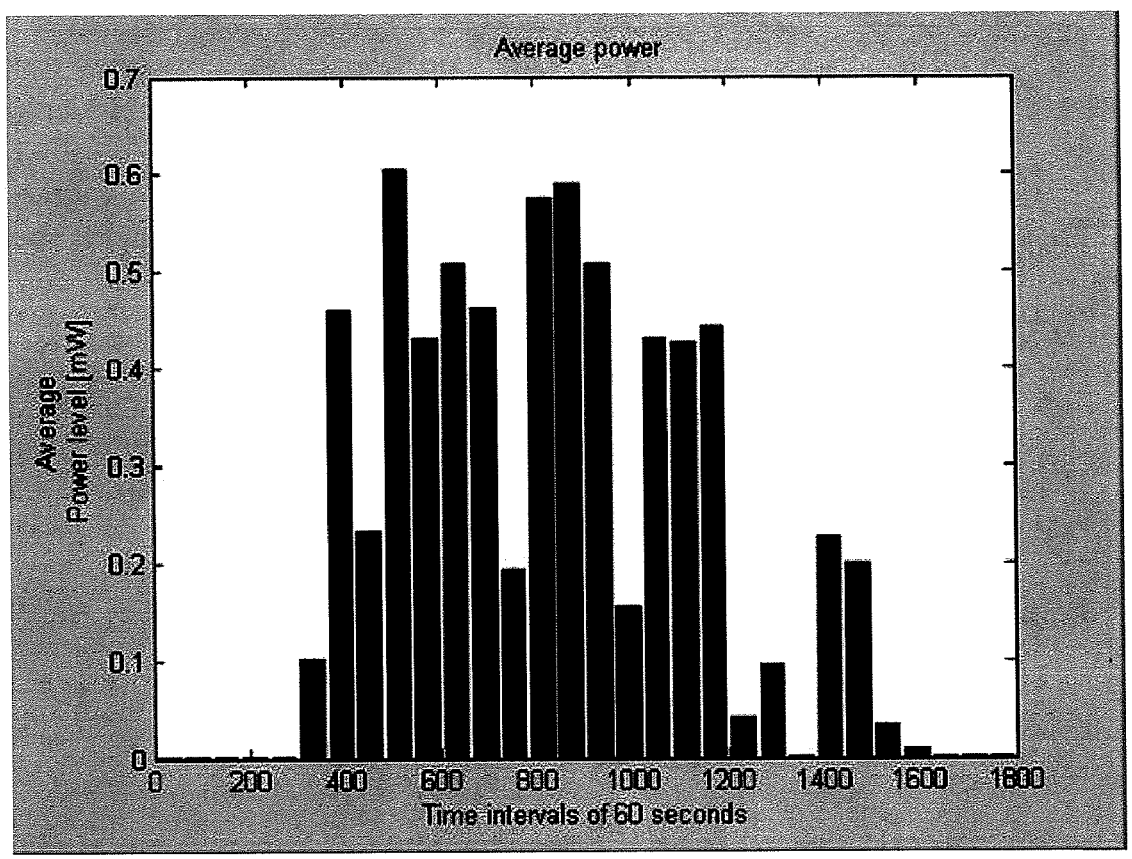
FIG. 31 is a graph of average power recorded for 60 second intervals during a feeding period of a mammal.
Figure 32:
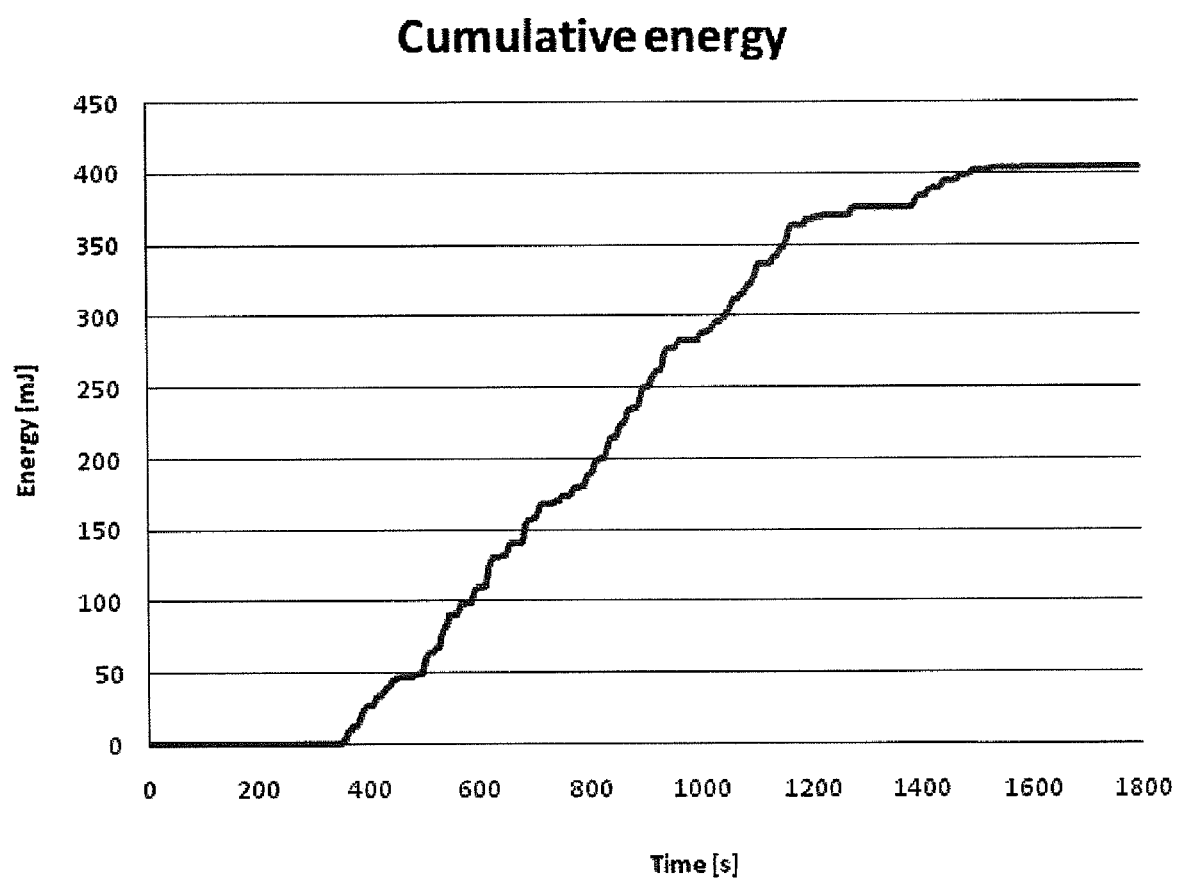
FIG. 32 is a graph of cumulative energy generated as a function of time during a feeding period of a mammal.

A second experiment was conducted with a device implanted in a second animal model: a porcine model. FIGS. 30-32 illustrate the experimental findings of that experiment.

FIG. 30 illustrates the instantaneous power generated during a feeding period. As shown, the recording of the signal from the implanted device began before the feeding of the animal (from 0 seconds to about 375 seconds). As shown, there is an initial burst of chewing by the animal, which registers as power generated (in mW) by the implanted device. The initial burst of chewing lasted for about 1200 seconds (from about 400 seconds to about 1600 seconds). Initially, the implanted device experienced some vigorous chewing (from about 450 seconds to about 650 seconds) as shown by the peaks of power generated, reaching upwards of about 10 mW. FIG. 31 illustrates the average power recorded for 60 second intervals. FIG. 31 illustrates a bar graph of the instantaneous power plotted in FIG. 30, averaged over 60 second intervals.

FIG. 32 illustrates the cumulative energy generated as a function of time. Again, as shown, the recording of the signal from the implanted device began before the feeding of the animal (from 0 seconds to about 375 seconds). From about 375 seconds on, energy is generated by the device, and during the period of 1800 seconds shown in FIG. 32, the total amount of energy generated is 403 mW. As shown, the initial burst of chewing lasted for about 1200 seconds (from about 400 seconds to about 1600 seconds) and no energy is accumulated after that time (the slope of the plotted line plateaus). The average power over this period is equal to about 0.22 mW.

As a person skilled in the art will recognize from the previous detailed description and from the figures and claims, modifications and changes can be made to the various illustrative embodiments of the invention without departing from the scope of this invention defined in the following claims. Furthermore, it is to be appreciated that the devices, systems, and methods are not to be limited to generating and/or converting electrical energy from the mechanical movement of a user's body while the power generator is worn by the user or implanted in the user. The power generator may be adapted to harvest energy from other sources as well. For example, the movement of the compressible element of the power generator may be powered or activated by environmental sources such as wind, tidal, water, solar, or other industrial sources such as industrial equipment.

We claim:

1. A power generator for converting mechanical energy to electrical energy, the generator comprising:
   a housing that defines a chamber;
   a phase changing dielectric fluid contained within the chamber of the housing;
   a moveable surface, coupled to the housing, that defines the volume of the phase changing dielectric fluid, wherein as the moveable surface moves from a first position toward a second position, the volume of the phase changing dielectric fluid is changed, such that the phase changing dielectric fluid transitions at least in part between a first phase with a first dielectric constant and a second phase with a second dielectric constant; and
   a capacitor within the chamber of the housing, the capacitor comprising a first plate and a second plate that define a space between them that contains a portion of the phase changing dielectric fluid, wherein the plates have a first voltage across them when the dielectric fluid is in the first phase and have a second voltage across them when the dielectric fluid is in the second phase.

2. The power generator of claim 1, the housing further comprising a spring element that biases the movable surface toward the first position.

3. The power generator of claim 1, wherein moveable surface comprises a flexible surface.

4. The power generator of claim 1, wherein moveable surface comprises a bellows.

5. The power generator of claim 1, the housing further comprising a base, substantially opposite to the movable surface, wherein the moveable surface moves relative to the base.

6. The power generator of claim 5, wherein the base is adapted and configured to be coupled to a first tissue layer of a patient, and the moveable surface is adapted and configured to be coupled to a second adjacent tissue layer of a patient, wherein a force applied from the two adjacent tissue layers to the housing moves the movable surface with respect to the base and reduces the volume of the chamber.

7. The power generator of claim 6, wherein the first tissue layer is a firm tissue layer, the second tissue layer is a muscle layer, and the force applied to the housing is generated by the muscle contracting adjacent to the firm tissue layer.

8. The power generator of claim 6, wherein the first and second tissue layers are muscle layers within a muscle and the force applied to the housing is generated by the muscle contracting.

9. The power generator of claim 5, wherein the base is a substantially rigid surface and the moveable surface comprises a piston head.

10. The power generator of claim 9, wherein the movable surface defines first chamber and a second chamber within the housing and the capacitor is within the second chamber.

11. The power generator of claim 1, further comprising a circuit that collects electrical energy from the capacitor as the voltage transitions from the first voltage to the second voltage.

12. The power generator of claim 1, wherein the circuit further functions to apply a voltage to the plates when the dielectric fluid is in the first phase.

13. The power generator of claim 1, wherein the first phase is a gas phase and the second phase is a liquid phase.

14. The power generator of claim 13, wherein the ratio of second dielectric constant to first dielectric constant is greater than 5.

15. The power generator of claim 13, wherein the ratio of second dielectric constant to first dielectric constant is greater than 20.

16. The power generator of claim 1, wherein the first phase is a gas phase and the second phase is a solid phase.

17. The power generator of claim 1, wherein the first phase is a liquid phase and the second phase is a solid phase.

18. The power generator of claim 1, wherein the phase changing dielectric fluid is water.

19. The power generator of claim 1, the plates further comprising a surface treated to facilitate a phase change of the dielectric fluid.

20. The power generator of claim 1, the capacitor further comprising a non-conductive spacer between the plates.

21. The power generator of claim 20, wherein the non-conductive spacer is a porous material disposed between the two plates.

22. A power generator for converting mechanical energy to electrical energy, the generator comprising:
 a housing that defines a chamber and comprises a movable surface;
 a dielectric fluid contained within the chamber of the housing;
 a capacitor within the chamber of the housing, the capacitor comprising:
  a first and second plate, and
  an insulator coupled to the first plate and disposed between the first plate and the second plate,
 wherein at least one plate is coupled to a movable surface of the housing,
 wherein the plates have a first voltage across them when a first amount of the dielectric fluid is between the insulator and the second plate, and have a second voltage across them when a second amount of the dielectric fluid is between the insulator and the second plate;
 wherein the movable surface moves from a first position toward a second position and displaces the dielectric fluid such that the first amount of the dielectric fluid is greater than the second amount of the dielectric fluid, the housing further comprising a spring element that returns the movable surface to the first position, the spring element comprising a compliant portion coupled to the housing and a non-compliant portion, coupled to the compliant portion, wherein the non-compliant portion and the compliant portion define a fluid filled chamber.

23. The power generator of claim 22, wherein as a force is applied to the housing and the movable surface displaces the dielectric fluid, the dielectric fluid moves a portion of the compliant portion into the fluid filled chamber, thereby compressing the fluid in the chamber.

24. The power generator of claim 23, wherein when the force is no longer applied to the housing, the fluid in the chamber moves the portion of the compliant portion out of the fluid filled chamber, thereby replacing dielectric fluid between the insulator and the second plate.

25. A method for generating power, the method comprising:
 positioning a capacitor in a phase changing dielectric fluid contained within a chamber, the capacitor comprising a first plate and a second plate that define a space between them that contains a portion of the phase changing dielectric fluid;
 applying a first voltage to at least one of the plates of the capacitor;
 changing the phase of the phase changing dielectric fluid such that it transitions at least in part between a first phase with a first dielectric constant and a second phase with a second dielectric constant;
 collecting a second voltage from at least one of the plates of the capacitor, wherein the plates of the capacitor have the second voltage across them when the dielectric fluid is in the second phase.

26. The method of claim 25, the changing step further comprising changing the pressure of the phase changing dielectric fluid such that the phase changing dielectric fluid transitions at least in part between a first phase and a second phase.

27. The method of claim 26, the changing step further comprising applying a mechanical input to change the pressure of the phase changing dielectric fluid.

28. The method of claim 25, the changing step further comprising changing the temperature of the phase changing dielectric fluid such that the phase changing dielectric fluid transitions at least in part between a first phase and a second phase.

29. The method of claim 25, the changing step further comprising changing the volume of the phase changing dielectric fluid such that the phase changing dielectric fluid transitions at least in part between a first phase and a second phase.

30. The method of claim 29, the changing step further comprising applying a mechanical input to change the volume of the phase changing dielectric fluid.

31. The method of claim 25, the changing step further comprising applying an ultrasound signal to the phase changing dielectric fluid to change the phase of the phase changing dielectric fluid.

32. The method of claim 25, the changing step further comprising applying radiofrequency signal to the phase changing dielectric fluid to change the phase of the phase changing dielectric fluid.

33. The method of claim 25, the changing step further comprising applying a laser to the phase changing dielectric fluid to change the phase of the phase changing dielectric fluid.

34. The method of claim 25, the changing step further comprising changing the phase of the dielectric fluid such that it transitions at least in part between a gas phase and a liquid phase.

35. The method of claim 25, the changing step further comprising changing the phase of the dielectric fluid such that it transitions at least in part between a gas phase and a solid phase.

36. The method of claim 25, the changing step further comprising changing the phase of the dielectric fluid such that it transitions at least in part between a liquid phase and a solid phase.

37. An implantable power generator for converting mechanical energy from a patient to electrical energy, the generator comprising:
a compressible element adapted and configured to be placed between two adjacent tissue layers of the patient and to be compressed by a force applied from the two adjacent tissue layers to the compressible element, the compressible element comprising a substantially rigid base adapted and configured to be coupled to a first tissue layer, and a piston head, substantially opposite to the base, adapted and configured to be coupled to a second tissue layer, wherein the force applied from the two adjacent tissue layers to the compressible element moves the piston head with respect to the base; and
a transducer, coupled to the compressible element, that converts mechanical energy from the compression of the compressible element to electrical energy.

38. An implantable power generator for converting mechanical energy from a patient to electrical energy, the generator comprising:
a compressible element defining a chamber and comprising a fluid within the chamber, the compressible element adapted and configured to be placed between two adjacent tissue layers of the patient and to be compressed by a force applied from the two adjacent tissue layers to the compressible element, wherein, upon compression of the compressible element, the compressible element displaces the fluid from within the chamber of the compressible element, thereby generating a fluid pressure;
a transducer, coupled to the compressible element, that converts mechanical energy from the compression of the compressible element to electrical energy; and
a transmission, coupled to the compressible element and to the transducer, that transforms a motion from the compression of the compressible element into a rotational motion.

39. The implantable power generator of claim 38, the transmission further comprising a wheel that transforms a fluid pressure from the compression of the compressible element into a rotational motion.

40. The implantable power generator of claim 38, the transmission further comprising a rack and a pinion that transforms the motion from the compression of the compressible element into a rotational motion.

41. The implantable power generator of claim 38, the transmission further comprising a threaded spindle and a threaded cylinder, coupled to the threaded spindle, that transforms the motion from the compression of the compressible element into a rotational motion.

42. The implantable power generator of claim 38, the transducer comprising an electromagnetic generator coupled to the transmission.

43. The implantable power generator of claim 42, wherein the rotational motion from the transmission drives the electromagnetic generator, such that the electromagnetic generator converts the rotational motion to electrical energy.

44. The implantable power generator of claim 38, the compressible element further comprising a flexible housing and a structural member, coupled to the housing and to the transducer, that transmits a force from the housing to the transducer such that, upon compression of the compressible element, the housing compresses and the structural member applies a tension force to the transducer, the structural member comprising three substantially rigid members, disposed within the housing, wherein upon compression of the compressible element, the housing compresses and the structural member transitions from a triangular arrangement having a first perimeter to a substantially horizontal arrangement having a second perimeter.

45. The implantable power generator of claim 44, wherein the transducer is coupled to the structural member such that upon compression of the compressible element, the structural member applies a tension force to the transducer, such that the transducer transitions from a first perimeter to a second perimeter.

46. The implantable power generator of claim 45, the transducer comprising an electroactive polymer that has a first capacitance in the first perimeter and a second capacitance in the second perimeter.

47. An implantable power generator for converting mechanical energy from a patient to electrical energy, the generator comprising:
a compressible element adapted and configured to be placed between two adjacent tissue layers of the patient and to be compressed by a force applied from the two adjacent tissue layers to the compressible element, the compressible element defining a chamber and further comprising a fluid within the chamber; and
a transducer, coupled to the compressible element, the transducer comprising a capacitor within the chamber, having a first plate and a second plate, wherein the fluid is a phase changing dielectric fluid and the plates have a first voltage across them when the dielectric fluid is in a first phase and have a second voltage across them when the dielectric fluid is in a second phase, wherein the transducer converts mechanical energy from the compression of the compressible element to electrical energy.

48. The implantable power generator of claim 47, the compressible element comprising:
a base adapted and configured to be coupled to the first tissue layer; and
a moveable surface, substantially opposite to the base, adapted and configured to be coupled to the second tissue layer;
wherein the base and the movable surface define the volume of the chamber, and the force applied from the two adjacent tissue layers to the compressible element moves the movable surface with respect to the base, such that the volume of the phase changing dielectric fluid is changed and the phase changing dielectric fluid transitions between the first phase with a first dielectric constant and the second phase with a second dielectric constant.

49. The power generator of claim 47, further comprising a circuit that collects electrical energy from the capacitor as the voltage transitions from the first voltage to the second voltage.

50. The power generator of claim 49, wherein the circuit further functions to apply a voltage to the plates when the dielectric fluid is in the first phase.

51. The power generator of claim 47, wherein the first phase is a gas phase and the second phase is a liquid phase.

52. The power generator of claim 51, wherein the ratio of second dielectric constant to first dielectric constant is greater than 5.

53. The power generator of claim 51, wherein the ratio of second dielectric constant to first dielectric constant is greater than 20.

54. The power generator of claim 47, wherein the phase changing dielectric fluid is water.

55. The implantable power generator of claim 48, wherein the base is a substantially rigid surface and the moveable surface comprises a piston head.

56. The power generator of claim 55, wherein the movable surface defines a first chamber and a second chamber within the housing and the capacitor is within the second chamber.

* * * * *